US010030273B2

(12) United States Patent
Marsh et al.

(10) Patent No.: US 10,030,273 B2
(45) Date of Patent: Jul. 24, 2018

(54) MICRORNA EXPRESSION IN HUMAN PERIPHERAL BLOOD MICROVESICLES AND USES THEREOF

(71) Applicant: OHIO STATE INNOVATION FOUNDATION, Columbus, OH (US)

(72) Inventors: Clay B. Marsh, Columbus, OH (US); Melissa G. Piper, Columbus, OH (US); Noura Ismail, Columbus, OH (US)

(73) Assignee: OHIO STATE INNOVATION FOUNDATION, Columbus, OH (US)

( * ) Notice: Subject to any disclaimer, the term of this patent is extended or adjusted under 35 U.S.C. 154(b) by 0 days.

(21) Appl. No.: 15/274,788

(22) Filed: Sep. 23, 2016

(65) Prior Publication Data

US 2017/0009306 A1    Jan. 12, 2017

Related U.S. Application Data

(63) Continuation of application No. 13/873,371, filed on Apr. 30, 2013, now abandoned, which is a continuation of application No. 12/677,931, filed as application No. PCT/US2008/076109 on Sep. 12, 2008, now Pat. No. 8,455,199.

(60) Provisional application No. 61/055,178, filed on May 22, 2008, provisional application No. 60/993,809, filed on Sep. 14, 2007.

(51) Int. Cl.
*C12Q 1/68* (2018.01)
*C12Q 1/6886* (2018.01)
*C12N 15/11* (2006.01)
*C12N 15/113* (2010.01)
*C12Q 1/6809* (2018.01)

(52) U.S. Cl.
CPC .......... *C12Q 1/6886* (2013.01); *C12N 15/111* (2013.01); *C12N 15/113* (2013.01); *C12Q 1/6809* (2013.01); *C12N 2310/141* (2013.01); *C12N 2320/12* (2013.01); *C12Q 2600/158* (2013.01); *C12Q 2600/16* (2013.01); *C12Q 2600/178* (2013.01)

(58) Field of Classification Search
None
See application file for complete search history.

(56) References Cited

U.S. PATENT DOCUMENTS

| | | |
|---|---|---|
| 5,089,181 A | 2/1992 | Hauser |
| 6,812,023 B1 | 11/2004 | Lamparski et al. |
| 7,888,010 B2 | 2/2011 | Brown et al. |
| 7,897,356 B2 | 3/2011 | Klass et al. |
| 8,021,847 B2 | 9/2011 | Pietrzkowski |
| 8,148,069 B2 | 4/2012 | Croce et al. |
| 8,455,199 B2 | 6/2013 | Marsh et al. |
| 2003/0036077 A1 | 2/2003 | Chenchik et al. |
| 2003/0068642 A1 | 4/2003 | Urnovitz |
| 2005/0064470 A1 | 3/2005 | Rana |
| 2005/0158708 A1 | 7/2005 | Alroy et al. |
| 2005/0159378 A1 | 7/2005 | McSwiggen et al. |
| 2007/0059765 A1 | 3/2007 | Wang et al. |
| 2007/0077553 A1 | 4/2007 | Bentwich |
| 2007/0161004 A1 | 7/2007 | Brown et al. |
| 2008/0268429 A1 | 10/2008 | Pietrzkowski |
| 2009/0011428 A1 | 1/2009 | Nam et al. |
| 2009/0226887 A1 | 9/2009 | Brisson |
| 2013/0316925 A1 | 11/2013 | Marsh et al. |

FOREIGN PATENT DOCUMENTS

| | | |
|---|---|---|
| WO | WO-2005/118806 A2 | 12/2005 |
| WO | WO-2005/121369 A2 | 12/2005 |
| WO | WO-2007/081740 A2 | 7/2007 |
| WO | WO-2009/015357 A1 | 1/2009 |

OTHER PUBLICATIONS

Lu et al, Nature 435: 834 (2005).*
Mattie et al, Molecular Cancer 5: 24 (2006).*
Valenti et al, Cancer Research 66 (18), 9290 (2006).*
Ambros et al., The functions of animal microRNAs, Nature. Sep. 16, 2004;431(7006):350-5.
Andre et al. Malignant effusions and immunogenic tumour-derived exosomes. Lancet. Jul. 27, 2002;360(9329):295-305.
Andre, et al., Exosomes for cancer immunotherapy, Annals of Oncology, 2004, 15 (Supplement 4): iv141-iv144.
Andre, et al., Tumor-derived exosomes: a new source of tumor rejection antigens, Vaccine 20, 2002: A28-A31; available at www.elsevier.com/locate/vaccine.
Baj-Krzyworzeka et al., Tumour-derived microvesicles carry several surface determinants and mRNA of tumour cells and transfer some of these determinants to monocytes, Cancer Immunol Immunother (2006) 55: 808-818.
Bandres et al., Identification by Real-time PCR of 13 mature microRNAs differentially expressed in colorectal cancer and non-tumoral tissues, Molecular Cancer 2006, 5:29-38.
Barbarotto et al., MicroRNAs and cancer: Profile, profile, profile, Int. J. Cancer: 122, 969-977 (2008).
Bard, et al., Proteomic analysis of exosomes isolated from human malignant pleural effusions, Am. J. Respir. Cell Mol. Biol., 2004, vol. 31, pp. 114-121.
Bartel, DP, MicroRNAs: Genomics, biogenesis, mechanism, and function, Cell, 116, 2004, pp. 281-297.
Berek et al., Biologic and immunologic therapies for ovarian cancer, J Clin Oncol, 21 (s10), 2003, pp. 168-174.
Blower, et al. MicroRNAs modulate the chemosensitivity of tumor cells. Mol Cancer Ther. Jan. 2008;7(1):1-9. Epub Jan. 9, 2008.
Bohler et al., Endometriosis Markers: 1-20 Immunologic Alterations as Diagnostic Indicators for Endometriosis, Reproductive Sciences, vol. 14(6), 2007, pp. 595-604, Sage Publications, Inc., US.

(Continued)

*Primary Examiner* — James Martinell
(74) *Attorney, Agent, or Firm* — Marshall, Gerstein & Borun LLP

(57) ABSTRACT

The present invention provides novel methods and compositions for the diagnosis, prognosis and treatment of disorders by examining samples containing microvesicles and miRs therein.

14 Claims, 15 Drawing Sheets

(56) References Cited

OTHER PUBLICATIONS

Bruchova et al., The Regulated Expression of miRNAs in Normal and; Polycythemia Vera Erythropoiesis, Exp Hematol. Nov. 2007; 35(11): 1657-1667.
Brummelkamp et al., A system for stable expression of short interfering RNAs in mammalian cells, Science. Apr. 19, 2002;296(5567):550-3.
Caby, et al., Exosomal-like vesicles are present in human blood plasma, International Immunology, 2005, vol. 17, No. 7, pp. 879-887.
Calin et al., Frequent deletions and down-regulation of micro-RNA genes miR15 and miR16 at 13q14 in chronic lymphocytic leukemia, Proc Natl Acad Sci USA, 2002, 99(24):15524-15529.
Calin et al., Genomics of Chronic Lymphocytic Leukemia MicroRNAs as New Players With Clinical Significance, Semin Oncol 33:167-173 (2006).
Calin et al., MicroRNA profiling reveals distinct signatures in B cell chronic lymphocytic leukemias, Proc Natl Acad Sci USA, 2004, 101(32):11755-11760.
Calin et al., MicroRNA signatures in human cancers, Nature Rev Cancer, 6, 2006b, pp. 857-866.
Calin et al., MicroRNA-cancer connection: the beginning of a new tale, Cancer Res, 66, 2006a, pp. 7390-7394.
Calin et al., MiR-15a and miR-16-1 cluster functions in human leukemia, Proc Natl Acad Sci USA, 2008, 105(13): 5166-5171.
Cameron et al., Epstein-Barr Virus Latent Membrane Protein 1 Induces Cellular MicroRNA miR-146a, a Modulator of Lymphocyte Signaling Pathways, Journal of Virology, Feb. 2008, pp. 1946-1958.
Canadian patent application No. 2699646, Examination Report, dated Dec. 14, 2015.
Ceccarini, et al., Biochemical and NMR studies on structure and release conditions of RNA-containing vesicles shed by human colon adenocarcinoma cells, Int. J. Cancer, 1989, vol. 44, pp. 714-721.
Chen et al., Microfluidic isolation and transcriptome analysis of serum microvesicles, Lab Chip, 2010, vol. 10, pp. 505-511.
Chen et al., MicroRNAs modulate hematopoietic lineage differentiation, Science. Jan. 2, 2004;303(5654):83-6.
Cheng et al., Antisense inhibition of human miRNAs and indications for an involvement of miRNA in cell growth and apoptosis, Nucleic Acids Research, 2005, vol. 33, No. 4 pp. 1290-1297.
Chinese patent application No. 200880114286.9, First Office Action (English translation), dated Sep. 21, 2011.
Chinese patent application No. 200880114286.9, Second Office Action (English translation), dated Jun. 18, 2012.
Choi et al., Proteomic analysis of microvesicles derived from human colorectal cancer cells, J Proteome Res, 6, 2007, pp. 4646-4655.
Clayton, et al., Analysis of antigen presenting cell derived exosomes, based on immune-magnetic isolation and flow cytometry, Journal of Immunological Methods, 2001, vol. 247, pp. 163-174.
Cummins et al., Implications of micro-RNA profiling for cancer diagnosis, Oncogene, 25, 2006, pp. 6220-6227.
De Cecco et al., Gene expression profiling of advanced ovarian cancer: Characterisization of a molecular signature involving fibroblast growth factor 2, Oncogene, 23, 2004, pp. 8171-8183.
Dolo, et al., Membrane vesicles shed into the extracellular medium by human breast carcinoma cells carry tumor-associated surface antigens, Clin. Exp. Metastasis, 1995, vol. 13, pp. 277-286.
Draghici Sorin et al., Epitomics: Serum Screening for the Early Detection of Cancer on Microarrays Using Complex Panels of Tumor Antigens, Expert Review of Molecular Diagnostics, vol. 5, No. 5, 2005, pp. 735-743.
Dresios et al., Cold stress-induced protein Rbm3 binds 60S ribosomal subunits, alters microRNA levels, and enhances global protein synthesis, Proc Natl Acad Sci USA, 2005 102(6):1865-1870.
Escola et al., Selective enrichment of tetraspan proteins on the internal vesicles of multivesicular endosomes and on exosomes secreted by human B-lymphocytes, J Biol Chem, 273, 1998, pp. 20121-20127.
Esquela-Kerscher et al., Oncomirs-microRNAs with a role in cancer, Nature Rev Cancer, 6, 2006, pp. 259-269.
European patent application No. 08830849.9, Official Action, dated Mar. 20, 2012.
European patent application No. 08830849.9, European search report and search opinion dated Jan. 21, 2011.
European Patent Application No. 13161709, European Search Report and Search Opinion dated Jun. 3, 2013.
European Patent Application No. 16167453.6, European Search Report and Opinion, completed Oct. 13, 2016.
Fazi et al., A Minicircuitry Comprised of MicroRNA-223 and Transcription Factors NFI-A and C/EBPalpha Regulates Human Granulopoiesis, Cell 2005, 123, 819-831.
Felli et al., MicroRNAs 221 and 222 inhibit normal erythropoiesis and erythroleukemic cell growth via kit receptor down-modulation, Proc Natl Acad Sci USA, 2005, 102(50):18081-18086.
Fevrier, et al., Exosomes: endosomal-derived vesicles shipping extracellular messages, Current Opinion in Cell Biology, 2004, vol. 16, pp. 415-421.
Fulci et al., Quantitative technologies establish a novel microRNA profile of chronic lymphocytic leukemia, Blood 2007 109:4944-4951.
Garzon et al., MicroRNA fingerprints during human megakaryocytopoiesis, Proc Natl Acad Sci USA, 2006, 103(13):5078-5083.
Gassart, et al., Lipid raft-associated protein sorting in exosomes, Blood, Dec. 15, 2003, vol. 1 02, No. 13, pp. 4336-4344; available at bloodjournal.hematologylibrary.org, accessed Dec. 17, 2011.
Gottardo et al., Micro-RNA profiling in kidney and bladder cancers, Urol Oncol. Sep.-Oct. 2007;25(5):387-92.
Guglielmelli et al., MicroRNA expression profile in granulocytes from primary myelofibrosis patients, Exp Hematol. Nov. 2007;35(11):1708-18.
Handbook of Chemistry and Physics, 49th Edition, 1968, Weast (ed.), The Chemical Rubber Co., Cleveland, Ohio, p. A-245-Combination Equation.
Hariharan et al., Targets for human encoded microRNAs in HIV genes, Biochem Biophys Res Commun. Dec. 2, 2005;337(4)1 214-8.
Harris et al., MicroRNA-126 regulates endothelial expression of vascular cell adhesion molecule 1, Proc Natl Acad Sci USA, 2008, 105(5):1516-1521.
He et al., A microRNA polycistron as a potential human oncogene, Nature. Jun. 9, 2005;435(7043):828-33.
Herbert et al., High mobility group A2 is a target for miRNA-98 in head and neck squamous cell carcinoma, Molecular Cancer 2007, 6:5-15.
Huang et al., Cellular microRNAs contribute to HIV-1 latency in resting primary CD4+ T lymphocytes, Nat Med. Oct. 2007;13(10):1241-7.
Indian Patent Application No. 1981/CHENP/2010, First Examination Report, dated Jun. 13, 2014.
International search report and written opinion dated Jan. 12, 2009 for PCT Application No. US08/76109.
Iorio et al., MicroRNA signatures in human ovarian cancer, Cancer Res, 67, 2007, pp. 8699-8707.
Iorio et al. MicroRNA gene expression deregulation in human breast cancer. Cancer Res. Aug. 15, 2005;65(16):7065-7070.
Janowska-Wieczorek et al., Microvesicles derived from activated platelets induce metastasis and angiogenesis in lung cancer, Int. J. Cancer: 113, 752-760 (2005).
Japanese Patent Application No. 2010-525014, Notification of Reasons for Refusal (English translation), Jul. 24, 2013.
Japanese Patent Application No. 2010-525014, Notification of Reasons for Rejection (English translation), dated Mar. 13, 2014.
Johnnidis et al., Regulation of progenitor cell proliferation and granulocyte function by microRNA-223, Nature. Feb. 28, 2008;451(7182):1125-9.
Jungi et al., Platelet-leukocyte interaction: selective binding of thrombin-stimulated platelets to human monocytes, polymorphonuclear leukocytes, and related cell lines, Blood 1986 67: 629-636.

(56) References Cited

OTHER PUBLICATIONS

Keller et al., Body fluid derived exosomes as a novel template for clinical diagnostics, J. Translational Med., 2011, vol. 9:86, pp. 1-23.
Khalil, Biomarker discovery: A proteomic approach for brain cancer profiling, Cancer Sci., 2007, 98(2):, pp. 201-213.
Koga et al., Purification, characterization and biological significance of tumor-derived exosomes, Anticancer Res, 25,2005, pp. 3703-3707.
Kulshreshtha et al., A MicroRNA Signature of Hypoxia, Molecular and Cellular Biology, Mar. 2007, p. 1859-1867.
Lal et al., p16INK4a Translation Suppressed by miR-24, PLoS One, 2008 3(3):e1864.
Lamparski, et al., Production and characterization of clinical grade exosomes derived from dendritic cells, Journal of Immunological Methods, 2002, vol. 270, pp. 211-226.
Lawrie et al., Detection of elevated levels of tumour-associated microRNAs in serum of patients with diffuse large B-cell lymphoma, British Journal of Haematology, 141, 672-675.
Lee et al., Expression of small interfering RNAs targeted against HIV-1 rev transcripts in human cells, Nat Biotechnol. May 2002;20(5):500-5.
Lee et al., Systematic evaluation of microRNA processing patterns in tissues, cell lines, and tumors, RNA 2008 14: 35-42.
Lin et al., Loss of mir-146a function in hormone-refractory prostate cancer, RNA (2008), 14:417-424.
Liu et al., An oligonucleotide microchip for genome-wide microRNA profiling in human and mouse tissues, Proc Natl Acad Sci USA, 2004, 101(26):9740-9744.
Lu et al., MicroRNA expression profiles classify human cancers, Nature, 435, 2005, pp. 834-838.
Lukiw, Micro-RNA speciation in fetal, adult and Alzheimer's disease hippocampus, Neuroreport. Feb. 12, 2007;18(3):297-300.
Lyberg et al., Procoagulant (thromboplastin) activity in human bronchoalveolar lavage fluids is derived from alveolar macrophages, Eur Respir J. Jan. 1990;3(1):61-7.
Majka et al., Evidence that platelet-derived microvesicles may transfer platelet-specific immunoreactive antigens to the surface of endothelial cells and CD34+ hematopoietic stem/progenitor cells—implication for the pathogenesis of immune thrombocytopenias, Folia Histochemica et Cytobiologica, vol. 45, No. 1, 2007, pp. 2732.
Mears et al., Proteomic analysis of melanoma-derived exosomes by two-dimensional polyacrylamide gel electrophoresis and mass spectrometry, Proteomics, 4, 2004, pp. 4019-4031.
Meister et al., miRNAs Get an Early Start on Translational Silencing, Cell 131, Oct. 5, 2007, pp. 25-28.
Menon et al., Recent developments in ovarian cancer screening, Curr Opin Obstet Gynecol, 12, 2000, pp. 39-42.
Mi et al., MicroRNA expression signatures accurately discriminate acute lymphoblastic leukemia from acute myeloid leukemia, Proc Natl Acad Sci USA, 2007, 104(50):19971-19976.
Michael et al., Exosomes from Human Saliva as a Source of micro RNA Biomarkers, Oral Dis., Jan. 2010, vol. 16(1 ), pp. 34-38.
Millimaggi, et al., Tumor Vesicle-Associated CD147 Modulates the Angiogenic Capability of Endothelial Cells 1, Neoplasia, 2007, 9(4), pp. 349-357.
Miska, EA., How microRNAs control cell division, differentiation, and death, Curr Opin Genet Dev, 5, 2005, pp. 563-568.
Miyagishi et al., U6 promoter-driven siRNAs with four uridine 3' overhangs efficiently suppress targeted gene expression in mammalian cells, Nat Biotechnol. May 2002;20(5):497-500.
Monleon, et al., Differential secretion of fas ligand- or AP02 ligand/TNF-related apoptosis-inducing ligand-carrying microvesicles during activation-induced death of human t cells, The Journal of Immunology, 2001, vol. 167, pp. 6736-6744.
Monticelli et al., MicroRNA profiling of the murine hematopoietic system, Genome Biology 2005, 6:R71.
New Zealand Patent Application No. 583959, Office action dated Dec. 17, 2010.
Nieuwland et al., Cellular origin and procoagulant properties of microparticles in meningococcal sepsis, Blood 2000 95: 930-935.
Olver et al., Proteomic analysis of secreted exosomes, Subcell Biochem., 43, 2007, pp. 99-131.
Paddison et al., Short hairpin RNAs (shRNAs) induce sequence-specific silencing in mammalian cells, Genes & Development 16:948-958 2002.
Palacio et al., Anti-endometrial autoantibodies in women with a diagnosis of infertility, American Journal of Reproductive Immunology, vol. 38, Nr. 2, Aug. 1997, pp. 100-105.
Pang, et al., MicroRNAs and prostate cancer, Acta Biochim Biophys Sin, 2010, vol. 42(6), pp. 363-369.
Paul et al., Effective expression of small interfering RNA in human cells, Nat Biotechnol. May 2002;20(5):505-8.
Piccin et al., Circulating microparticles: pathophysiology and clinical implications, Elsevier Health, 2007, 21, pp. 157-171.
Plasterk et al., Micro RNAs in Animal Development, Cell 124, Mar. 10, 2006, pp. 877-881.
Porkka et al., MicroRNA Expression Profiling in Prostate Cancer, Cancer Res 2007;67:6130-6135.
Poy et al., A pancreatic islet-specific microRNA regulates insulin secretion, Nature. Nov. 11, 2004;432(7014):226-30.
Raposo et al., Accumulation of major histocompatibility complex class II molecules in mast cell secretory granules and their release upon degranulation, Mol Biol Cell, 8, 1997, pp. 2631-2645.
Ratajczak et al., Embryonic stem cell-derived microvesicles reprogram hematopoietic progenitors: Evidence for horizontal transfer of mRNA and protein delivery, Leukemia, 20, 2006, pp. 847-856.
Ratajczak et al., Membrane-derived microvesicles: important and; underappreciated mediators of cell-to-cell communication, Leukemia, 20, 2006, pp. 1487-1495.
Rauch et al., Transfer of tissue factor from leukocytes to platelets is mediated by CD15 and tissue factor, Blood, Jul. 1, 2000 x vol. 96, No. 1. 170-175.
Raveche et al., Abnormal microRNA-16 locus with synteny to human 13q14 linked to CLL in NZB mice, Blood 2007 109: 5079-5086.
Roldo et al., MicroRNA Expression Abnormalities in Pancreatic Endocrine and Acinar Tumors Are Associated With Distinctive Pathologic Features and Clinical Behavior, J Clin Oncol 24:4677-4684.
Rosell et al., Circulating Micro RNA Signatures of Tumor-Derived Exosomes for Early Diagnosis of Non-Small-Cell Lung Cancer, Clin Lung Canc, 2009, vol. 10, pp. 8-9.
Ruscetti et al., Autocrine transforming growth factor-beta regulation of hematopoiesis: many outcomes that depend on the context, Oncogene (2005) 24, 5751-5763.
Sabapatha et al., Specific isolation of placental-derived exosomes from the circulation of pregnant women and their immunoregulatory consequences, Am J. Reprod Immunol, 56, 2006, pp. 345-355.
Sankaranarayanan, et al., Worldwide burden of gynaecological cancer: the size of the problem, Best Pract Res Clin Obstet & Gynaecol, 20, 2006, pp. 207-225.
Schetter et al., MicroRNA Expression Profiles Associated With Prognosis and Therapeutic Outcome in Colon Adenoearcinonia, IIV\1A. 2008;299(4):425-436, JAMA.
Sch Iera et al., Neurons produce FGF2 and VEGF and secrete them at least in part by shedding extracellular vesicles, J. Cell Mol. Med., 2007, 11(6), pp. 1384-1394.
Schmittgen et al., Real-time PCR quantification of precursor and mature microRNA, Methods. Jan. 2008 ; 44(1): 31-38.
Seligson et al., Epithelial Cell Adhesion Molecule (KSA) Expression: Pathobiology and Its Role as an Independent Predictor of Survival in Renal Cell Carcinoma, Clinical Cancer Research, vol. 10, 2004, pp. 2659-2669.
Setzer et al., Platelet-derived microvesicles induce differential gene expression in monocytic cells: A DNA microarray study, Platelets, Dec. 2006; 17(8): 571-576.
Shih et al., Exosomal microRNAs step into the biomarker arena, Gyn One, 2008, vol. 110, pp. 1-2.
Smets et al., Novel Biomarkers in Preeclampsia, Clinica Chimica Acta, 2006, vol. 364 (1-2), pp. 22-32.
Sugatani et al., MicroRNA-223 is a key factor in osteoclast differentiation, J Cell Biochem. Jul. 1, 2007;101(4):996-9.

(56) References Cited

OTHER PUBLICATIONS

Sun et al., Transforming growth factor-b-regulated miR-24 promotes skeletal muscle differentiation, 2690-2699 Nucleic Acids Research, 2008, vol. 36, No. 8.
Szafranska et al., MicroRNA expression alterations are linked to tumorigenesis and non-neoplastic processes in pancreatic ductal adenocarcinoma, Oncogene (2007) 26, 4442-4452.
Taganov et al., NF-kappaB-dependent induction of microRNA miR-146, an inhibitor targeted to signaling proteins of innate immune responses, Proc Natl Acad Sci USA, 2006, 103(33):12481-12486.
Tavazoie et al., Endogenous human microRNAs that suppress breast cancer metastasis, Nature. Jan. 10, 2008; 451(7175): 147-152.
Taylor et al., Binding of specific peroxidise-labeled antibody to placental-type alkaline phosphatase on tumor-derived membrane fragments, Cancer Res, 40, 1980, pp. 4064-4069.
Taylor et al., Characterization of Humoral Responses of Ovarian Cancer Patients: Antibody Subclasses and Antigenic Components, Gynecologic Oncology, vol. 116(2), 2010, pp. 213-221, Academic Press, London, GB.
Taylor et al., Identification of antigenic components recognized by membrane-bound antibodies from ovarian cancer patients, American Journal of Reproductive Immunology, vol. 6, No. 4, Dec. 1, 1984, pp. 179-184, Munksgaard International Publishers Copenhangen, OK.
Taylor et al., Isolation of plasma membrane fragments from cultured murine melanoma cells, Biochem Biophys Res Comm, 113, 1983, pp. 470-476.
Taylor et al., Patient-Derived Tumor-Reactive Antibodies as Diagnostic Markers for Ovarian Cancer, Gynecologic Oncology, vol. 115, No. 1, 2009, pp. 112-120, Academic Press, London, GB.
Taylor et al., Pregnancy-Associated Exosomes and Their Modulation ofT Cell Signaling, Journal of Immunology, American Association of Immunologists, US, vol. 176, No. 3, 2006, pp. 1534-1542.
Taylor et al., Pregnancy-linked suppression of TcR signaling pathways by a circulating factor absent in recurrent spontaneous pregnancy loss, Molecular Immunology, 43, 2006, pp. 1872-1880.
Taylor et al., Shed membrane fragment-associated markers for endometrial and ovarian cancers, Gynecol Oncol, 84, 2002, pp. 443-448.
Taylor et al., Shedding of plasma membrane fragments: Neoplastic and; developmental importance, Developmental Biology, (M. Steinberg, ed.), vol. 3, 1986, pp. 33-57.
Taylor et al., Tumour-derived exosomes and their role in cancer-associated T-cell signalling defects, Brit J Cancer, 92,2005, pp. 305-311.
Taylor, et al. Pregnancy-associated exosomes and their modulation of T cell signaling. J Immunol Feb. 1, 2006;176(3):1534-42.
Taylor, et al., Neoplastic and Developmental Importance of Shed Plasma Membrane Fragments, Amer. Zool. 1986,26, pp. 511-514.
Thery, et al., Exosomes: composition, biogenesis and function, Nature Reviews, Immunology, Aug. 2002, vol. 2, pp. 569-579.
Thiagarajan et al., beta2-Glycoprotein I Promotes the Binding of Anionic Phospholipid Vesicles by Macrophages, Arterioscler Thromb Vasc Biol. 1999;19:2807-2811.
Trubey, et al., Quantitation of HLA class II protein incorporated into human immunodeficiency type 1 virions purified by anti-CD45 immunoaffinity depletion of microvesicles, Journal of Virology, Dec. 2003, pp. 12699-12709; available at http://jvi.asm.org, accessed Dec. 17, 2011.
Tuschil et al., Expanding small RNA interference, Nat. Biotechnol., May 2002;20(5):446-8.
U.S. Appl. No. 12/677,931, Office Action dated Aug. 20, 2012.
U.S. Appl. No. 13/873,371, Nonfinal Office Action, dated Mar. 25, 2016.
Valadi, et al. Exosome-mediated transfer of mRNAs and microRNAs is a novel mechanism of genetic exchange between cells. Nature Cell Biology. 2007; 9(6):654-659.
Valenti et al., Tumor-Released Microvesicles as Vehicles of Immunosuppression, Cancer Res 2007;67:2912-2915.
Varnholt et al., MicroRNA Gene Expression Profile of Hepatitis C Virus-Associated Hepatocellular Carcinoma, Hepatology, vol. 47, No. 4, 2008, pp. 1223-1232.
Visone et al., MicroRNAs (miR)-221 and miR-222, both overexpressed in human thyroid papillary carcinomas, regulate p27Kip1 protein levels and cell cycle, Endocrine-Related Cancer (2007) 14 791-798.
Volinia et al., A microRNA expression signature of human solid tumors defines cancer gene targets, Proc Natl Acad Sci USA, 2006, 103(7):2257-2261.
Voorhoeve et al., Classifying microRNAs in cancer: the good, the bad and the ugly, Biochim Biophys Acta. Jun. 2007;1775(2):274-82.
Wang et al., A micro-RNA signature associated with race, tumor size, and target gene activity in human uterine leiomyomas, Genes Chromosomes Cancer. 2007 46(4):336-47.
Wang et al., MicroRNA miR-24 inhibits erythropoiesis by targeting activin type I receptor ALK4, Blood, 2008 111: 588-595.
Wang et al., The Expression of MicroRNA miR-107 Decreases Early in Alzheimer's Disease and May Accelerate Disease Progression through Regulation of beta-Site Amyloid Precursor Protein-Cleaving Enzyme 1, The Journal of Neuroscience, 2008; 28(5):1213-1223.
Wang et al., The Role of the NADPH Oxidase Complex, p38 MAPK, and Akt in Regulating Human Monocyte/Macrophage Survival, Am J Respir Cell Mol Biol vol. 36. pp. 68-77, 2007.
Wieckowski et al., Human tumor-derived vs dendritic cell-derived exosomes have distinct biologic roles and molecular profiles, Immunol Res. 2006;36(1-3):247-54, Abstract only.
Xu et al., The Drosophila MicroRNA Mir-14 Suppresses Cell Death and Is Required for Normal Fat Metabolism, Current Biology, vol. 13, 790-795, Apr. 29, 2003.
Yang et al., MicroRNA expression profiling in human ovarian cancer: miR-214 induces cell survival and cisplatin resistance by targeting PTEN, Cancer Res, 68, 2008, pp. 425-433.
Yu et al., The Regulation of Exosome Secretion: a Novel Function of the p53 Protein, Cancer Res, 66:(9), 2006, pp. 4795-4801.
Zanette et al., miRNA expression profiles in chronic lymphocytic and acute lymphocytic leukemia, Brazilian Journal of Medical and Biological Research (2007) 40: 1435-1440.
Zeng et al., Both Natural and Designed Micro RNAs Can Inhibit the Expression of Cognate mRNAs When Expressed in Human Cells, Molecular Cell, vol. 9, 1327-1333, 2002.
Zhang et al., microRNAs as oncogenes and tumor suppressors, Developmental Biology, 302, 2007, pp. 1-12.
Zhang et al., microRNAs exhibit high frequency genomic alterations in human cancer, Proc Natl Acad Sci USA, 103,2006, pp. 9136-9141.

* cited by examiner

| Table I |||| 
|---|---|---|---|
| Disease | Increased Expression in Disease Tissue | Decreased Expression in Disease Tissue | Reference |
| colon adenocarcinoma | miR-20a, miR-21, miR-106a, miR-181b, miR-203 | | JAMA. 2008 Jan 30; 299(4):425-36; Int J Cancer. 2008 Mar 1; 122(5):969-77. |
| Colorectal | miR-19a, miR-21 miR-127, miR-31, miR-96, miR-135b and miR-183, | miR-30c, miR-133a, miR-143,miR-133b and miR-145 | Int J Cancer. 2008 Mar 1; 122(5):969-77; Cancer. 2006 Jul 19; 5:29; Braz J Med Biol Res. 2007 Nov; 40(11):1435-40. |
| Prostate Cancer | miR-21 | miR-15a, miR-16-1, miR-143, miR-145 | Int J Cancer. 2008 Mar 1; 122(5):969-77. |
| Lung Cancer | mir-17-92, miR-19a, miR-21, miR-92, miR-155, miR-191, miR-205, miR-miR-210 | miR-let-7 | Int J Cancer. 2008 Mar 1; 122(5):969-77. |
| Breast cancer | miR-21, miR-155 | miR-125b, miR-145 | Int J Cancer. 2008 Mar 1; 122(5):969-77. |
| B-Cell lymphoma | miR-155, miR-17-92, miR-19a, miR-92, miR-142, miR- 155, miR-221 | | Int J Cancer. 2008 Mar 1;122 (5):969-77. |
| Pancreatic | miR-103 and miR-107, miR-18a, miR-31, miR-93, miR-221 and miR-224, miR-155 | miR-133a, miR-216, miR 217 | J Clin Oncol. 2006 Oct 10; 24(29):4677-84; Oncogene. 2007 Jun 28;26(30):4442-52 |
| Diffuse large BCL | miR-155, miR-17-92 | | Int J Cancer. 2008 Mar 1;122 (5):969-77. |
| CLL | miR-23b, miR-24-1, miR-146, miR-155, miR-195, miR-221, miR-331, miR-29a, miR-195, miR-34a, and miR-29c | miR-15a, miR-16-1, miR-29, miR-223 | Int J Cancer. 2008 Mar 1;122 (5):969-77; Braz J Med Biol Res. 2007 Nov;40(11):1435-40. |
| Bladder cancer | miR-223, miR-26b, miR-221, miR-103-1, miR-185, miR-23b, miR-203, miR-17-5p, miR-23a, and miR-205 | | Urol Oncol. 2007 Sep-Oct;25(5):387-92 |
| Renal Cancer | miR-28, miR-185, miR-27, and miR-let-7f-2 | | Urol Oncol. 2007 Sep-Oct;25(5):387-92 |
| Hypoxia-tumor | miR-23, miR-24, miR-26, miR-27, miR-103, miR-107, miR-181, miR-210, and miR-213 | | Mol Cell Biol. 2007 Mar; 27(5):1859-67. |
| uterine leiomyomas | miR-let-7 family, miR-21, miR-23b, miR-29b, and miR-197 | | Genes Chromosomes Cancer. 2007 Apr;46(4):336-47 |
| ovarian | miR-199*, miR-200a, miR-214 | miR-100, miR- let-7 cluster, miR-125b | Cancer Res. 2008 Jan 15;68(2):425-33 |
| hepatitis C virus-associated hepatocellular carcinoma. | miR-122, miR-100, and miR-10a | miR-198 and miR-145 | Hepatology. 2007 Dec 19 [Epub ahead of print |
| ALL | miR-128b, miR-204, miR-218, miR-331, and miR-181b-1, miR-17-92 | | Braz J Med Biol Res. 2007 Nov; 40(11):1435-40. |
| Alzheimer's disease | miR-9, miR-128 | miR-107 | J Neurosci. 2008 Jan 30; 28(5):1213-23 Neuroreport. 2007 Feb 12;18(3):297-300 |
| myelofibrosis | miR-190 | miR-31, miR-150, and miR-95 | Exp Hematol. 2007 Nov;35(11):1708-18 |
| myelofibrosis, polycythemia vera, thrombocythemia | | miR-34a, -342, -326, -105, -149, and -147 | Exp Hematol. 2007 Nov;35(11):1708-18 |
| HIV | miR-29a, miR-29b, miR-149, miR-378, miR-324-5p | | Biochem Biophys Res Commun. 2005 Dec 2; 337(4):1214-8. |
| HIV-1 latency | miR-28, miR-125b, miR-150, miR-223 and miR-382 | | Nat Med. 2007 Oct; 13(10):1241-7. |

FIG. 6 – Table I

Table II

| Expressed Plasma miRNAs after filtering | | Detector Name Undetectable | | | |
|---|---|---|---|---|---|
| Detector_Name | filter | | | | |
| hsa-let-7a | 0.333333333 | hsa-let-7e | hsa-mir-346 | hsa-mir-520c | hsa-mir-629 |
| hsa-let-7b | 0.058823529 | hsa-mir-001 | hsa-mir-362 | hsa-mir-520d | hsa-mir-630 |
| hsa-let-7c | 0.725490196 | hsa-mir-007 | hsa-mir-363 | hsa-mir-520d* | hsa-mir-631 |
| hsa-let-7d | 0.529411765 | hsa-mir-009 | hsa-mir-363* | hsa-mir-520e | hsa-mir-632 |
| hsa-let-7f | 0.745098039 | hsa-mir-009* | hsa-mir-365 | hsa-mir-520f | hsa-mir-633 |
| hsa-let-7g | 0.215686275 | hsa-mir-010a | hsa-mir-367 | hsa-mir-520g | hsa-mir-634 |
| hsa-mir-015a | 0.568627451 | hsa-mir-010b | hsa-mir-368 | hsa-mir-520h | hsa-mir-635 |
| hsa-mir-015b | 0.078431373 | | hsa-mir-369-3p | hsa-mir-521 | hsa-mir-636 |
| hsa-mir-016 | 0 | hsa-mir-017-3p | hsa-mir-369-5p | hsa-mir-522 | hsa-mir-637 |
| hsa-mir-017-5p | 0.117647059 | hsa-mir-018b | hsa-mir-371 | hsa-mir-523 | hsa-mir-638 |
| hsa-mir-018a | 0.784313726 | hsa-mir-022 | hsa-mir-372 | hsa-mir-524 | hsa-mir-639 |
| hsa-mir-018a* | 0.784313726 | hsa-mir-023a | hsa-mir-373 | hsa-mir-525 | hsa-mir-641 |
| hsa-mir-019a | 0.176470588 | hsa-mir-023b | hsa-mir-373* | hsa-mir-525* | hsa-mir-642 |
| hsa-mir-019b | 0.058823529 | hsa-mir-028 | hsa-mir-375 | hsa-mir-526a | |
| hsa-mir-020a | 0 | hsa-mir-029b | hsa-mir-376a* | hsa-mir-526b | hsa-mir-644 |
| hsa-mir-020b | 0.37254902 | hsa-mir-029c | hsa-mir-376b | hsa-mir-526b* | hsa-mir-645 |
| hsa-mir-021 | 0.411764706 | hsa-mir-031 | hsa-mir-377 | hsa-mir-526c | hsa-mir-646 |
| hsa-mir-024 | 0 | hsa-mir-033 | hsa-mir-378 | hsa-mir-527 | hsa-mir-647 |
| hsa-mir-025 | 0.647058824 | hsa-mir-034a | hsa-mir-379 | | hsa-mir-648 |
| hsa-mir-026a | 0 | hsa-mir-034b | hsa-mir-380-3p | | hsa-mir-649 |
| hsa-mir-026b | 0.176470588 | hsa-mir-034c | hsa-mir-380-5p | hsa-mir-542-3p | hsa-mir-650 |
| hsa-mir-027a | 0.254901961 | hsa-mir-095 | hsa-mir-381 | hsa-mir-542-5p | hsa-mir-651 |
| hsa-mir-027b | 0.352941177 | hsa-mir-099a | hsa-mir-383 | hsa-mir-544 | hsa-mir-652 |
| hsa-mir-029a | 0.764705882 | hsa-mir-100 | hsa-mir-409-5p | hsa-mir-545 | hsa-mir-653 |
| hsa-mir-030a-3p | 0.37254902 | hsa-mir-101 | hsa-mir-410 | hsa-mir-548a | hsa-mir-654 |
| hsa-mir-030a-5p | 0.098039216 | hsa-mir-105 | hsa-mir-412 | hsa-mir-548b | hsa-mir-655 |
| hsa-mir-030b | 0.039215686 | hsa-mir-107 | hsa-mir-422a | hsa-mir-548c | hsa-mir-656 |
| hsa-mir-030c | 0.019607843 | hsa-mir-122a | hsa-mir-422b | hsa-mir-548d | hsa-mir-657 |
| hsa-mir-030d | 0.274509804 | hsa-mir-124a | hsa-mir-424 | hsa-mir-549 | hsa-mir-658 |
| hsa-mir-032 | 0 | hsa-mir-125b | hsa-mir-429 | hsa-mir-550 | hsa-mir-659 |
| hsa-mir-092 | 0 | hsa-mir-126 | hsa-mir-432* | hsa-mir-551a | hsa-mir-660 |
| hsa-mir-093 | 0.058823529 | hsa-mir-128a | hsa-mir-448 | hsa-mir-551b | hsa-mir-661 |
| hsa-mir-096 | 0 | hsa-mir-128b | hsa-mir-449 | hsa-mir-552 | hsa-mir-662 |
| hsa-mir-098 | 0.784313726 | hsa-mir-129 | hsa-mir-449b | hsa-mir-553 | |
| hsa-mir-099b | 0.549019608 | hsa-mir-133a | hsa-mir-450 | hsa-mir-554 | |

FIG. 7 – Table II

| | | | | |
|---|---|---|---|---|
| hsa-mir-103 | 0.235294118 | hsa-mir-135a | hsa-mir-451 | hsa-mir-555 |
| hsa-mir-106a | 0.058823529 | hsa-mir-135b | hsa-mir-452 | hsa-mir-556 |
| hsa-mir-106b | 0.215686275 | hsa-mir-136 | hsa-mir-452* | hsa-mir-557 |
| hsa-mir-125a | 0.078431373 | hsa-mir-137 | hsa-mir-453 | hsa-mir-558 |
| hsa-mir-126 | 0 | hsa-mir-138 | hsa-mir-455 | hsa-mir-559 |
| hsa-mir-126* | 0.117647059 | hsa-mir-139 | hsa-mir-483 | hsa-mir-561 |
| hsa-mir-127 | 0.176470588 | hsa-mir-141 | hsa-mir-485-5p | hsa-mir-562 |
| hsa-mir-130a | 0.666666667 | hsa-mir-143 | hsa-mir-487a | hsa-mir-563 |
| hsa-mir-130b | 0.705882353 | hsa-mir-147 | hsa-mir-488 | hsa-mir-564 |
| hsa-mir-132 | 0.705882353 | hsa-mir-148a | hsa-mir-489 | hsa-mir-565 |
| hsa-mir-133b | 0.529411765 | hsa-mir-149 | hsa-mir-491 | hsa-mir-566 |
| hsa-mir-134 | 0.235294118 | hsa-mir-152 | hsa-mir-492 | hsa-mir-567 |
| hsa-mir-140 | 0.078431373 | hsa-mir-153 | hsa-mir-493-3p | hsa-mir-569 |
| hsa-mir-142-3p | 0.196078431 | hsa-mir-154 | hsa-mir-493-5p | hsa-mir-570 |
| hsa-mir-142-5p | 0.254901961 | hsa-mir-154* | hsa-mir-494 | hsa-mir-571 |
| hsa-mir-145 | 0.705882353 | hsa-mir-181a | hsa-mir-495 | hsa-mir-572 |
| hsa-mir-146a | 0 | hsa-mir-181a* | hsa-mir-496 | hsa-mir-573 |
| hsa-mir-146b | 0.078431373 | hsa-mir-181c | hsa-mir-497 | |
| hsa-mir-148b | 0.784313726 | hsa-mir-182 | hsa-mir-498 | hsa-mir-575 |
| hsa-mir-150 | 0.019607843 | hsa-mir-184 | hsa-mir-499 | hsa-mir-576 |
| hsa-mir-151 | 0.019607843 | hsa-mir-185 | hsa-mir-500 | hsa-mir-578 |
| hsa-mir-155 | 0.176470588 | hsa-mir-187 | hsa-mir-501 | hsa-mir-579 |
| hsa-mir-181d | 0.725490196 | hsa-mir-189 | hsa-mir-502 | hsa-mir-580 |
| hsa-mir-182* | 0.196078431 | hsa-mir-190 | hsa-mir-503 | hsa-mir-583 |
| hsa-mir-183 | 0.058823529 | hsa-mir-192 | hsa-mir-504 | |
| hsa-mir-186 | 0.039215686 | hsa-mir-193b | hsa-mir-505 | hsa-mir-585 |
| hsa-mir-191 | 0 | hsa-mir-194 | hsa-mir-506 | hsa-mir-586 |
| hsa-mir-193a | 0.666666667 | hsa-mir-196a | hsa-mir-507 | hsa-mir-587 |
| hsa-mir-195 | 0.31372549 | hsa-mir-198 | hsa-mir-508 | hsa-mir-588 |
| hsa-mir-196b | 0.254901961 | hsa-mir-199a | hsa-mir-509 | hsa-mir-589 |
| hsa-mir-197 | 0.019607843 | hsa-mir-199b | hsa-mir-510 | hsa-mir-591 |
| hsa-mir-199a* | 0.254901961 | hsa-mir-200a | hsa-mir-511 | hsa-mir-592 |
| hsa-mir-221 | 0.784313726 | hsa-mir-200a* | hsa-mir-512-3p | hsa-mir-593 |
| hsa-mir-222 | 0 | hsa-mir-200b | hsa-mir-512-5p | hsa-mir-594 |
| hsa-mir-223 | 0 | hsa-mir-200c | hsa-mir-513 | hsa-mir-596 |
| hsa-mir-224 | 0.529411765 | hsa-mir-202 | hsa-mir-514 | hsa-mir-597 |
| hsa-mir-302b | 0.078431373 | hsa-mir-202* | hsa-mir-515-3p | hsa-mir-599 |
| hsa-mir-320 | 0.098039216 | hsa-mir-203 | hsa-mir-515-5p | hsa-mir-600 |
| hsa-mir-324-3p | 0.705882353 | hsa-mir-204 | hsa-mir-516-5p | hsa-mir-601 |
| hsa-mir-324-5p | 0.470588235 | hsa-mir-205 | hsa-mir-517* | hsa-mir-603 |
| hsa-mir-328 | 0 | hsa-mir-206 | hsa-mir-517a | hsa-mir-604 |

FIG. 7 – Table II (cont)

| | | | | |
|---|---|---|---|---|
| hsa-mir-330 | 0.666666667 | hsa-mir-208 | hsa-mir-517b | hsa-mir-606 |
| hsa-mir-331 | 0.039215686 | hsa-mir-210 | hsa-mir-517c | hsa-mir-607 |
| hsa-mir-335 | 0.725490196 | hsa-mir-211 | hsa-mir-518a | hsa-mir-608 |
| hsa-mir-339 | 0.607843137 | hsa-mir-214 | hsa-mir-518b | hsa-mir-609 |
| hsa-mir-340 | 0.529411765 | hsa-mir-215 | hsa-mir-518c | hsa-mir-610 |
| hsa-mir-342 | 0.019607843 | hsa-mir-216 | hsa-mir-518c* | hsa-mir-612 |
| hsa-mir-345 | 0.705882353 | hsa-mir-217 | hsa-mir-518d | hsa-mir-613 |
| hsa-mir-361 | 0.725490196 | hsa-mir-218 | hsa-mir-518e | hsa-mir-614 |
| hsa-mir-370 | 0.549019608 | hsa-mir-219 | hsa-mir-518f | hsa-mir-615 |
| hsa-mir-374 | 0.37254902 | hsa-mir-220 | hsa-mir-519a | hsa-mir-616 |
| hsa-mir-376a | 0.450980392 | hsa-mir-296 | hsa-mir-519b | hsa-mir-617 |
| hsa-mir-382 | 0.607843137 | hsa-mir-299-3p | hsa-mir-519c | hsa-mir-618 |
| hsa-mir-411 | 0.607843137 | hsa-mir-299-5p | hsa-mir-519d | hsa-mir-619 |
| hsa-mir-423 | 0.215686275 | hsa-mir-301 | hsa-mir-519e | hsa-mir-621 |
| hsa-mir-425-3p | 0.31372549 | hsa-mir-302a | hsa-mir-519e* | hsa-mir-622 |
| hsa-mir-425-5p | 0.215686275 | hsa-mir-302a* | hsa-mir-520a | hsa-mir-624 |
| hsa-mir-432 | 0.392156863 | hsa-mir-302b* | hsa-mir-520a* | hsa-mir-626 |
| hsa-mir-433 | 0.470588235 | hsa-mir-302c | hsa-mir-520b | hsa-mir-627 |
| hsa-mir-484 | 0 | hsa-mir-302c* | | |
| hsa-mir-485-3p | 0.31372549 | hsa-mir-302d | | |
| hsa-mir-486 | 0 | hsa-mir-323 | | |
| hsa-mir-487b | 0.529411765 | hsa-mir-325 | | |
| hsa-mir-532 | 0.62745098 | hsa-mir-326 | | |
| hsa-mir-539 | 0.588235294 | hsa-mir-329 | | |
| hsa-mir-574 | 0 | hsa-mir-337 | | |
| hsa-mir-584 | 0.784313726 | hsa-mir-338 | | |
| hsa-mir-628 | 0 | | | |
| hsa-mir-643 | 0.568627451 | | | |

FIG. 7 – Table II (cont)

| Table III. Top ten expressed miRNAs in plasma microvesicles and PBMC. | | | | | | | |
|---|---|---|---|---|---|---|---|
| Plasma Microvesicles | | | | PBMC | | | |
| miRNA | Normalized Expression (±S.D.) | Frequency expressed among donors (%) | Top ten ranking frequency (%) | miRNA | Normalized Expression (±S.D.) | Frequency expressed among donors (%) | Top ten ranking frequency (%) |
| mir-223 | 1589 ± 653 | 100 | 100 | mir-223 | 2143 ± 499 | 100 | 100 |
| mir-484 | 50.9± 22.9 | 100 | 96 | mir-150 | 241 ± 94.6 | 98 | 98 |
| mir-191 | 46.4± 14.9 | 100 | 100 | mir-146b | 57.5± 21.1 | 100 | 100 |
| mir-146a | 39.5 ± 19 | 100 | 88 | mir-016 | 54.7 ± 32.9 | 100 | 100 |
| mir-016 | 25.4 ± 13.3 | 100 | 78 | mir-484 | 40.6 ± 18.8 | 89 | 88 |
| mir-026a | 25.2± 9.95 | 100 | 90 | mir-146a | 39.6 ± 13.0 | 100 | 98 |
| mir-222 | 24.5 ± 12.4 | 100 | 76 | mir-191 | 32.4 ± 15.6 | 100 | 94 |
| mir-024 | 22.7 ± 10.5 | 100 | 80 | mir-026a | 30 ± 8.92 | 100 | 100 |
| mir-126 | 18.2 ± 8.04 | 100 | 66 | mir-019b | 21.7 ± 7.49 | 100 | 80 |
| mir-032 | 15.3 ±32.6 | 100 | 31 | mir-020a | 15± 5.11 | 100 | 4 |

FIG. 8 – Table III

| Predicted pathways regulated by miRNAs expressed in the plasma microvesicles and PBMC fractions based on IPA analysis of only Sanger miRBase predicted targets. | | | |
|---|---|---|---|
| Plasma Microvesicles | p-value | PBMC | p-value |
| glycerophospholipid metabolism | 3.29E-03 | axonal guidance signaling | 1.47E-02 |
| inositol phosphate metabolism | 5.77E-03 | synaptic long-term potentiation | 2.07E-02 |
| phospholipid degradation | 9.17E-03 | estrogen receptor signaling | 2.23E-02 |
| alanine and aspartate metabolism | 1.96E-02 | glycerophospholipid metabolism | 2.45E-02 |
| estrogen receptor signaling | 2.14E-02 | D-glutamine and D-glutamate metabolism | 2.78E-02 |
| Predicted pathways regulated by miRNAs expressed in the plasma microvesicles and PBMC fractions from combined targets of TargetScan and Sanger mirBase. | | | |
| Plasma Microvesicles | p-value | PBMC | p-value |
| Antigen Presentation Pathway | 1.28E-03 | Glycine, Serine, Threonine Metabolism | 3.63E-03 |
| Glycerophospholipid Metabolism | 9.05E-03 | Glycerophospholipid Metabolism | 2.38E-02 |
| Glycine, Serine, Threonine Metabolism | 1.56E-02 | D-Glutamine, D-Glutamate Metabolism | 2.54E-02 |
| Natural Killer Cell Signaling | 1.57E-02 | Glyoxylate, Dicarboxylate Metabolism | 4.37E-02 |

FIG. 9- Table IV plasma_mean is the average of the raw Ct across all 51 observations for plasma
PBMC_mean is the average of the raw Ct across all 51 observations for PBMC
"Plasma-PBMC" is the difference of normalized data between plasma and PBMC
Plasma-MNC "+": miR level is higher in PBMC, and "---" :miR level is lower in plasma
"foldchange" is 2^the difference. For miR 29a: 40.3=2^(5.33). Which means that the miR level in PBMC is 40 times higher than that in serum
"p-value" was considered as significant if p-value<0.05/72=0.0006

| Detector_Name | Plasma_mean | PBMC_mean | Plasma-MNC | foldchange | p-value | Fold Change for Plasma |
|---|---|---|---|---|---|---|
| hsa-mir-029a | 37.12771586 | 31.87566924 | 5.3333 | 40.31654208 | 9.70E-28 | 0.024803715 |
| 18S (CT) | 12.71460766 | 9.451029281 | 3.3449 | 10.16050356 | 9.84E-25 | 0.098420319 |
| hsa-mir-155 | 32.77301951 | 29.64446324 | 3.2098 | 9.252222752 | 6.61E-23 | 0.108082136 |
| hsa-mir-146b | 30.87718855 | 26.44380422 | 4.5147 | 22.85915231 | 1.81E-22 | 0.043746154 |
| hsa-mir-142-3p | 33.45027482 | 28.97701498 | 4.5545 | 23.49855274 | 1.91E-22 | 0.042555812 |
| hsa-mir-222 | 27.69255453 | 29.77206378 | -1.9982 | 0.250312111 | 1.18E-21 | 3.995012452 |
| hsa-mir-328 | 30.15998382 | 32.9642692 | -2.723 | 0.151459083 | 1.64E-21 | 6.602443268 |
| hsa-mir-151 | 30.40933518 | 32.29093225 | -1.8003 | 0.287114879 | 2.24E-21 | 3.482926432 |
| hsa-mir-150 | 30.47592494 | 24.6518619 | 5.9053 | 59.93388544 | 7.01E-21 | 0.016685052 |
| hsa-mir-486 | 28.73173943 | 31.56628224 | -2.7533 | 0.148311256 | 4.31E-20 | 6.74257657 |
| hsa-mir-197 | 30.22004439 | 32.22121169 | -1.9199 | 0.264272828 | 5.34E-18 | 3.783968293 |
| hsa-mir-140 | 30.80686384 | 28.81119314 | 2.077 | 4.219289268 | 2.87E-17 | 0.237006741 |
| hsa-mir-320 | 32.3865371 | 33.86695527 | -1.3991 | 0.379165604 | 1.63E-16 | 2.637370031 |
| hsa-mir-374 | 34.51049488 | 32.67750663 | 1.9143 | 3.76930882 | 8.01E-15 | 0.265300629 |
| hsa-mir-019a | 32.11311761 | 29.96710463 | 2.2273 | 4.682568177 | 2.86E-12 | 0.213558022 |
| hsa-mir-019b | 29.4539469 | 27.85115537 | 1.6841 | 3.213398715 | 7.12E-12 | 0.311196988 |
| hsa-mir-126 | 28.07632355 | 29.10031739 | -0.9427 | 0.520258307 | 2.61E-11 | 1.922122121 |
| hsa-mir-016 | 27.74576263 | 26.5689361 | 1.2581 | 2.391805375 | 1.35E-10 | 0.418094219 |
| hsa-mir-532 | 36.36702118 | 34.20639555 | 2.2419 | 4.730196117 | 6.15E-10 | 0.211407725 |
| hsa-mir-092 | 29.75216725 | 30.55396618 | -0.7205 | 0.606887075 | 1.17E-09 | 1.647753003 |
| hsa-mir-199a* | 33.58726049 | 35.4571252 | -1.7886 | 0.289452796 | 3.21E-09 | 3.454794744 |
| hsa-let-7g | 33.60687451 | 31.98889118 | 1.6993 | 3.247433539 | 4.99E-09 | 0.307935478 |
| hsa-mir-032 | 29.54416735 | 31.80526606 | -2.1798 | 0.220706343 | 8.52E-09 | 4.530907381 |
| hsa-mir-345 | 36.51374094 | 34.71916814 | 1.8759 | 3.670305114 | 1.26E-08 | 0.272456913 |
| hsa-mir-103 | 33.43298386 | 34.64525506 | -1.131 | 0.456599125 | 1.99E-08 | 2.190104942 |
| hsa-mir-021 | 34.3396759 | 32.34668429 | 2.0743 | 4.211400264 | 4.23E-08 | 0.237450714 |
| hsa-mir-183 | 32.45422284 | 35.11564953 | -2.5801 | 0.167229352 | 7.17E-08 | 5.979811469 |
| hsa-mir-142-5p | 33.80914806 | 32.4729949 | 1.4174 | 2.671037073 | 9.83E-08 | 0.374386417 |
| hsa-mir-017-5p | 31.31194325 | 32.41959375 | -1.0264 | 0.490933663 | 1.26E-07 | 2.03693508 |
| hsa-mir-106b | 33.74281576 | 32.50763722 | 1.3165 | 2.490611501 | 1.28E-07 | 0.401507822 |
| hsa-mir-342 | 30.04861659 | 29.34785373 | 0.782 | 1.719512972 | 3.06E-07 | 0.581560021 |

FIG. 10 – Table V

| | | | | | | |
|---|---|---|---|---|---|---|
| hsa-mir-015a | 36.02643541 | 34.41777394 | 1.6899 | 3.226343396 | 3.25E-07 | 0.309948408 |
| hsa-mir-106a | 32.27341998 | 33.310393 | -0.9557 | 0.515591362 | 4.92E-07 | 1.939520467 |
| hsa-mir-030a-5p | 32.84903206 | 32.11457514 | 0.8157 | 1.760151976 | 4.98E-07 | 0.56813276 |
| hsa-mir-181d | 36.91248884 | 35.10117465 | 1.8926 | 3.713037794 | 5.30E-07 | 0.269321255 |
| hsa-mir-574 | 29.77877718 | 31.99443544 | -2.1344 | 0.227762162 | 3.05E-06 | 4.390544899 |
| hsa-mir-020a | 29.10969835 | 28.36665692 | 0.8243 | 1.770675693 | 3.74E-06 | 0.564756157 |
| hsa-mir-133b | 35.04172861 | 36.86655569 | -1.7435 | 0.298644281 | 4.05E-06 | 3.348465259 |
| hsa-let-7b | 32.39289143 | 33.23120741 | -0.757 | 0.591725511 | 4.25E-06 | 1.689972769 |
| hsa-mir-026b | 32.29385324 | 31.16910598 | 1.206 | 2.30697121 | 5.44E-06 | 0.433468782 |
| hsa-mir-027b | 34.97319163 | 37.12771071 | -2.0732 | 0.23763183 | 1.20999E-05 | 4.208190455 |
| hsa-mir-223 | 21.63665394 | 21.16179467 | 0.5561 | 1.470289246 | 2.99379E-05 | 0.680138281 |
| hsa-mir-195 | 33.54064118 | 32.45677802 | 1.1652 | 2.242643031 | 0.000055077 | 0.44590244 |
| hsa-mir-024 | 27.78702461 | 28.36258525 | -0.4943 | 0.709906043 | 0.000137267 | 1.408637114 |
| hsa-mir-030d | 33.8831652 | 32.98623929 | 0.9782 | 1.970005968 | 0.000154741 | 0.507612675 |
| hsa-mir-015b | 31.44832671 | 32.07442065 | -0.5448 | 0.685486424 | 0.000371404 | 1.458818095 |
| hsa-mir-096 | 31.46980261 | 32.73422363 | -1.1831 | 0.44040416 | 0.000386324 | 2.270641588 |
| hsa-mir-191 | 26.63890682 | 27.27556098 | -0.7068 | 0.612677595 | 0.00047708 | 1.632179808 |
| hsa-mir-425-3p | 34.77417378 | 35.82356186 | -0.9681 | 0.511178832 | 0.00084906 | 1.95626254 |
| hsa-mir-020b | 34.97815304 | 33.84422814 | 1.2152 | 2.321729667 | 0.000852341 | 0.430713366 |
| hsa-mir-643 | 35.6734501 | 37.16658316 | -1.4118 | 0.375842469 | 0.00130314 | 2.660689207 |
| hsa-mir-126* | 31.16681945 | 32.1345669 | -0.8865 | 0.54092482 | 0.001314585 | 1.84868574 |
| hsa-mir-423 | 33.93739253 | 34.82278949 | -0.8041 | 0.57271925 | 0.001362239 | 1.746056205 |
| hsa-mir-425-5p | 33.23637712 | 33.88098071 | -0.5633 | 0.676752398 | 0.00179719 | 1.477645299 |
| hsa-mir-026a | 27.61150875 | 27.32677761 | 0.366 | 1.28877463 | 0.003310506 | 0.775930854 |
| hsa-mir-302b | 33.23113157 | 34.33434284 | -1.0219 | 0.492467356 | 0.003731969 | 2.030591447 |
| hsa-mir-484 | 26.55751618 | 28.13046808 | -1.4917 | 0.355593289 | 0.009046242 | 2.812201558 |
| hsa-mir-125a | 30.94104939 | 31.63410639 | -0.6118 | 0.654379746 | 0.02785181 | 1.528164657 |
| hsa-let-7a | 34.16573733 | 34.66154112 | -0.4145 | 0.750279477 | 0.031855987 | 1.332836671 |
| hsa-mir-628 | 33.65892745 | 34.23451988 | -0.4943 | 0.709906043 | 0.033363855 | 1.408637114 |
| hsa-mir-182* | 34.51246341 | 35.19580641 | -0.6021 | 0.65879431 | 0.04206113 | 1.517924464 |
| hsa-mir-093 | 29.92991163 | 30.33080725 | -0.3196 | 0.801292012 | 0.043597802 | 1.247984486 |
| hsa-mir-376a | 35.49479343 | 36.2218518 | -0.6458 | 0.639138279 | 0.048003434 | 1.564606648 |
| hsa-mir-196b | 33.89190492 | 34.56216867 | -0.589 | 0.664803554 | 0.052904716 | 1.504203751 |
| hsa-mir-025 | 36.27231106 | 35.85259422 | 0.501 | 1.41519416 | 0.069149461 | 0.706616822 |
| hsa-mir-027a | 33.33901471 | 32.99540369 | 0.4249 | 1.342479446 | 0.101287776 | 0.744890362 |
| hsa-mir-146a | 27.051654 | 26.95885476 | 0.1741 | 1.12826034 | 0.241458101 | 0.886320262 |
| hsa-mir-340 | 35.71472961 | 35.53800265 | 0.258 | 1.195819797 | 0.297093531 | 0.8362464 |
| hsa-mir-030b | 30.55810765 | 30.72009382 | -0.0807 | 0.945598728 | 0.389875101 | 1.057531033 |
| hsa-mir-186 | 31.31177086 | 31.45367741 | -0.06062 | 0.958851963 | 0.659198081 | 1.042913858 |
| hsa-mir-331 | 31.20308243 | 31.25979306 | 0.02458 | 1.017183525 | 0.843135202 | 0.983106761 |
| hsa-mir-030c | 30.93719829 | 31.01586004 | 0.002625 | 1.001821168 | 0.97816881 | 0.998182143 |

FIG. 10 – Table V (cont)

| Table VI | | | | | |
|---|---|---|---|---|---|
| detector_name | Average Normalized Expression PBMC | PBMC Standard deviation | detector_name | Average Normalized Expression Plasma | Plasma Standard deviation |
| hsa-mir-223 | 2143.797514 | 499.6723532 | hsa-mir-223 | 1589.265353 | 653.1441 |
| hsa-mir-150 | 241.3339986 | 94.6316509 | hsa-mir-484 | 50.93154102 | 22.91411 |
| hsa-mir-146b | 57.51515588 | 21.17347322 | hsa-mir-191 | 46.44422571 | 14.98219 |
| hsa-mir-016 | 54.79023342 | 32.92864759 | hsa-mir-146a | 39.5631478 | 19.02017 |
| hsa-mir-484 | 40.62828652 | 18.89513879 | hsa-mir-016 | 25.45043823 | 13.32435 |
| hsa-mir-146a | 39.66536453 | 13.01422255 | hsa-mir-026a | 25.2068328 | 9.956682 |
| hsa-mir-191 | 32.44104295 | 15.62493155 | hsa-mir-222 | 24.51626706 | 12.42177 |
| hsa-mir-026a | 30.05789737 | 8.928309461 | hsa-mir-024 | 22.79169634 | 10.53596 |
| hsa-mir-019b | 21.72111133 | 7.496587814 | hsa-mir-126 | 18.20923598 | 8.04666 |
| hsa-mir-020a | 15.03972998 | 5.117918017 | hsa-mir-032 | 15.32305403 | 32.61654 |
| hsa-mir-024 | 14.49037987 | 2.924884427 | hsa-mir-486 | 12.89548349 | 11.97428 |
| hsa-mir-142-3p | 11.61802275 | 7.535807778 | hsa-mir-020a | 10.12067658 | 5.597534 |
| hsa-mir-140 | 11.15286241 | 3.933184767 | hsa-mir-019b | 9.158209689 | 6.76422 |
| hsa-mir-126 | 9.209558485 | 3.825687483 | hsa-mir-150 | 8.165508668 | 25.08223 |
| hsa-mir-342 | 7.803100549 | 3.388772813 | hsa-mir-574 | 5.939301367 | 3.722014 |
| hsa-mir-155 | 6.584151232 | 4.579272166 | hsa-mir-092 | 5.700980896 | 3.157407 |
| hsa-mir-222 | 5.715723219 | 2.105344287 | hsa-mir-093 | 5.436799962 | 2.417329 |
| hsa-mir-019a | 5.53562668 | 2.957936571 | hsa-mir-342 | 5.114543492 | 3.297305 |
| hsa-mir-093 | 3.756090874 | 1.000518353 | hsa-mir-197 | 4.9808586 | 4.507 |
| hsa-mir-092 | 3.215354275 | 0.85390195 | hsa-mir-328 | 4.707858075 | 3.592588 |
| hsa-mir-486 | 3.096228853 | 7.676887526 | hsa-mir-096 | 3.674085488 | 5.965292 |
| hsa-mir-030b | 2.865611791 | 0.76538861 | hsa-mir-151 | 3.452172299 | 1.08377 |
| hsa-mir-574 | 2.458205492 | 1.894539696 | hsa-mir-146b | 3.272000368 | 2.101495 |
| hsa-mir-030c | 2.335820956 | 0.663949738 | hsa-mir-140 | 3.196516876 | 1.71678 |
| hsa-mir-026b | 2.129402092 | 0.705755408 | hsa-mir-030b | 3.134519745 | 1.142809 |
| hsa-mir-331 | 1.985929854 | 0.609153141 | hsa-mir-125a | 3.080410769 | 1.975409 |
| hsa-mir-125a | 1.808127477 | 1.087896802 | hsa-mir-126* | 3.023376204 | 2.068206 |
| hsa-mir-186 | 1.720577641 | 0.419612713 | hsa-mir-183 | 2.854264163 | 6.494415 |
| hsa-mir-032 | 1.716467503 | 1.338128537 | hsa-mir-030c | 2.412532336 | 0.863587 |
| hsa-mir-029a | 1.323099465 | 0.533548819 | hsa-mir-017-5p | 2.13024101 | 0.998316 |
| hsa-mir-126* | 1.269368187 | 0.759421276 | hsa-mir-331 | 2.087433557 | 0.81255 |
| hsa-let-7g | 1.199246639 | 0.349725473 | hsa-mir-186 | 2.022411766 | 0.916917 |
| hsa-mir-021 | 1.161213483 | 0.674584117 | hsa-mir-015b | 1.808314178 | 0.81048 |
| hsa-mir-197 | 1.149407136 | 0.647186919 | hsa-mir-019a | 1.697172987 | 1.453897 |

FIG. 11 – Table VI

| | | | | | |
|---|---|---|---|---|---|
| hsa-mir-015b | 1.14628446 | 0.432407565 | hsa-mir-302b | 1.339313335 | 2.387044 |
| hsa-mir-030a-5p | 1.094683149 | 0.306485271 | hsa-mir-026b | 1.292369054 | 0.824158 |
| hsa-mir-195 | 1.017673959 | 0.797387672 | hsa-mir-106a | 1.186157531 | 1.293289 |
| hsa-mir-151 | 1.007960478 | 0.397967603 | hsa-let-7b | 0.97666637 | 0.625536 |
| hsa-mir-142-5p | 0.962665368 | 0.492490733 | hsa-mir-320 | 0.911092198 | 0.420503 |
| hsa-mir-017-5p | 0.941159371 | 0.360846484 | hsa-mir-155 | 0.808867743 | 0.52866 |
| hsa-mir-106b | 0.910164376 | 0.403715009 | hsa-mir-030a-5p | 0.727538734 | 0.549257 |
| hsa-mir-096 | 0.875989336 | 0.559638262 | hsa-mir-628 | 0.713396354 | 1.263219 |
| hsa-mir-374 | 0.764917256 | 0.274388929 | hsa-mir-027a | 0.641903058 | 0.448917 |
| hsa-mir-328 | 0.720096352 | 0.412158586 | hsa-mir-142-3p | 0.627217683 | 0.607184 |
| hsa-mir-030d | 0.662654685 | 0.22361572 | hsa-mir-195 | 0.564628001 | 0.392046 |
| hsa-mir-027a | 0.622821419 | 0.251240619 | hsa-mir-425-5p | 0.554428361 | 0.275865 |
| hsa-mir-106a | 0.542577626 | 0.312616405 | hsa-let-7g | 0.515997707 | 0.337364 |
| hsa-let-7b | 0.534079686 | 0.25068168 | hsa-mir-021 | 0.51383279 | 0.491008 |
| hsa-mir-020b | 0.410435233 | 0.262371622 | hsa-mir-199a* | 0.503454664 | 0.327551 |
| hsa-mir-320 | 0.344918355 | 0.140441973 | hsa-mir-142-5p | 0.485752905 | 0.504504 |
| hsa-mir-425-5p | 0.334114444 | 0.131686276 | hsa-mir-103 | 0.469571039 | 0.215895 |
| hsa-mir-628 | 0.323074686 | 0.328272174 | hsa-mir-106b | 0.455236625 | 0.295268 |
| hsa-mir-302b | 0.31107497 | 0.233922375 | hsa-mir-182* | 0.450866408 | 0.779637 |
| hsa-mir-532 | 0.30283697 | 0.175299492 | hsa-mir-196b | 0.424682779 | 0.283318 |
| hsa-mir-196b | 0.291839926 | 0.203868959 | hsa-mir-643 | 0.410079866 | 0.934729 |
| hsa-mir-015a | 0.263528933 | 0.156658681 | hsa-mir-030d | 0.360317322 | 0.195419 |
| hsa-mir-183 | 0.223615225 | 0.225419033 | hsa-mir-423 | 0.355300524 | 0.267033 |
| hsa-mir-345 | 0.222589939 | 0.14617654 | hsa-let-7a | 0.316043353 | 0.197157 |
| hsa-mir-423 | 0.213547231 | 0.136842846 | hsa-mir-027b | 0.252490316 | 0.182518 |
| hsa-mir-103 | 0.205412359 | 0.093491856 | hsa-mir-374 | 0.251770179 | 0.197212 |
| hsa-let-7a | 0.198065472 | 0.082808812 | hsa-mir-020b | 0.227198431 | 0.167979 |
| hsa-mir-181d | 0.170055022 | 0.109234879 | hsa-mir-133b | 0.201227753 | 0.178372 |
| hsa-mir-182* | 0.151155794 | 0.079789533 | hsa-mir-425-3p | 0.183808363 | 0.094868 |
| hsa-mir-340 | 0.128492001 | 0.08303611 | hsa-mir-376a | 0.166829158 | 0.161986 |
| hsa-mir-425-3p | 0.127886265 | 0.097067479 | hsa-mir-340 | 0.113550436 | 0.088995 |
| hsa-mir-199a* | 0.127527328 | 0.079775882 | hsa-mir-015a | 0.110336695 | 0.095621 |
| hsa-mir-376a | 0.124903907 | 0.160137603 | hsa-mir-181d | 0.093074354 | 0.212993 |
| hsa-mir-643 | 0.116164417 | 0.195641411 | hsa-mir-532 | 0.086633253 | 0.064244 |
| hsa-mir-025 | 0.11319355 | 0.079644761 | hsa-mir-025 | 0.072911126 | 0.043857 |
| hsa-mir-133b | 0.100108157 | 0.121551814 | hsa-mir-345 | 0.071420142 | 0.054899 |
| hsa-mir-027b | 0.07101679 | 0.067406886 | hsa-mir-029a | 0.058322216 | 0.093625 |

FIG. 11 – Table VI (cont)

MICRORNA EXPRESSION IN HUMAN PERIPHERAL BLOOD MICROVESICLES AND USES THEREOF

This application is a continuation of U.S. application Ser. No. 13/873,371 filed Apr. 30, 2013, which application is a continuation of U.S. application Ser. No. 12/677,931 filed Apr. 12, 2010, now U.S. Pat. No. 8,455,199 issued Jun. 4, 2013, which claims the benefit of PCT application No. PCT/US08/076109 filed Sep. 12, 2008 which claims priority to U.S. Provisional Patent Application 60/993,809 filed Sep. 14, 2007, and 61/055,178 filed May 22, 2008, all of which applications are fully incorporated herein by reference. This invention was not made with any government support and the government has no rights in this invention.

SEQUENCE LISTING

The Instant application contains a Sequence Listing which has been submitted in ASCII format via EFS-Web and is hereby incorporated by reference in its entirety. Said ASCII copy, created Sep. 23, 2016, is named "37901792302.txt" and is 43,469 bytes in size.

BACKGROUND OF THE INVENTION

MicroRNAs (miRNAs or miRs) are small non-coding RNAs expressed in animals and plants. They regulate cellular function, cell survival, cell activation and cell differentiation during development.[7;8]

MicroRNAs are a small non-coding family of 19-25 nucleotide RNAs that regulate gene expression by targeting messenger RNAs (mRNA) in a sequence specific manner, inducing translational repression or mRNA degradation depending on the degree of complementarity between miRNAs and their targets (Bartel, D. P. (2004) *Cell* 116, 281-297; Ambros, V. (2004) *Nature* 431, 350-355). Many miRs are conserved in sequence between distantly related organisms, suggesting that these molecules participate in essential processes. Indeed, miRs are involved in the regulation of gene expression during development (Xu, P., et al. (2003) *Curr. Biol.* 13, 790-795), cell proliferation (Xu, P., et al. (2003) *Curr. Biol.* 13, 790-795), apoptosis (Cheng, A. M., et al. (2005) *Nucl. Acids Res.* 33, 1290-1297), glucose metabolism (Poy, M. N., et al. (2004) *Nature* 432, 226-230), stress resistance (Dresios, J., et al. (2005) *Proc. Natl. Acad. Sci. USA* 102, 1865-1870) and cancer (Calin, G. A, et al. (2002) *Proc. Natl. Acad. Sci. USA* 99, 1554-15529; Calin, G. A., et al. (2004) *Proc. Natl. Acad. Sci. USA* 101, 11755-11760; He, L., et al. (2005) *Nature* 435, 828-833; and Lu, J., et al. (2005) *Nature* 435:834-838).

There is also strong evidence that miRs play a role in mammalian hematopoiesis. In mice, miR-181, miR-223 and miR-142 are differentially expressed in hematopoietic tissues, and their expression is regulated during hematopoiesis and lineage commitment (Chen, C. Z., et al. (2004) *Science* 303, 83-86). The ectopic expression of miR-181 in murine hematopoietic progenitor cells led to proliferation in the B-cell compartment (Chen, C. Z., et al. (2004) *Science* 303, 83-86). Systematic miR gene profiling in cells of the murine hematopoietic system revealed different miR expression patterns in the hematopoietic system compared with neuronal tissues, and identified individual miR expression changes that occur during cell differentiation (Monticelli, S., et al. (2005) *Genome Biology* 6, R71). A recent study has identified down-modulation of miR-221 and miR-222 in human erythropoietic cultures of CD34+ cord blood progenitor cells (Felli, N., et al. (2005) *Proc. Natl. Acad. Sci. USA*. 102, 18081-18086). These miRs were found to target the oncogene c-Kit. Further functional studies indicated that the decline of these two miRs in erythropoietic cultures unblocks Kit protein production at the translational level leading to expansion of early erythroid cells (Felli, N., et al. (2005) *Proc. Natl. Acad. Sci. USA*. 102, 18081-18086). In line with the hypothesis of miRs regulating cell differentiation, miR-223 was found to be a key member of a regulatory circuit involving C/EBPa and NFI-A, which controls granulocytic differentiation in all-trans retinoic acid-treated acute promyelocytic leukemia cell lines (Fazi, F., et al. (2005) *Cell* 123, 819-831).

A frequent deletion and reduced expression of two miRs in B-cell chronic lymphocytic leukemia has been identified[9]. This discovery stimulated numerous articles documenting aberrant expression of miRs in head and neck carcinomas, small cell lung cancers, glioblastomas, breast cancers, chronic lymphocytic leukemia, and Burkitt lymphoma.[9-12] More recently, a relationship between inflammation and miRs has been reported in macrophages.[13]

In order to test for such disorders, tissue samples have been obtained in order to confirm the presence of such macrophages. In addition, until now, there has been no report demonstrating that microvesicles that circulate in the blood contain miRs.

Additional advantages, objects, and features of the invention will be set forth in part in the description which follows and in part will become apparent to those having ordinary skill in the art upon examination of the following or may be learned from practice of the invention. The objects and advantages of the invention may be realized and attained as particularly pointed out in the appended claims.

SUMMARY OF THE INVENTION

In one aspect, there is provided a method for identifying specific miRs that are present in microvesicles and/or have altered expression levels of specific miRs in tissue, fluids and/or cells.

Microvesicles facilitate communication between cells. Many cells including macrophages, platelets, T-cells, and tumors release small microvesicles containing nucleic acids and/or proteins[1-5]. Factors contained within the microvesicles regulate angiogenesis, cell growth, and cell differentiation[1;3].

In another aspect, the presence of miRs in such fluids as peripheral blood of patients suffering from particular disorders is determined.

In another aspect, the presence of miRs in lung tissue of patients suffering from pulmonary fibrosis is determined In yet another aspect, there is provided herein a method of diagnosing or prognosticating a particular disorder in a subject (e.g., a human) According to one particular method, the level of at least one miR gene product in a test sample from the subject is compared to the level of a corresponding miR gene product in a control sample. An alteration (e.g., an increase, a decrease) in the level of the miR gene product in the test sample, relative to the level of a corresponding miR gene product in the control sample, is indicative of the subject either having, or being at risk for developing, an acute inflammatory disorder.

In one embodiment, the level of the miR gene product in the test sample from the subject is greater than that of the control. In another embodiment, the at least one miR gene product is selected from the group consisting of the miRNAs as shown herein.

In particular embodiments, the disorder that is diagnosed or prognosticated is one that causes mononuclear phagocytes and/or THP-1 cells to release microvesicles.

In particular embodiments, the disorder that is diagnosed or prognosticated is one that causes an inflammatory response.

In another embodiment, the invention is a method of treating a cancer and/or an inflammatory disorder in a subject (e.g., a human).

In one particular method, an effective amount of a compound for inhibiting expression of at least one miR gene product selected from the one or more of the groups found in Table I-VI is administered to the subject.

In one embodiment, the compound for inhibiting expression of at least one miR gene product inhibits expression of a miR gene product selected from one or more of the groups found in Tables I-VI.

The invention further provides pharmaceutical compositions for treating cancer and/or an inflammatory disorder. In one embodiment, the pharmaceutical compositions of the invention comprise at least one miR expression-inhibition compound and a pharmaceutically-acceptable carrier. In a particular embodiment, the at least one miR expression-inhibition compound is specific for a miR gene product whose expression is greater in blood from diseased patients compared to normals.

In yet another embodiment, the pharmaceutical composition further comprises at least one anti-inflammatory agent.

In one embodiment, the invention is a pharmaceutical composition for treating a cancer associated with overexpression of a miR gene product and/or a lung disorder associated with overexpression of a miR gene product. Such pharmaceutical compositions comprise an effective amount of at least one miR gene product and a pharmaceutically-acceptable carrier, wherein the at least one miR gene product binds to, and decreases expression of, the miR gene product. In another embodiment, the at least one miR gene product comprises a nucleotide sequence that is complementary to a nucleotide sequence in the miR- gene product. In still another embodiment, the at least one miR gene product is miR- or a variant or biologically-active fragment thereof. In yet another embodiment, the pharmaceutical composition further comprises at least one anti-cancer agent.

Various objects and advantages of this invention will become apparent to those skilled in the art from the following detailed description of the preferred embodiment, when read in light of the accompanying drawings.

BRIEF DESCRIPTION OF THE DRAWINGS

(FIG. 5A) Hierarchal cluster analysis for microvesicles and PBMC is shown based on filtering criteria. Heat-maps demonstrating the expression profile for microvesicles (FIG. 5B) and PBMC (FIG. 5C) were generated. (FIG. 5D). The number of shared and specific for each sample group is shown.

FIG. 6: Table I showing various diseases and up- and down-regulated miRs associated therewith. microRNAs that are important in tissue of human diseases, including cancer and non-cancer applications are listed. Comparing miRNAs that are undetectable in the plasma from our data set (FIG. 7, Table II) with miRNAs known to increase in the tissue of specific diseases , the inventors now believe that we predict that several miRNAs may serve as biomarkers in the plasma (see miRs in bold in FIG. 6, Table I Increase Expression Column).

FIG. 7: Table II showing miRs that are expressed in the plasma and those that are undetectable.

FIG. 8: Table III lists miRs and show the top ten expressed miRNAs in the plasma microvesicles and the PBMC from all individuals.

FIG. 9: Table IV showing canonical pathways involved in metabolism and regulation of the acquired immune system were highly regulated by the expression of these miRNAs using Sanger miRBase alone (top) or common targets from Sanger miRBase and TargetScan (bottom).

FIG. 10: Table V showing that 20 miRNAs had more than a three-fold increase in expression in the PBMC fraction compared to the microvesicles plasma samples as well as the fold change in plasma microvesicles compared to PMBC (last Column)

FIG. 11: Table VI showing, the normalized expression data for all detected miRs: detector name, ave-MNC, std-MNC, detector name, ave-serum, std-serum.

DETAILED DESCRIPTION OF THE PREFERRED EMBODIMENT

Figure 1:
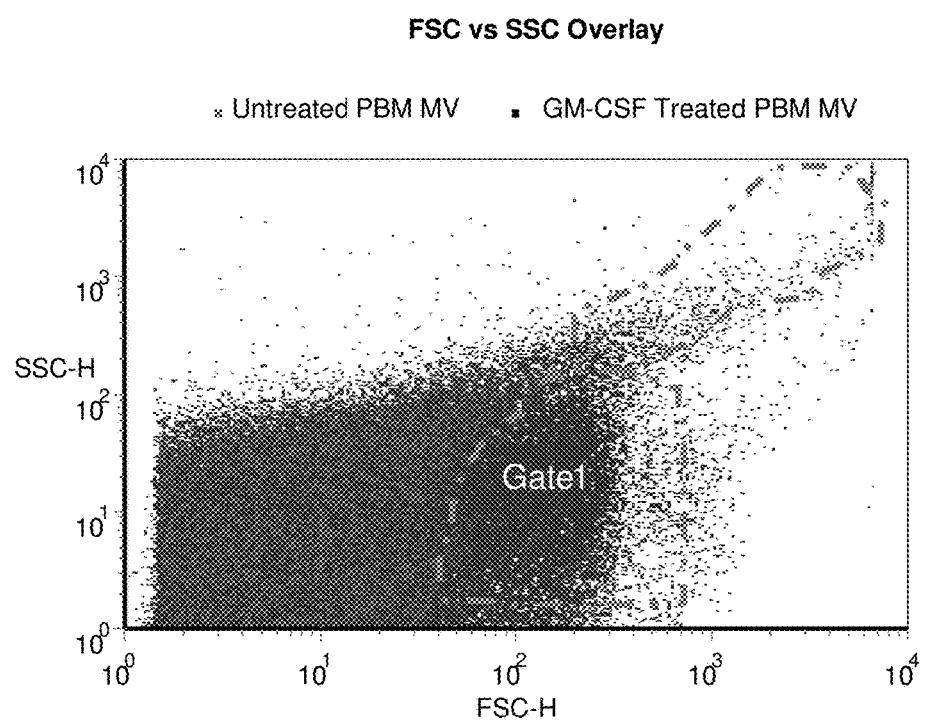
FIG. 1 shows the differentiation induced release of microvesicles from macrophages. Peripheral blood monocytes (PBM) were untreated (light) or treated with GM-CSF (dark) for 24 h. Cell-free supernatant was collected and ultracentrifuged. The vesicles were resuspended in PBS and analyzed for size on a flow cytometry. Prior to analysis, FSS and SSC parameters were adjusted using 2 µm standard beads (not shown). Shown is representative data from three different donors.

The present invention is based, in part, on the identification of specific microRNAs (miRNAs) that are involved in an inflammatory response and/or have altered expression levels in blood. The invention is further based, in part, on association of these miRNAs with particular diagnostic, prognostic and therapeutic features.

As described and exemplified herein particular miRNA are up- or down-regulated during tissue injury and/or inflammation.

As used herein interchangeably, a "miR gene product," "microRNA," "miR," "miR" or "miRNA" refers to the unprocessed or processed RNA transcript from a miR gene. As the miR gene products are not translated into protein, the term "miR gene products" does not include proteins. The unprocessed miR gene transcript is also called a "miR precursor," and typically comprises an RNA transcript of about 70-100 nucleotides in length. The miR precursor can be processed by digestion with an RNAse (for example, Dicer, Argonaut, RNAse III (e.g., E. coli RNAse III)) into an active 19-25 nucleotide RNA molecule. This active 19-25 nucleotide RNA molecule is also called the "processed" miR gene transcript or "mature" miRNA.

The active 19-25 nucleotide RNA molecule can be obtained from the miR precursor through natural processing routes (e.g., using intact cells or cell lysates) or by synthetic processing routes (e.g., using isolated processing enzymes, such as isolated Dicer, Argonaut, or RNAse III). It is understood that the active 19-25 nucleotide RNA molecule can also be produced directly by biological or chemical synthesis, without having to be processed from the miR precursor. When a microRNA is referred to herein by name, the name corresponds to both the precursor and mature forms, unless otherwise indicated.

The present invention encompasses methods of diagnosing or prognosticating whether a subject has, or is at risk for developing, a disorder where microvesicles are released.

The methods comprise determining the level of at least one miR gene product in a sample from the subject and comparing the level of the miR gene product in the sample to a control. As used herein, a "subject" can be any mammal that has, or is suspected of having, such disorder. In a preferred embodiment, the subject is a human who has, or is suspected of having, such disorder.

The level of at least one miR gene product can be measured in cells of a biological sample obtained from the subject.

In another embodiment, a sample can be removed from the subject, and DNA can be extracted and isolated by standard techniques. For example, in certain embodiments, the sample can be obtained from the subject prior to initiation of radiotherapy, chemotherapy or other therapeutic treatment. A corresponding control sample, or a control reference sample (e.g., obtained from a population of control samples), can be obtained from unaffected samples of the subject, from a normal human individual or population of normal individuals, or from cultured cells corresponding to the majority of cells in the subject's sample. The control sample can then be processed along with the sample from the subject, so that the levels of miR gene product produced from a given miR gene in cells from the subject's sample can be compared to the corresponding miR gene product levels from cells of the control sample. Alternatively, a reference sample can be obtained and processed separately (e.g., at a different time) from the test sample and the level of a miR gene product produced from a given miR gene in cells from the test sample can be compared to the corresponding miR gene product level from the reference sample.

In one embodiment, the level of the at least one miR gene product in the test sample is greater than the level of the corresponding miR gene product in the control sample (i.e., expression of the miR gene product is "upregulated"). As used herein, expression of a miR gene product is "upregulated" when the amount of miR gene product in a sample from a subject is greater than the amount of the same gene product in a control (for example, a reference standard, a control cell sample, a control tissue sample).

In another embodiment, the level of the at least one miR gene product in the test sample is less than the level of the corresponding miR gene product in the control sample (i.e., expression of the miR gene product is "downregulated"). As used herein, expression of a miR gene is "downregulated" when the amount of miR gene product produced from that gene in a sample from a subject is less than the amount produced from the same gene in a control sample. The relative miR gene expression in the control and normal samples can be determined with respect to one or more RNA expression standards. The standards can comprise, for example, a zero miR gene expression level, the miR gene expression level in a standard cell line, the miR gene expression level in unaffected samples of the subject, or the average level of miR gene expression previously obtained for a population of normal human controls (e.g., a control reference standard).

The level of the at least one miR gene product can be measured using a variety of techniques that are well known to those of skill in the art (e.g., quantitative or semi-quantitative RT-PCR, Northern blot analysis, solution hybridization detection). In a particular embodiment, the level of at least one miR gene product is measured by reverse transcribing RNA from a test sample obtained from the subject to provide a set of target oligodeoxynucleotides, hybridizing the target oligodeoxynucleotides to one or more miRNA-specific probe oligonucleotides (e.g., a microarray that comprises miRNA-specific probe oligonucleotides) to provide a hybridization profile for the test sample, and comparing the test sample hybridization profile to a hybridization profile generated from a control sample. An alteration in the signal of at least one miRNA in the test sample relative to the control sample is indicative of the subject either having, or being at risk for a particular disorder.

Also, a microarray can be prepared from gene-specific oligonucleotide probes generated from known miRNA sequences. The array may contain two different oligonucleotide probes for each miRNA, one containing the active, mature sequence and the other being specific for the precursor of the miRNA. The array may also contain controls, such as one or more mouse sequences differing from human orthologs by only a few bases, which can serve as controls for hybridization stringency conditions. tRNAs and other RNAs (e.g., rRNAs, mRNAs) from both species may also be printed on the microchip, providing an internal, relatively stable, positive control for specific hybridization. One or more appropriate controls for non-specific hybridization may also be included on the microchip. For this purpose, sequences are selected based upon the absence of any homology with any known miRNAs.

The microarray may be fabricated using techniques known in the art. For example, probe oligonucleotides of an appropriate length, e.g., 40 nucleotides, are 5'-amine modified at position C6 and printed using commercially available microarray systems, e.g., the GeneMachine OmniGrid™ 100 Microarrayer and Amersham CodeLink™ activated slides. Labeled cDNA oligomer corresponding to the target RNAs is prepared by reverse transcribing the target RNA with labeled primer. Following first strand synthesis, the RNA/DNA hybrids are denatured to degrade the RNA templates. The labeled target cDNAs thus prepared are then hybridized to the microarray chip under hybridizing conditions, e.g., 6× SSPE/30% formamide at 25° C. for 18 hours, followed by washing in 0.75×TNT at 37° C. for 40 minutes.

At positions on the array where the immobilized probe DNA recognizes a complementary target cDNA in the sample, hybridization occurs. The labeled target cDNA marks the exact position on the array where binding occurs, allowing automatic detection and quantification. The output consists of a list of hybridization events, indicating the relative abundance of specific cDNA sequences, and therefore the relative abundance of the corresponding complementary miRs, in the patient sample. According to one embodiment, the labeled cDNA oligomer is a biotin-labeled cDNA, prepared from a biotin-labeled primer. The microarray is then processed by direct detection of the biotin-containing transcripts using, e.g., Streptavidin-Alexa647 conjugate, and scanned utilizing conventional scanning methods. Image intensities of each spot on the array are proportional to the abundance of the corresponding miR in the patient sample.

The use of the array has several advantages for miRNA expression detection. First, the global expression of several hundred genes can be identified in the same sample at one time point. Second, through careful design of the oligonucleotide probes, expression of both mature and precursor molecules can be identified. Third, in comparison with Northern blot analysis, the chip requires a small amount of RNA, and provides reproducible results using 2.5 µg of total RNA. The relatively limited number of miRNAs (a few hundred per species) allows the construction of a common microarray for several species, with distinct oligonucleotide probes for each. Such a tool allows for analysis of trans-species expression for each known miR under various conditions.

In addition to use for quantitative expression level assays of specific miRs, a microchip containing miRNA-specific probe oligonucleotides corresponding to a substantial portion of the miRNome, preferably the entire miRNome, may be employed to carry out miR gene expression profiling, for analysis of miR expression patterns. Distinct miR signatures can be associated with established disease markers, or directly with a disease state.

According to the expression profiling methods described herein, total RNA from a sample from a subject suspected of having a particular disorder is quantitatively reverse transcribed to provide a set of labeled target oligodeoxynucleotides complementary to the RNA in the sample. The target oligodeoxynucleotides are then hybridized to a microarray comprising miRNA-specific probe oligonucleotides to provide a hybridization profile for the sample. The result is a hybridization profile for the sample representing the expression pattern of miRNA in the sample. The hybridization profile comprises the signal from the binding of the target oligodeoxynucleotides from the sample to the miRNA-specific probe oligonucleotides in the microarray. The profile may be recorded as the presence or absence of binding (signal vs. zero signal). More preferably, the profile recorded includes the intensity of the signal from each hybridization. The profile is compared to the hybridization profile generated from a normal control sample or reference sample. An alteration in the signal is indicative of the presence of, or propensity to develop, the particular disorder in the subject.

Other techniques for measuring miR gene expression are also within the skill in the art, and include various techniques for measuring rates of RNA transcription and degradation.

The invention also provides methods of diagnosing whether a subject has, or is at risk for developing, a particular disorder with an adverse prognosis. In this method, the level of at least one miR gene product, which is associated with an adverse prognosis in a particular disorder, is measured by reverse transcribing RNA from a test sample obtained from the subject to provide a set of target oligodeoxynucleotides. The target oligodeoxynucleotides are then hybridized to one or more miRNA-specific probe oligonucleotides (e.g., a microarray that comprises miRNA-specific probe oligonucleotides) to provide a hybridization profile for the test sample, and the test sample hybridization profile is compared to a hybridization profile generated from a control sample. An alteration in the signal of at least one miRNA in the test sample relative to the control sample is indicative of the subject either having, or being at risk for developing, a particular disorder with an adverse prognosis.

In some instances, it may be desirable to simultaneously determine the expression level of a plurality of different miR gene products in a sample. In other instances, it may be desirable to determine the expression level of the transcripts of all known miR genes correlated with a particular disorder. Assessing specific expression levels for hundreds of miR genes or gene products is time consuming and requires a large amount of total RNA (e.g., at least 20 µg for each Northern blot) and autoradiographic techniques that require radioactive isotopes.

To overcome these limitations, an oligolibrary, in microchip format (i.e., a microarray), may be constructed containing a set of oligonucleotide (e.g., oligodeoxynucleotide) probes that are specific for a set of miR genes. Using such a microarray, the expression level of multiple microRNAs in a biological sample can be determined by reverse transcribing the RNAs to generate a set of target oligodeoxynucleotides, and hybridizing them to probe the oligonucleotides on the microarray to generate a hybridization, or expression, profile. The hybridization profile of the test sample can then be compared to that of a control sample to determine which microRNAs have an altered expression level. As used herein, "probe oligonucleotide" or "probe oligodeoxynucleotide" refers to an oligonucleotide that is capable of hybridizing to a target oligonucleotide. "Target oligonucleotide" or "target oligodeoxynucleotide" refers to a molecule to be detected (e.g., via hybridization). By "miR-specific probe oligonucleotide" or "probe oligonucleotide specific for a miR" is meant a probe oligonucleotide that has a sequence selected to hybridize to a specific miR gene product, or to a reverse transcript of the specific miR gene product.

An "expression profile" or "hybridization profile" of a particular sample is essentially a fingerprint of the state of the sample; while two states may have any particular gene similarly expressed, the evaluation of a number of genes simultaneously allows the generation of a gene expression profile that is unique to the state of the cell. That is, normal samples may be distinguished from corresponding disorder-exhibiting samples. Within such disorder-exhibiting samples, different prognosis states (for example, good or poor long term survival prospects) may be determined By comparing expression profiles of disorder-exhibiting samples in different states, information regarding which genes are important (including both upregulation and downregulation of genes) in each of these states is obtained.

The identification of sequences that are differentially expressed in disorder-exhibiting samples, as well as differential expression resulting in different prognostic outcomes, allows the use of this information in a number of ways. For example, a particular treatment regime may be evaluated (e.g., to determine whether a chemotherapeutic drug acts to improve the long-term prognosis in a particular subject). Similarly, diagnosis may be done or confirmed by comparing samples from a subject with known expression profiles. Furthermore, these gene expression profiles (or individual genes) allow screening of drug candidates that suppress the particular disorder expression profile or convert a poor prognosis profile to a better prognosis profile.

Alterations in the level of one or more miR gene products in cells can result in the deregulation of one or more intended targets for these miRs, which can lead to a particular disorder. Therefore, altering the level of the miR gene product (e.g., by decreasing the level of a miR that is upregulated in disorder-exhibiting cells, by increasing the level of a miR that is downregulated in disorder-exhibiting cells) may successfully treat the disorder.

Accordingly, the present invention encompasses methods of treating a disorder in a subject, wherein at least one miR gene product is deregulated (e.g., downregulated, upregulated) in the cells of the subject. In one embodiment, the level of at least one miR gene product in a test sample is greater than the level of the corresponding miR gene product in a control or reference sample. In another embodiment, the level of at least one miR gene product in a test sample is less than the level of the corresponding miR gene product in a control sample. When the at least one isolated miR gene product is downregulated in the test sample, the method comprises administering an effective amount of the at least one isolated miR gene product, or an isolated variant or biologically-active fragment thereof, such that proliferation of the disorder-exhibiting cells in the subject is inhibited.

For example, when a miR gene product is downregulated in a cancer cell in a subject, administering an effective amount of an isolated miR gene product to the subject can inhibit proliferation of the cancer cell. The isolated miR gene product that is administered to the subject can be identical to an endogenous wild-type miR gene product that is downregulated in the cancer cell or it can be a variant or biologically-active fragment thereof.

As defined herein, a "variant" of a miR gene product refers to a miRNA that has less than 100% identity to a corresponding wild-type miR gene product and possesses one or more biological activities of the corresponding wild-type miR gene product. Examples of such biological activities include, but are not limited to, inhibition of expression of a target RNA molecule (e g , inhibiting translation of a target RNA molecule, modulating the stability of a target RNA molecule, inhibiting processing of a target RNA molecule) and inhibition of a cellular process associated with cancer and/or a myeloproliferative disorder (e.g., cell differentiation, cell growth, cell death). These variants include species variants and variants that are the consequence of one or more mutations (e.g., a substitution, a deletion, an insertion) in a miR gene. In certain embodiments, the variant is at least about 70%, 75%, 80%, 85%, 90%, 95%, 98%, or 99% identical to a corresponding wild-type miR gene product.

As defined herein, a "biologically-active fragment" of a miR gene product refers to an RNA fragment of a miR gene product that possesses one or more biological activities of a corresponding wild-type miR gene product. As described above, examples of such biological activities include, but are not limited to, inhibition of expression of a target RNA molecule and inhibition of a cellular process associated with cancer and/or a myeloproliferative disorder. In certain embodiments, the biologically-active fragment is at least about 5, 7, 10, 12, 15, or 17 nucleotides in length. In a particular embodiment, an isolated miR gene product can be administered to a subject in combination with one or more additional anti-cancer treatments. Suitable anti-cancer treatments include, but are not limited to, chemotherapy, radiation therapy and combinations thereof (e.g., chemoradiation).

When the at least one isolated miR gene product is upregulated in the cancer cells, the method comprises administering to the subject an effective amount of a compound that inhibits expression of the at least one miR gene product, such that proliferation of the disorder-exhibiting cells is inhibited. Such compounds are referred to herein as miR gene expression-inhibition compounds. Examples of suitable miR gene expression-inhibition compounds include, but are not limited to, those described herein (e.g., double-stranded RNA, antisense nucleic acids and enzymatic RNA molecules).

In a particular embodiment, a miR gene expression-inhibiting compound can be administered to a subject in combination with one or more additional anti-cancer treatments. Suitable anti-cancer treatments include, but are not limited to, chemotherapy, radiation therapy and combinations thereof (e.g., chemoradiation).

As described herein, when the at least one isolated miR gene product is upregulated in cancer cells, the method comprises administering to the subject an effective amount of at least one compound for inhibiting expression of the at least one miR gene product, such that proliferation of cancer cells is inhibited.

The terms "treat", "treating" and "treatment", as used herein, refer to ameliorating symptoms associated with a disease or condition, for example, cancer and/or other condition or disorder, including preventing or delaying the onset of the disease symptoms, and/or lessening the severity or frequency of symptoms of the disease, disorder or condition. The terms "subject", "patient" and "individual" are defined herein to include animals, such as mammals, including, but not limited to, primates, cows, sheep, goats, horses, dogs, cats, rabbits, guinea pigs, rats, mice or other bovine, ovine, equine, canine, feline, rodent, or murine species. In a preferred embodiment, the animal is a human As used herein, an "isolated" miR gene product is one that is synthesized, or altered or removed from the natural state through human intervention. For example, a synthetic miR gene product, or a miR gene product partially or completely separated from the coexisting materials of its natural state, is considered to be "isolated." An isolated miR gene product can exist in a substantially-purified form, or can exist in a cell into which the miR gene product has been delivered. Thus, a miR gene product that is deliberately delivered to, or expressed in, a cell is considered an "isolated" miR gene product. A miR gene product produced inside a cell from a miR precursor molecule is also considered to be an "isolated" molecule. According to the invention, the isolated miR gene products described herein can be used for the manufacture of a medicament for treating a subject (e.g., a human)

Isolated miR gene products can be obtained using a number of standard techniques. For example, the miR gene products can be chemically synthesized or recombinantly produced using methods known in the art. In one embodiment, miR gene products are chemically synthesized using appropriately protected ribonucleoside phosphoramidites and a conventional DNA/RNA synthesizer. Commercial suppliers of synthetic RNA molecules or synthesis reagents include, e.g., Proligo (Hamburg, Germany), Dharmacon Research (Lafayette, Colo., U.S.A.), Pierce Chemical (part of Perbio Science, Rockford, Ill., U.S.A.), Glen Research (Sterling, Va., U.S.A.), ChemGenes (Ashland, Mass., U.S.A.) and Cruachem (Glasgow, UK).

Alternatively, the miR gene products can be expressed from recombinant circular or linear DNA plasmids using any suitable promoter. Suitable promoters for expressing RNA from a plasmid include, e.g., the U6 or H1 RNA pol III promoter sequences, or the cytomegalovirus promoters. Selection of other suitable promoters is within the skill in the art. The recombinant plasmids of the invention can also comprise inducible or regulatable promoters for expression of the miR gene products in cells (e.g., cancerous cells, cells exhibiting a myeloproliferative disorder).

The miR gene products that are expressed from recombinant plasmids can be isolated from cultured cell expression systems by standard techniques. The miR gene products that are expressed from recombinant plasmids can also be delivered to, and expressed directly in, cells.

The miR gene products can be expressed from a separate recombinant plasmid, or they can be expressed from the same recombinant plasmid. In one embodiment, the miR gene products are expressed as RNA precursor molecules from a single plasmid, and the precursor molecules are processed into the functional miR gene product by a suitable processing system, including, but not limited to, processing systems extant within a cancer cell.

Selection of plasmids suitable for expressing the miR gene products, methods for inserting nucleic acid sequences into the plasmid to express the gene products, and methods of delivering the recombinant plasmid to the cells of interest are within the skill in the art. See, for example, Zeng et al. (2002), *Molecular Cell* 9:1327-1333; Tuschl (2002), *Nat. Biotechnol,* 20:446-448; Brummelkamp et al. (2002), *Science* 296:550-553; Miyagishi et al. (2002), *Nat. Biotechnol.* 20:497-500; Paddison et al. (2002), *Genes Dev.* 16:948-958; Lee et al. (2002), *Nat. Biotechnol.* 20:500-505; and Paul et al. (2002), *Nat. Biotechnol.* 20:505-508, the entire disclosures of which are incorporated herein by reference. For example, in certain embodiments, a plasmid expressing the miR gene products can comprise a sequence encoding a miR precursor RNA under the control of the CMV intermediate-early promoter. As used herein, "under the control" of a promoter means that the nucleic acid sequences encoding the miR gene product are located 3' of the promoter, so that the promoter can initiate transcription of the miR gene product coding sequences.

The miR gene products can also be expressed from recombinant viral vectors. It is contemplated that the miR gene products can be expressed from two separate recombinant viral vectors, or from the same viral vector. The RNA expressed from the recombinant viral vectors can either be isolated from cultured cell expression systems by standard techniques, or can be expressed directly in cells (e.g., cancerous cells, cells exhibiting a myeloproliferative disorder).

In other embodiments of the treatment methods of the invention, an effective amount of at least one compound that inhibits miR expression can be administered to the subject. As used herein, "inhibiting miR expression" means that the production of the precursor and/or active, mature form of miR gene product after treatment is less than the amount produced prior to treatment. One skilled in the art can readily determine whether miR expression has been inhibited in cells using, for example, the techniques for determining miR transcript level discussed herein Inhibition can occur at the level of gene expression (i.e., by inhibiting transcription of a miR gene encoding the miR gene product) or at the level of processing (e.g., by inhibiting processing of a miR precursor into a mature, active miR).

As used herein, an "effective amount" of a compound that inhibits miR expression is an amount sufficient to inhibit proliferation of cells in a subject suffering from cancer and/or a myeloproliferative disorder. One skilled in the art can readily determine an effective amount of a miR expression-inhibiting compound to be administered to a given subject, by taking into account factors, such as the size and weight of the subject; the extent of disease penetration; the age, health and sex of the subject; the route of administration; and whether the administration is regional or systemic.

One skilled in the art can also readily determine an appropriate dosage regimen for administering a compound that inhibits miR expression to a given subject, as described herein. Suitable compounds for inhibiting miR gene expression include double-stranded RNA (such as short- or small-interfering RNA or "siRNA"), antisense nucleic acids, and enzymatic RNA molecules, such as ribozymes. Each of these compounds can be targeted to a given miR gene product and interfere with the expression (e.g., by inhibiting translation, by inducing cleavage and/or degradation) of the target miR gene product.

For example, expression of a given miR gene can be inhibited by inducing RNA interference of the miR gene with an isolated double-stranded RNA ("dsRNA") molecule which has at least 90%, for example, at least 95%, at least 98%, at least 99%, or 100%, sequence homology with at least a portion of the miR gene product. In a particular embodiment, the dsRNA molecule is a "short or small interfering RNA" or "siRNA."

Administration of at least one miR gene product, or at least one compound for inhibiting miR expression, will inhibit the proliferation of cells (e.g., cancerous cells, cells exhibiting a myeloproliferative disorder) in a subject who has a cancer and/or a myeloproliferative disorder. As used herein, to "inhibit the proliferation of cancerous cells or cells exhibiting a myeloproliferative disorder" means to kill the cells, or permanently or temporarily arrest or slow the growth of the cells Inhibition of cell proliferation can be inferred if the number of such cells in the subject remains constant or decreases after administration of the miR gene products or miR gene expression-inhibiting compounds. An inhibition of proliferation of cancerous cells or cells exhibiting a myeloproliferative disorder can also be inferred if the absolute number of such cells increases, but the rate of tumor growth decreases.

A miR gene product or miR gene expression-inhibiting compound can also be administered to a subject by any suitable enteral or parenteral administration route. Suitable enteral administration routes for the present methods include, e.g., oral, rectal, or intranasal delivery. Suitable parenteral administration routes include, e.g., intravascular administration (e.g., intravenous bolus injection, intravenous infusion, intra-arterial bolus injection, intra-arterial infusion and catheter instillation into the vasculature); peri- and intra-tissue injection (e.g., peri-tumoral and intra-tumoral injection, intra-retinal injection, or subretinal injection); subcutaneous injection or deposition, including subcutaneous infusion (such as by osmotic pumps); direct application to the tissue of interest, for example by a catheter or other placement device (e.g., a retinal pellet or a suppository or an implant comprising a porous, non-porous, or gelatinous material); and inhalation. Particularly suitable administration routes are injection, infusion and direct injection into the tumor.

The miR gene products or miR gene expression-inhibition compounds can be formulated as pharmaceutical compositions, sometimes called "medicaments," prior to administering them to a subject, according to techniques known in the art. Accordingly, the invention encompasses pharmaceutical compositions for treating cancer and/or a myeloproliferative disorder.

The present pharmaceutical compositions comprise at least one miR gene product or miR gene expression-inhibition compound (or at least one nucleic acid comprising a sequence encoding the miR gene product or miR gene expression-inhibition compound) (e.g., 0.1 to 90% by weight), or a physiologically-acceptable salt thereof, mixed with a pharmaceutically-acceptable carrier. In certain embodiments, the pharmaceutical composition of the invention additionally comprises one or more anti-cancer agents (e.g., chemotherapeutic agents). The pharmaceutical formulations of the invention can also comprise at least one miR gene product or miR gene expression-inhibition compound (or at least one nucleic acid comprising a sequence encoding the miR gene product or miR gene expression-inhibition compound), which are encapsulated by liposomes and a pharmaceutically-acceptable carrier.

Pharmaceutical compositions of the invention can also comprise conventional pharmaceutical excipients and/or additives. Suitable pharmaceutical excipients include stabilizers, antioxidants, osmolality adjusting agents, buffers, and pH adjusting agents. Suitable additives include, e.g., physiologically biocompatible buffers (e.g., tromethamine hydrochloride), additions of chelants (such as, for example, DTPA or DTPA-bisamide) or calcium chelate complexes (such as, for example, calcium DTPA, CaNaDTPA-bisamide), or, optionally, additions of calcium or sodium salts (for example, calcium chloride, calcium ascorbate, calcium gluconate or calcium lactate). Pharmaceutical compositions of the invention can be packaged for use in liquid form, or can be lyophilized.

For solid pharmaceutical compositions of the invention, conventional nontoxic solid pharmaceutically-acceptable carriers can be used; for example, pharmaceutical grades of mannitol, lactose, starch, magnesium stearate, sodium saccharin, talcum, cellulose, glucose, sucrose, magnesium carbonate, and the like.

For example, a solid pharmaceutical composition for oral administration can comprise any of the carriers and excipients listed above and 10-95%, preferably 25%-75%, of the at least one miR gene product or miR gene expression-inhibition compound (or at least one nucleic acid comprising sequences encoding them). A pharmaceutical composition for aerosol (inhalational) administration can comprise 0.01-20% by weight, preferably 1%-10% by weight, of the at least one miR gene product or miR gene expression-inhibition compound (or at least one nucleic acid comprising a sequence encoding the miR gene product or miR gene expression-inhibition compound) encapsulated in a liposome as described above, and a propellant. A carrier can also be included as desired; e.g., lecithin for intranasal delivery.

The pharmaceutical compositions of the invention can further comprise one or more anti-cancer agents. In a particular embodiment, the compositions comprise at least one miR gene product or miR gene expression-inhibition compound (or at least one nucleic acid comprising a sequence encoding the miR gene product or miR gene expression-inhibition compound) and at least one chemotherapeutic agent. Chemotherapeutic agents that are suitable for the methods of the invention include, but are not limited to, DNA-alkylating agents, anti-tumor antibiotic agents, anti-metabolic agents, tubulin stabilizing agents, tubulin destabilizing agents, hormone antagonist agents, topoisomerase inhibitors, protein kinase inhibitors, HMG-CoA inhibitors, CDK inhibitors, cyclin inhibitors, caspase inhibitors, metalloproteinase inhibitors, antisense nucleic acids, triple-helix DNAs, nucleic acids aptamers, and molecularly-modified viral, bacterial and exotoxic agents. Examples of suitable agents for the compositions of the present invention include, but are not limited to, cytidine arabinoside, methotrexate, vincristine, etoposide (VP-16), doxorubicin (adriamycin), cisplatin (CDDP), dexamethasone, arglabin, cyclophosphamide, sarcolysin, methylnitrosourea, fluorouracil, 5-fluorouracil (5FU), vinblastine, camptothecin, actinomycin-D, mitomycin C, hydrogen peroxide, oxaliplatin, irinotecan, topotecan, leucovorin, carmustine, streptozocin, CPT-11, taxol, tamoxifen, dacarbazine, rituximab, daunorubicin, 1-β-D-arabinofuranosylcytosine, imatinib, fludarabine, docetaxel and FOLFOX4.

In one embodiment, the method comprises providing a test agent to a cell and measuring the level of at least one miR gene product associated with decreased expression levels in cancerous cells. An increase in the level of the miR gene product in the cell, relative to a suitable control (e.g., the level of the miR gene product in a control cell), is indicative of the test agent being an anti-cancer agent.

Suitable agents include, but are not limited to drugs (e.g., small molecules, peptides), and biological macromolecules (e.g., proteins, nucleic acids). The agent can be produced recombinantly, synthetically, or it may be isolated (i.e., purified) from a natural source. Various methods for providing such agents to a cell (e.g., transfection) are well known in the art, and several of such methods are described hereinabove. Methods for detecting the expression of at least one miR gene product (e.g., Northern blotting, in situ hybridization, RT-PCR, expression profiling) are also well known in the art. Several of these methods are also described herein.

EXAMPLES

The invention may be better understood by reference to the following non-limiting examples, which serve to illustrate but not to limit the present invention.

The data herein show that activated human mononuclear phagocytes and THP-1 cells release microvesicles that induce the survival and differentiation of freshly isolate monocytes. While not wishing to be bound by theory, the inventors herein believe that under specific inflammatory diseases, the content of the microvesicles may be altered to rapidly induce a response. The data also show that microvesicles circulate in human peripheral blood. The circulating microvesicles regulate normal cellular homeostasis, and circulate instructions to distant cells during tissue injury and inflammation.

The microvesicles may serve as biomarkers for disease etiology and systemic mediators of the innate immune response. It is thus beneficial to be able to obtain similar information through the isolation of microvesicles in the peripheral blood instead of obtaining tissue through invasive procedures. Also, understanding the normal signature of microvesicles in the peripheral blood provides a basis for understanding events during acute inflammatory events.

As shown herein, aberrant macrophage differentiation contributes to disruption in immune homeostasis. Since monocyte maturation is induced by GM-CSF or M-CSF, the inventors initiated studies to understand the mechanisms and differences between GM-CSF- and M-CSF-mediated differentiation. The commitment to differentiate in response to GM-CSF but not M-CSF was rapid and irreversible (data not shown). Continuous GM-CSF stimulation was not required for this effect as only 4 hours of treatment induced macrophage differentiation. Similar observations were obtained in PMA-treated THP1 cells used as a model of macrophage differentiation.

Thus, the inventors determined that at least one factor was secreted upon inducing differentiation that either maintained signals or activated other cells to differentiate. Therefore, monocytes or THP1 cells were exposed to GM-CSF for 4 h or PMA for 1 h, respectively, after which cells were washed and placed in minimal media without stimulus. After 24 hours, the culture supernatants were collected and added to undifferentiated monocytes or THP1 cells. Notably, supernatants from PMA-treated THP1 cells or GM-CSF-treated monocytes differentiated monocytes and THP1 cells (data not shown).

Using the Bioplex suspension array system to detect up to 27 different cytokines in the culture supernatants, the inventors failed to detect a responsible cytokine. Since the inventors differentiated the growth factor-independent THP1 cell line with GM-CSF-stimulated monocyte supernatants, the inventors concluded that a cytokine/growth factor was not responsible for this effect. The inventors next investigated the possibility that microvesicles were secreted in the culture supernatant to mediate myeloid maturation.

As shown in FIG. 1, monocytes treated with GM-CSF for 24 hours released significant numbers of microvesicles (dark dots) in the culture supernatant compared to untreated monocytes (light dots).

Similarly, PMA-treated THP1 cells also secreted microvesicles during differentiation (data not shown). In particular, FIG. 1 shows the differentiation induced release of microvesicles from macrophages. Peripheral blood monocytes (PBM) were untreated (light) or treated with GM-CSF (dark) for 24 h. Cell-free supernatant was collected and ultracentrifuged. The vesicles were resuspended in PBS and analyzed for size on a flow cytometry. Prior to analysis, FSS and SSC parameters were adjusted using 2 μm standard beads (not shown). Shown is representative data from three different donors.

Figures 2A, 2B, 2C:
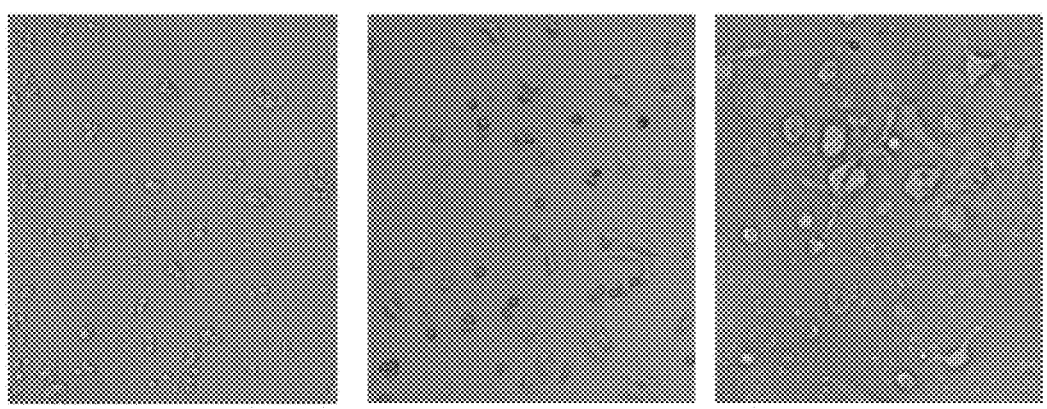
FIGS. 2A-2C show microvesicles mediate macrophage differentiation. Microvesicles were collected from PMA-treated THP1 cells then added to undifferentiated THP1 cells (FIG. 2B) or monocytes (FIG. 2C). As a control, THP1 cells were left untreated (FIG. 2A). The cells were photographed daily. Shown are the cells at day 3.

Microvesicles from PMA-treated THP1 cells were purified and added to either freshly isolated monocytes or undifferentiated THP1 cells. The microvesicles alone induced macrophage differentiation in both cell types as indicated by morphology (see FIGS. 2A-2C) and expression of surface antigens (data not shown).

The content of these microvesicles has been analyzed. The inventors detected the presence of miRNAs in the microvesicles from PMA-treated THP1 cells (data not shown).

Figure 3A:
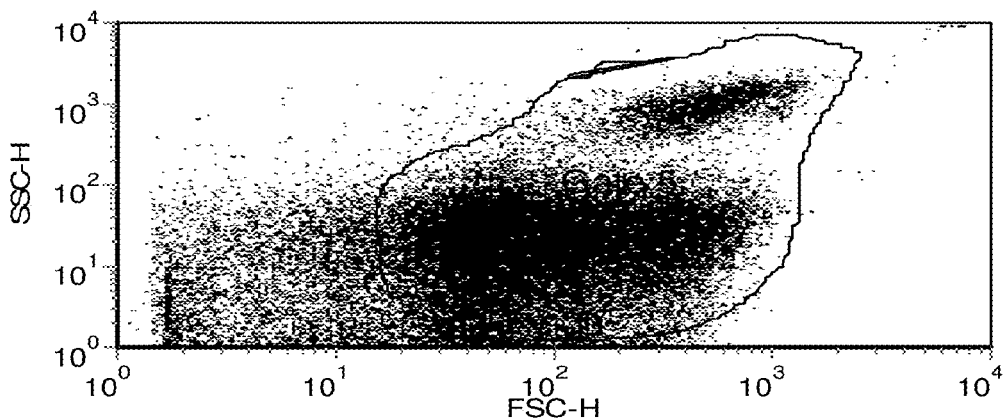
FIGS. 3A-3C show the isolation of peripheral blood microvesicles. Following informed consent, plasma was obtained from 20 cc of blood from normal volunteer donors. The microvesicles from 0.5 cc of plasma were incubated with CD206-FITC or MHCII-FITC antibodies and analyzed on BD FACS Calibur for size using forward vs. side scatter (FIG. 3A) and surface antigen expression (FIG. 3B). The percent expression of either CD206 or MHC II compared to isotype control was determined for the gated region shown in FIG. 3A (FIG. 3C). Shown is the average±SEM of two donors.
Figure 3B:
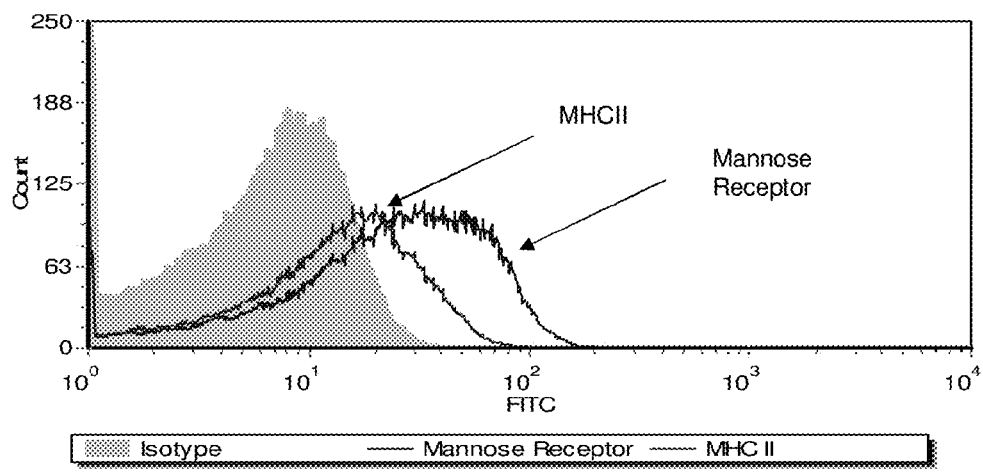
Figure 3C:
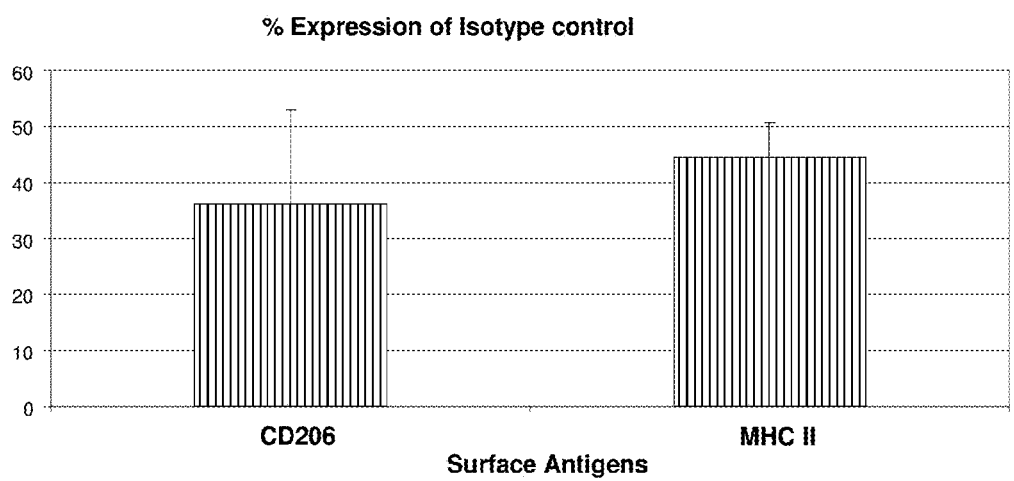

The inventors also evaluated circulating microvesicles and miRNA in the peripheral blood of normal volunteers. Based on size, the inventors found three subpopulations of microvesicles in the circulation (FIG. 3A). Macrophage-derived microvesicles were detected using antibodies that detect mannose receptor (CD206) and MHC II (FIG. 3B). Approximately 40% of the total microvesicles (gated region) in the plasma are derived from macrophages based on expression of either CD206 or MHCII (FIG. 3C).

The inventors further determined whether miRNA are contained in the peripheral blood microvesicles. We detected expression of numerous miRNAs. The highest detected miRNAs are shown in FIG. 8 showing Table III (n=51).

Notably, miR-146 is undetectable in the peripheral blood whereas miR-155 expression was 80-fold lower than the highest expressing miRNA. Since both miR-146 and miR-155 were elevated in our IPF patient samples, but were low to undetectable in peripheral blood from normal donors, examination of circulating miRNAs may serve as a bio-marker of disease.

It is now shown herein that circulating microvesicles contain miRNAs and that circulating microvesicles can provide an avenue for the miRNAs to elicit cell-to-cell communication. The microvesicles housing miRNA can also provide insight into the genetic basis of disease and can serve as predictive biomarkers.

Also, microvesicles released during macrophage differentiation can mediate maturation of immature cells. Microvesicles collected during macrophage maturation mediate the differentiation and survival of human monocytes and contain RNA. Both miRNA and processed mRNA are responsible for the maturation signals imparted on immature cells.

Example—Plasma

Microvesicles are isolated from the plasma of normal healthy individuals. RNA is isolated from both the microvesicles and matched mononuclear cells and profiled for 420 known mature miRNAs by real-time PCR. Hierarchal cluster analysis of the data sets indicated significant differences in miRNA expression between peripheral blood mononuclear cells (PBMC) and plasma microvesicles.

We observed 104 and 75 miRNAs significantly expressed in the microvesicles and PBMC, respectively. Notably, 33 miRNAs were specifically expressed microvesicles compared to the PBMC. The miRNA were subjected to computational modeling to determine the biological pathways regulated by the detected miRNAs. The majority of the microRNAs expressed in the microvesicles from the blood were predicted to regulate cellular differentiation of blood cells and metabolic pathways. Interestingly, a select few microRNAs are predicted to be important modulators of immune function.

This example is the first to identify and define miRNA expression in circulating plasma microvesicles of normal subjects.

Recent evidence reveals that genetic exchange of mRNA and miRNA between cells can be accomplished through exosome-mediated transfer (PMID: 17486113). Microvesicles are small exosomes/vesicles of endocytic origin released by normal healthy or damaged cell types (PMID: 17337785, PMID: 17409393, PMID: 16791265). Microvesicles are shed from the plasma membrane into the extracellular environment to facilitate communication between cells. Despite their small size (50nm to 1 μm) microvesicles are enriched in bioactive molecules and are suspected to contain nucleic acid and/or protein; these cell particles play a role in growth, differentiation and cancer progression (PMID: 16453000). In the peripheral blood, two-thirds of microvesicles are derived from platelets. Platelet-derived microvesicles play a role in angiogenesis and the metastatic spread of cancers such as lung cancer (PMID: 15499615). Platelet-derived microvesicles induce an immune response upon regulating gene expression in hematopoietic, endothelial, and monocytic cells (PMID: 17378242, PMID: 17127485).

Interestingly, a connection between microvesicles and miRNA has been recently made. Recently, Valadi and colleagues reported that vesicles released from human and murine mast cell lines contain over 1200 mRNA and approximately 121 miRNA molecules (PMID: 17486113) In contrast, the present invention relates to naturally occurring human plasma and blood microvesicles containing microRNA that leads to biological effects ex vivo.

FIG. 8—Table I shows that microRNAs that are important in human diseases, including cancer and non-cancer applications. The microRNA molecules associated with increase expression in disease tissue but normally with low native or undetectable expression in human plasma microvesicles (Table I, shown in FIG. 6) provides the opportunity to define changes in health and disease and may be effective biomarkers (Bold, Increase Expression Column). Similarly, normally abundant microRNAs may decrease in human plasma microvesicles to reflect the decrease observed in tissue (Bold, Decrease Expression Column).

Considerable evidence demonstrates the importance of miRNA as an inevitable cornerstone of the human genetic system. Employing the use of microvesicles to transfer genetic material would be an efficient transfer method within the human body. Microvesicular transport of miRNAs would enable communication at long distance.

Methods

Blood collection and microvesicle isolation. Peripheral blood (40 cc) was collected in EDTA tubes from 24 females and 27 males healthy non-smoking Caucasian donors following informed consent. Collection of the blood occurred either between morning and early afternoon. The median age for female donors was 29 as well as for male donors. The peripheral blood was diluted 1:1 with sterile low endotoxin PBS, layered over ficoll-hypaque (d=1.077), and centrifuged as previously described (PMID: 16931806). The mononuclear cell fraction was washed once in PBS. The microvesicles were purified from the plasma. Briefly, the vesicles were concentrated by centrifugation at 160,000×g for 1hr at 4° C. (PMID: 10648405).

RNA Extraction. Total RNA was isolated by Trizol (Invitrogen, Carlsbad, CA) extraction method. To increase the yield of small RNAs, the RNA was precipitated overnight. RNA concentration was determined and RNA integrity was a determined by capillary electrophoresis on an Agilent 2100 Bioanalyzer (Agilent Technologies, Inc, Santa Clara, Calif.). For RNA isolated from mononuclear cells, only a RNA integrity number (RIN) ≥9 was used. Since the intact 18s and 28s rRNA was variable in the microvesicles, the RIN was not a constraint for these samples.

miRNA profiling by quantitative PCR. The expression of 420 mature human miRNAs was profiled by real-time PCR. RNA (50 ng) was converted to cDNA by priming with a mixture of looped primers to 420 known human mature miRNAs (Mega Plex kit, Applied Biosystems, Foster City, Calif.) using previously published reverse transcription conditions (PMID: 18158130). As there is no known control miRNA in microvesicles, several internal controls were examined. Primers to the internal controls, small nucleolar (sno)RNA U38B, snoRNA U43, small nuclear (sn)RNA U6 as well as 18S and 5S rRNA were included in the mix of primers.

The expression was profiled using an Applied Biosystems 7900HT real-time PCR instrument equipped with a 384 well reaction plate. Liquid-handling robots and the Zymak Twister robot were used to increase throughput and reduce error. Real-time PCR was performed using standard conditions.

Flow Cytometry. Peripheral blood microvesicles were directly immunostained from plasma without concentration by centrifugation. To determine the cellular origin, 0.5 cc plasma was immunostained per panel of antibodies. Panel I contained antibodies recognizing CD66b-FITC (neutrophil), CD202b (Tie2)-PE (endothelial), CD206 PE-Cy5 (macrophage/dendritic), CD79a-APC (B-cell), and CD14 Pe-Cy7 (monocyte). Panel II contained antibodies to CD41a-PE-Cy5 (platelet), CCR2-APC (monocyte), CCR3-PE (dendritic cell), CCR5-PE-Cy7 (macrophage), and CD3-Alexa 610 (T-cell). Panel III contained isotype control antibodies. The samples were analyzed on BD Aria flow cytometer (BD Biosciences San Jose, Calif.). Data was expressed as percent of gated cells.

Statistical analysis. To reduce background noise, the miRNAs in which 80% of individual observations had a raw CT score greater than 35 were not considered during the data analysis. The internal controls (18S, 5S, snoRNA U38B, snoRNA U43, and snRNA U6) were highly variable in the plasma microvesicles as well as significantly different levels of expression in plasma microvesicles versus peripheral blood mononuclear cells (PBMC).

Thus, to reduce bias caused by using a certain miRNA as a normalization correction factor and to reduce the sample variations among RT-PCR arrays, the miRNAs were compared between plasma microvesicles and PBMC based on their relative expression to the overall miRNA expression on each array using median normalization analysis (PMID: 16854228). Controlling gender and age of the donors, linear mixed models were used to estimate the difference of specific miRNA between plasma microvesicles and PBMC. Fold-change was calculated based on the estimated mean difference.

Heat maps were generated using the miRNA that passed the filtering criteria for each tissue and miRNAs were subjected to hierarchical clustering based on their relative mean expression. miRNA expression was also ranked based on their raw CT score for plasma microvesicles and PBMC. Additional statistical analysis such as ANOVA was performed to determine miRNAs that are significant expressed between the two treatment groups Pathway analysis and prediction. Predicted miRNAs targets were determined using miRanda (microrna.sanger.ac.uk/targets/v5/). Based on the miRanda algorithm, a score is generated for each target, only scores greater than 17 were furthered analyzed using Ingenuity Pathway Analysis software (Ingenuity Systems, Redwood City, Calif.). Using this software, canonical pathways were determined based on targets of the miRNAs. The dataset was examined to determine associated pathways based on gene ontology of miRNA's targets.

Results

Peripheral Blood Microvesicle Subpopulations

Figure 4:
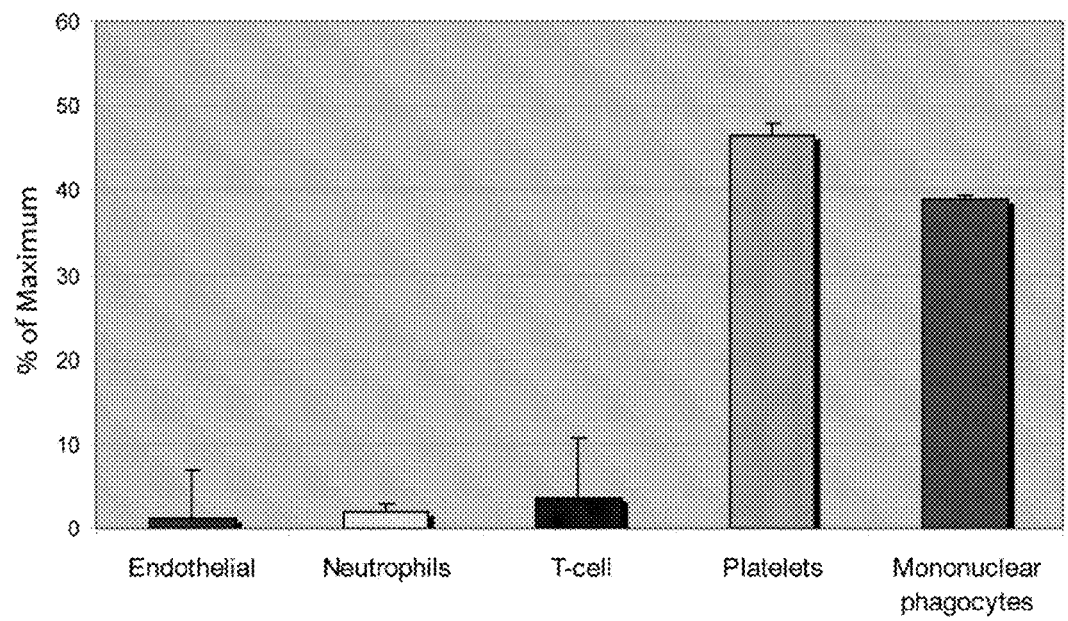
FIG. 4. Analysis of the origin of peripheral blood microvesicles. Peripheral blood microvesicles from healthy donors (n=10) were analyzed by flow cytometry. To determine cell origin, microvesicles were stained for CD3, CD202b (Tie-2), CD66b, CD79a, or CD41a to determine those that originated from T-cells, endothelial cells, neutrophils, B-cells, or platelets. Mononuclear phagocyte-derived microvesicles were positive for CD14, CD206, CCR3, CCR2, or CCR5. Shown is the average % maximum of total gated events ±S.E.M.

Initially, we examined the cellular origin of microvesicles within the peripheral blood of normal healthy individuals. Using flow cytometry, we found that the majority of the peripheral blood microvesicles are platelet-derived (FIG. 4), as previously reported (PMID: 10648405).

We also observed a second large population of microvesicles that were derived from mononuclear cell phagocyte lineage. This population was immunostained with antibodies that detected surface antigens on mononuclear phagocytes. Notably, only a small percentage of the peripheral blood microvesicles were derived from T-cells and neutrophils. We failed to detect vesicles that originated from B-cells (data not shown). Of interest, we detected a small subpopulation of microvesicles that expressed surface antigens from endothelial cells.

miRNA Expression in Plasma Microvesicles and PBMC

To test whether miRNAs are contained in the microvesicle compartment within the peripheral blood to enable communication and influence genetic changes between different tissues within the body, we performed miRNA profiling on the purified microvesicles from the plasma. We analyzed all subpopulations of microvesicles from 51 non-smoking healthy individuals comprising of 27 males and 24 females. In order to determine whether there would be differences in miRNA expression between microvesicles and PBMC, we also purified the PBMC from each donor. Real-time PCR analysis was performed to examine the expression of 420 miRNAs. The filtered data was subjected to hierarchal cluster analysis comparing the miRNA expression profile between the PBMC and plasma samples (FIG. 5A).

All but three PBMC samples clustered separately from the microvesicle samples, indicating that the miRNA expression profile between the two groups was significantly different. Based on filtering criteria to reduce background noise, we found 104 and 75 miRNAs expressed in the microvesicles and PBMC samples, respectively (FIGS. 5B and 5C).

Figure 5D:
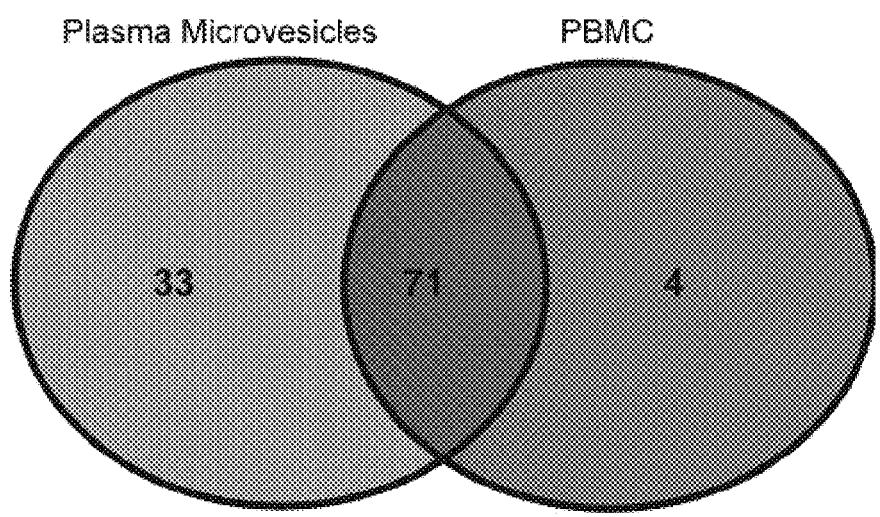
FIGS. 5A-5D. miRNA expression from peripheral blood microvesicles and PBMC.
Figure 5A:
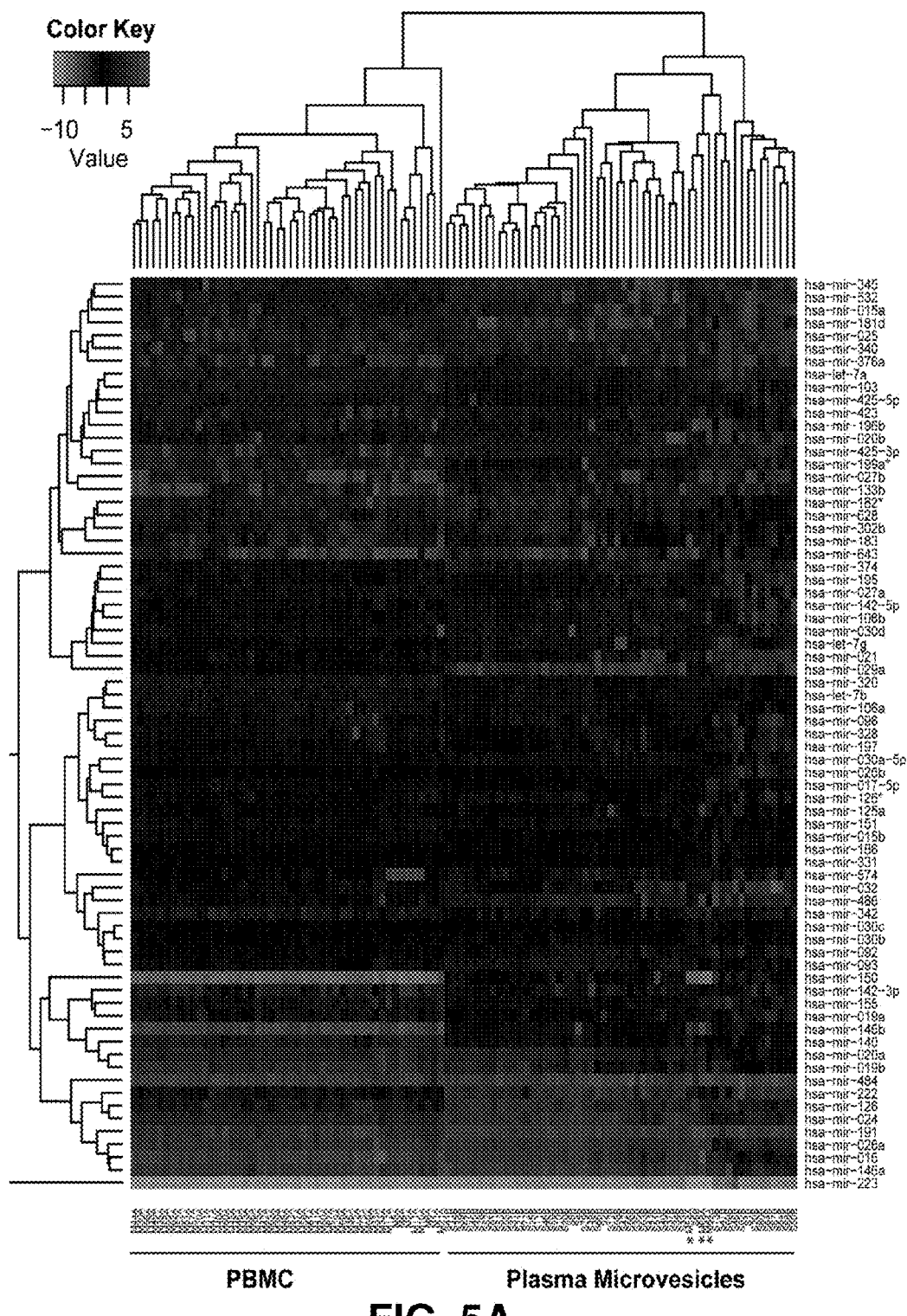
Figure 5B:
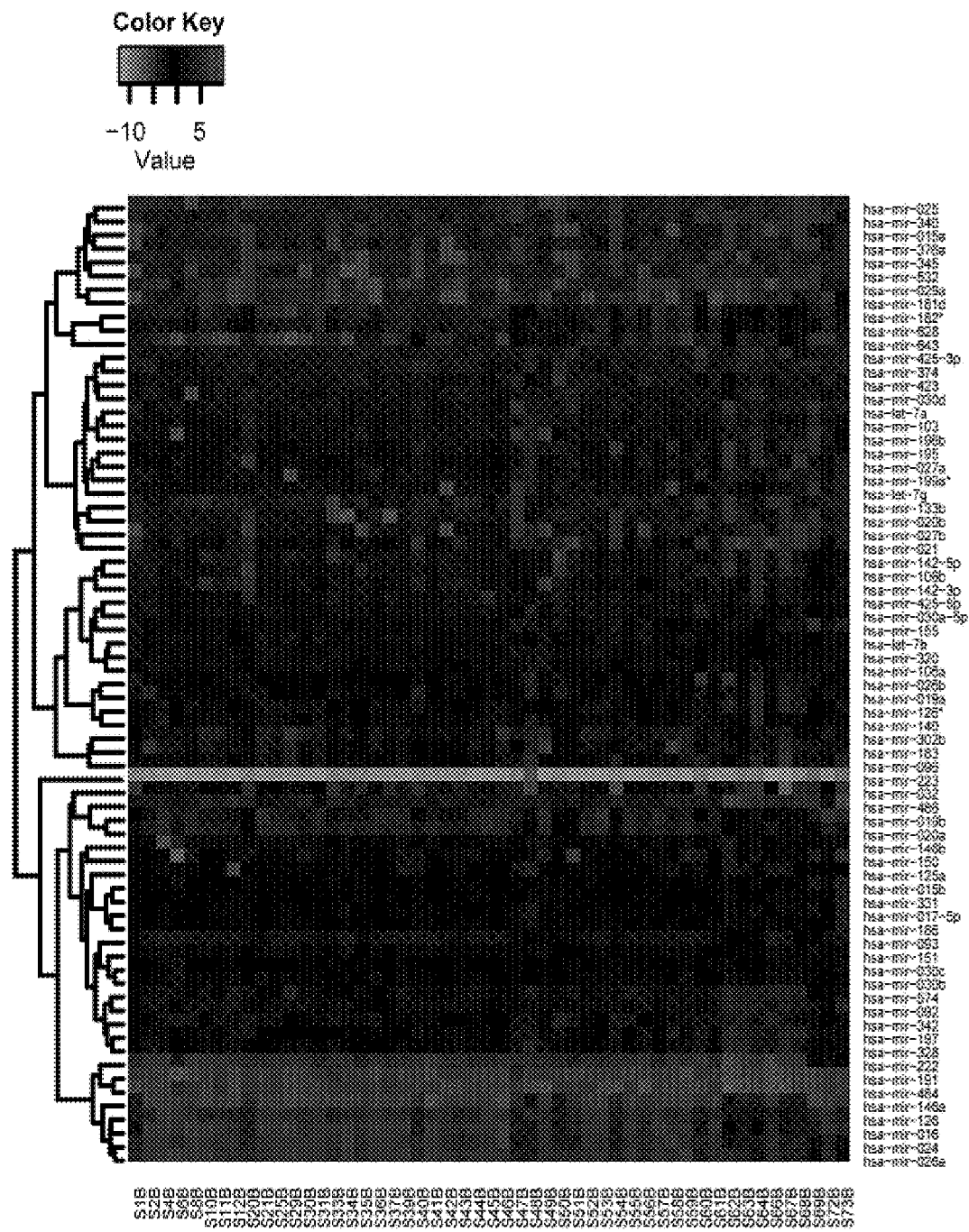
Figure 5C:
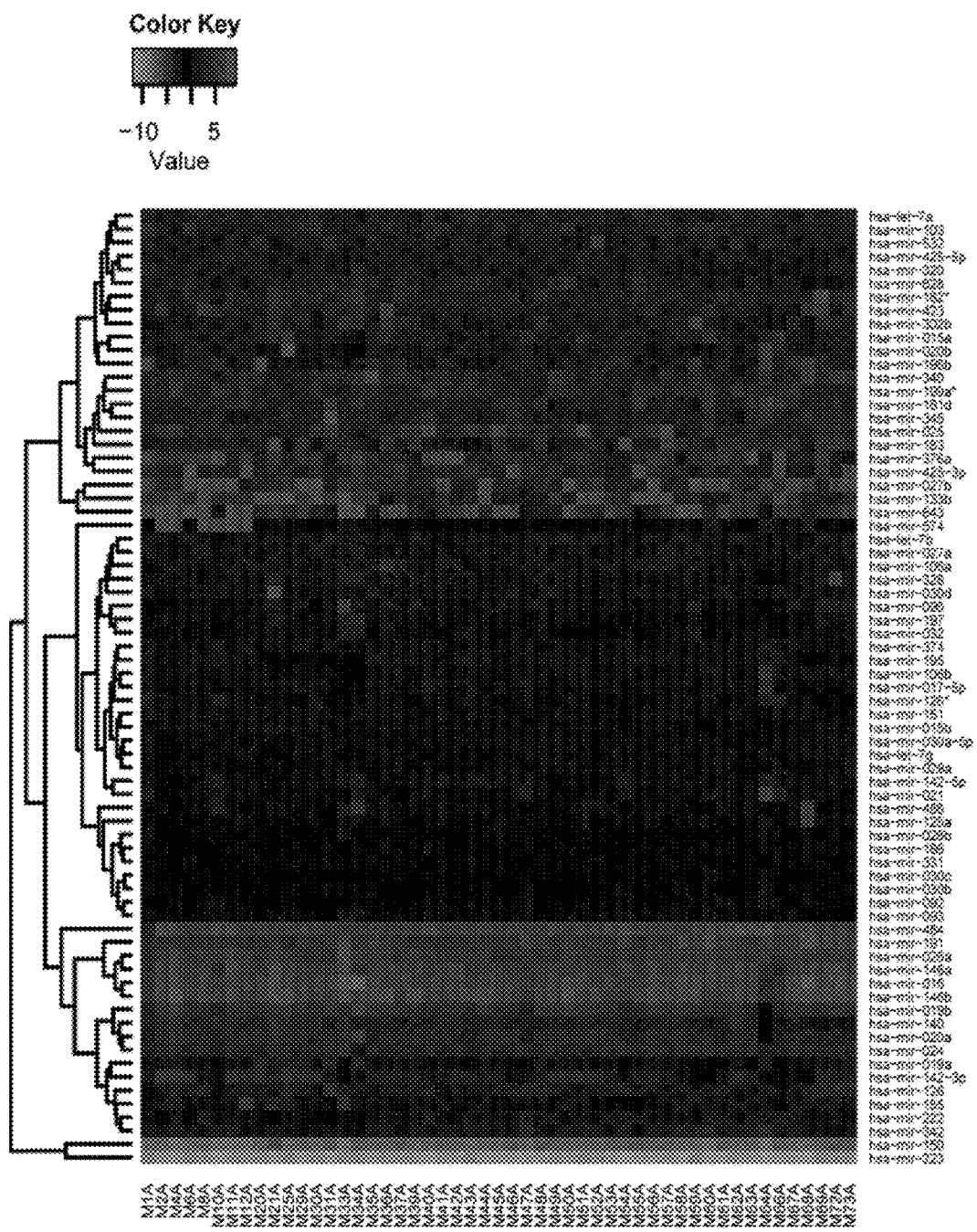

Of these miRNAs, 71 were shared among each sample group (FIG. 5D). Notably, only two miRNAs miR-031 and 29c were expressed solely in the PBMC samples whereas four miRNAs (miR -127, -134, -485-5p, and -432) were uniquely expressed in the plasma fraction. All 104 miRNAs that are normally expressed in the plasma are shown (Table II, shown in FIG. 7).

Age and Gender Effects

We did not observe age and/or gender effects in miRNA expression from either sample group. Notably, the median age for both female and male donors was 29 years. The oldest individual was 58 years old, while the youngest was 21 years of age. Thus, we furthered stratified the data to examine differences. Examination between age-matched samples did not reveal any significant effects on miRNA expression between PBMC and microvesicles samples. While controlling gender, we also compared the upper quartile of age with the lower quartile of age, mean age for each group was 48.9±6.2 and 21.9±1.2, respectively. However, we failed to detect significant differences in miRNA expression between the samples sets based on age (data not shown).

Comparison of miRNA Expression in PBMC and Microvesicles

Shown in Table III, FIG. 8, is the top ten expressed miRNAs in the plasma microvesicles and the PBMC from all individuals. For plasma the top ten expressed miRNAs in descending order are miR-223, -484, -191, -146a, -016, -026a, -222, -024, -126, and -32. Whereas, miR-223, -150, -146b, -016, -484, -146a, -191, -026a, -019b, and -020a were highly expressed in the PBMC. The top ten expressed miRNAs in the microvesicles were detected in 100% of the individuals. However, in the PBMC samples, all but miR-150 (98% of donors) and miR-484 (89% of donors) were observed in 100% of the individuals.

We also found that six of these miRs (miR-223, miR-484, miR-191, miR-146a, miR-26a, and miR-16) are shared among the top ten in both PBMC and microvesicles. Notably, miR-223 is the most prominently expressed miR in both compartments. Based on ranking analysis for each individual donor to determine the frequency in which the specific miRNA appeared in the top ten expressed miRNA, miR-223 had a frequency of 100% in both PBMC and microvesicles. Despite expression of miR-486 being the in the top ten expressed miRNAs in the plasma microvesicles, this miRNA was found to be expressed in the top ten of only 20% of the individuals profiled. Interestingly, the highly expressed miRNAs in the plasma microvesicles were not identified as tissue-specific miRs.

We further examined the collective function of the miRs in microvesicles and PBMC with a ranking score greater than arbitrary values of >66% and >88%, respectively (natural cut-offs from the data set). Based on this criterion, we further examined the top 9 ranked miRs from the microvesicles and PBMC samples. Thus, we analyzed the combined function of miR-223, -484, -191, -146a, -016, -026a, -222, -024, and -126 found in the plasma. For PBMC, we examined the combined function of the following miRNAs, miR-223, -150, -146b, -016, -484, -146a, -191, -026a, and -019b. Using the Sanger miRBase Target version 5, we found 1578 predicted targets of the combined miRs for the plasma microvesicles (data not shown). These combined targets were subjected to computational analysis to determine the pathways that they collectively regulate. Using the Ingenuity Pathway Analysis (IPA) software, we found canonical pathways involved in metabolism and regulation of the acquired immune system were highly regulated by the expression of these shown in miRNAs (Table IV, shown in FIG. 9, top).

Of the nine miRNAs examined from the PBMC fraction, we found 1857 predicted mRNA targets (data not shown). Ultimately the top five canonical pathways regulated by these miRNAs are various amino acid and lipid metabolic pathways, among others (Table IV, shown in FIG. 9, top). We also found common predicted targets from Sanger miRBase and TargetScan and determined their function (Table IV, shown in FIG. 9, bottom).

We next examined which miRNAs were differentially expressed between microvesicles and PBMC. We found 20 miRNAs had more than a three-fold increase in expression in the PBMC fraction compared to the microvesicles samples (Table V, shown in FIG. 10). In contrast, 15 miRNAs were significantly expressed in the plasma microvesicles compared to PBMC.

FIG. 11: Table VI shows the average normalized data for all miRNAs (detector name) expressed in the PBMC and the plasma with standard deviation for each.

Discussion

In these examples, the inventors now show that miRs circulate in microvesicles under normal homeostatic conditions in the peripheral blood. Here, we demonstrate 104 miRs expressed in plasma microvesicles and miR expression was significantly different from PBMC. To date, numerous studies demonstrate the ability of miRs to regulate many cellular functions. However, these studies largely imply that the miR stays within its host cell to elicit an effect (PMID: 17923084). Our data indicates that the miRNAs contained in the microvesicles may be communication signals to distant cells to regulate cellular homeostasis.

These miRNAs in the microvesicles may circulate to different tissue targets. Further examination of the highest expressed miRNAs in the plasma microvesicles, demonstrate that many of these function to regulate hematopoiesis and cellular differentiation programs (Table III, shown in FIG. 8). For instances, expression of miR-223 regulates myeloid, granulocytic and osteoclasts differentiation (PMID: 18278031, PMID: 17471500, PMID: 16325577). It also appears to have a role in hematopoietic stem cell proliferation (PMID: 18278031). Interestingly, miR-223 is loss in acute myelogenous leukemia (AML) (PMID: 18056805). In contrast, downregulation of miR-126 occurs during megakaryocyte differentiation (PMID: 16549775). Notably, expression of miR-24 is regulated by TGF-β which is a potent positive and negative regulator of hematopoiesis (PMID: 16123808, PMID: 18353861). Both miR-24 and miR-16 expressed in the microvesicles regulates red cell production (PMID: 17906079, PMID: 17976518), while miR-16 also modulates lymphoid development (PMID: 16616063). Loss of miR-16 expression has been extensively examined in chronic lymphocytic leukemia (CLL) (PMID: 17327404, PMID: 17351108).

Many miRs expressed in the plasma microvesicles also regulate the progression of the cell cycle proteins (PMID: 18365017 PMID: 17914108). MiR-222 targets p27Kipl (PMID: 17914108) while miR-24 suppresses p16 (INK4a) (PMID: 18365017). Increased expression of miR-16 results in the accumulation of cells in G0/G1 phase of the cell cycle (PMID: 16123808). In contrast, expression of miR-126 in breast cancer cells increases cellular proliferation and tumor growth but inhibits metastases (PMID: 18185580). This occurs through the regulation of vascular cell adhesion molecule-1 (VCAM1) (PMID: 18227515).

Unlike the other miRs highly expressed in the plasma microvesicles, miR-146a appears to function at a different level. While it has been suggested that miR-146a acts as a tumor suppressor and loss of this miR is associated with the development of prostate cancer (PMID: 18174313), miR-146a also modulates immune function (PMID: 16885212, PMID: 18057241). It is possible that expression of this miR in the plasma microvesicles defines immune regulatory function (Table IV, shown in FIG. 9).

Based on IPA analysis examining gene ontology of targets, the top associated networks predicted to be influenced by miR-146a expression is cellular proliferation, immune and lymphatic system development and function. In addition, this miR is predicted to regulate innate immune responses. From the analysis, we found that LPS/IL-1 and toll-like receptor signaling are among the top five canonical pathways predicted to be regulated by this mir-146a.

To date, there is no known function for miR-484 or miR-486. Similar to miR-146a, miR-484 and miR-486 appear to function as a modulator of immune responsiveness. Notably, miR-484 is the second highest expressed miR in the microvesicles fraction based on relative expression. Prediction modeling indicates that this miR has multiple functions. Like many of the other miRs expressed in the microvesicles, miR-484 is predicted to regulate hematopoiesis. In particular, NK cell signaling and IL-4 signaling pathways are predicted to be targets of miR-484, while miR-486 is proposed to regulate antigen presentation. In addition, miR-486 appears to regulate cell differentiation, proliferation and growth.

While we detected 104 miRs in the plasma microvesicles, there were many that were undetectable from the total miRs profiled. Undetectable miRs in plasma microvesicles may also serve as disease biomarkers. Recently, Lawrie et al. reported that miRs were detected in the plasma of patients with B-cell lymphoma (PMID: 18318758). This study, indicated that miR-155, miR-210 and miR-21 were elevated in the plasma from these patients and miR-21 correlated with relapse. Based on this study, we detected miR-155 and miR-21 in normal individuals, but did not find miR-210. Interestingly, we found that 75% of individuals expressed miR-155 and 60% expressed miR-21 in the plasma (data not shown).

Thus, for these miRs to be used as predictive markers of disease, each individual would require a baseline prior to detection of disease. Thus, expression of miR-210 may serve as a better marker of B-cell lymphoma. Additional relationships may exist. For instance, miR-203 was undetectable in plasma microvesicles. Elevated expression of this miR is associated with bladder carcinoma and colon adenocarcinoma and may be thus used as a biomarker (PMID: 18230780, PMID: 17826655).

A converse relation may exist for plasma miRs that are normally expressed then lost with disease. For example, in acute lymphocytic leukemia (ALL), miR-223 is downregulated (PMID: 18056805). Since miR-223 is the most prominent miR expressed in the plasma microvesicles, its reduced expression may be useful as a diagnostic marker in ALL. In addition, miRs-15a/16 are lost or downregulated in chronic lymphocytic leukemia (CLL) (PMID: 18362358). While we found miR-16 was expressed in all healthy individuals that were examined, miR-15a was only expressed in 44% of the individuals profiled (data not shown).

It is of interest that we did not detect tissue specific miRNAs in the blood of normal individuals (PMID: 18025253). The majority of the microvesicles from normal individuals are derived from blood cells. We did detect a small percentage of microvesicles derived from endothelial cells. The endothelial-derived microvesicles may increase upon endothelial cell damage. Likewise, the detection of tissue specific miRs and microvesicles in the peripheral blood may be a frequent event upon tissue damage. Since tumors produce microvesicles (PMID: 16283305), these may be detected in the peripheral blood.

While it has been reported that miRs are detected in the plasma (PMID: 18318758), this is the first study to characterize all known miRs from the plasma. In this study, we controlled race as a factor.

Testing the presence, absence or alterations in levels of miRs in peripheral fluids and/or blood can be useful as biomarkers to examine various diseases, to identify unique miRNA profiles, and to be a predictor of disease. The circulating miRs contained in the microvesicles have a vital function in regulating homeostasis production of blood cells as well as metabolic functions The relevant teachings of all publications cited herein that have not explicitly been incorporated by reference, are incorporated herein by reference in their entirety. While this invention has been particularly shown and described with references to preferred embodiments thereof, it will be understood by those skilled in the art that various changes in form and details may be made therein without departing from the scope of the invention encompassed by the appended claims.

While the invention has been described with reference to various and preferred embodiments, it should be understood by those skilled in the art that various changes may be made and equivalents may be substituted for elements thereof without departing from the essential scope of the invention. In addition, many modifications may be made to adapt a particular situation or material to the teachings of the invention without departing from the essential scope thereof. Therefore, it is intended that the invention not be limited to the particular embodiment disclosed herein contemplated for carrying out this invention, but that the invention will include all embodiments falling within the scope of the claims.

The miRs of interest are listed in public databases. In certain preferred embodiments, the public database can be a central repository provided by the Sanger Institute www.http://microrna.sanger.ac.uk/sequences/to which miR sequences are submitted for naming and nomenclature assignment, as well as placement of the sequences in a database for archiving and for online retrieval via the world wide web. Generally, the data collected on the sequences of miRs by the Sanger Institute include species, source, corresponding genomic sequences and genomic location (chromosomal coordinates), as well as full length transcription products and sequences for the mature fully processed miRNA (miRNA with a 5' terminal phosphate group). Another database can be the GenBank database accessed through the National Center for Biotechnology Information (NCBI) website, maintained by the National Institutes of Health and the National Library of Medicine. These databases are fully incorporated herein by reference.

| microR *Biogenesis byproducts that are at low level, function unknown | miRBase Mature Sequence Accession # | Mature Sequence | SEQ ID NO |
|---|---|---|---|
| hsa-let-7a* | MIMAT0004481 | CUAUACAAUCUACUGUCUUUC | 1 |
| hsa-let-7a-1 | MIMAT0000062 | UGAGGUAGUAGGUUGUAUAGUU | 2 |
| hsa-let-7a-2 | MIMAT0000062 | UGAGGUAGUAGGUUGUAUAGUU | 3 |
| hsa-let-7a-3 | MIMAT0000062 | UGAGGUAGUAGGUUGUAUAGUU | 4 |
| hsa-let-7b | MIMAT0000063 | UGAGGUAGUAGGUUGUGUGGUU | 5 |
| hsa-let-7b* | MIMAT0004482 | CUAUACAACCUACUGCCUUCCC | 6 |
| hsa-let-7c | MIMAT0000064 | UGAGGUAGUAGGUUGUAUGGUU | 7 |
| hsa-let-7c* | MIMAT0004483 | UAGAGUUACACCCUGGGAGUUA | 8 |
| hsa-let-7d | MIMAT0000065 | AGAGGUAGUAGGUUGCAUAGUU | 9 |
| hsa-let-7d* | MIMAT0004484 | CUAUACGACCUGCUGCCUUUCU | 10 |
| hsa-let-7e | MIMAT0000066 | UGAGGUAGGAGGUUGUAUAGUU | 11 |
| hsa-let-7e* | MIMAT0004485 | CUAUACGGCCUCCUAGCUUUCC | 12 |
| hsa-let-7f-1 | MIMAT0000067 | UGAGGUAGUAGAUUGUAUAGUU | 13 |
| hsa-let-7f-1* | MIMAT0004486 | CUAUACAAUCUAUUGCCUUCCC | 14 |
| hsa-let-7f-2 | MIMAT0000067 | UGAGGUAGUAGAUUGUAUAGUU | 15 |
| hsa-let-7f-2* | MIMAT0004487 | CUAUACAGUCUACUGUCUUUCC | 16 |
| hsa-let-7g | MIMAT0000414 | UGAGGUAGUAGUUUGUACAGUU | 17 |
| hsa-let-7g* | MIMAT0004584 | CUGUACAGGCCACUGCCUUGC | 18 |
| hsa-let-7i | MIMAT0000415 | UGAGGUAGUAGUUUGUGCUGUU | 19 |
| hsa-let-7i* | MIMAT0004585 | CUGCGCAAGCUACUGCCUUGCU | 20 |
| hsa-mir-009-1 | MIMAT0000441 | UCUUUGGUUAUCUAGCUGUAUGA | 21 |
| hsa-mir-009-1* | MIMAT0000442 | AUAAAGCUAGAUAACCGAAAGU | 22 |
| hsa-mir-009-2 | MIMAT0000441 | UCUUUGGUUAUCUAGCUGUAUGA | 23 |
| hsa-mir-009-3 | MIMAT0000441 | UCUUUGGUUAUCUAGCUGUAUGA | 24 |
| hsa-mir-010a | MIMAT0000253 | UACCCUGUAGAUCCGAAUUUGUG | 25 |
| hsa-mir-010a* | MIMAT0004555 | CAAAUUCGUAUCUAGGGGAAUA | 26 |
| hsa-mir-015a | MIMAT0000068 | UAGCAGCACAUAAUGGUUUGUG | 27 |
| hsa-mir-015b | MIMAT0000417 | UAGCAGCACAUCAUGGUUUACA | 28 |
| hsa-mir-015b* | MIMAT0004586 | CGAAUCAUUAUUUGCUGCUCUA | 29 |
| hsa-mir-016-1 | MIMAT0000069 | UAGCAGCACGUAAAUAUUGGCG | 30 |
| hsa-mir-016-1* | MIMAT0004489 | CCAGUAUUAACUGUGCUGCUGA | 31 |
| hsa-mir-016-2 | MIMAT0000069 | UAGCAGCACGUAAAUAUUGGCG | 32 |
| hsa-mir-016-2* | MIMAT0004518 | CCAAUAUUACUGUGCUGCUUUA | 33 |
| hsa-mir-017-3-p | MIMAT0000071 | ACUGCAGUGAAGGCACUUGUAG | 34 |
| hsa-mir-017-5-p | MIMAT0000070 | CAAAGUGCUUACAGUGCAGGUAG | 35 |
| hsa-mir-018a | MIMAT0000072 | UAAGGUGCAUCUAGUGCAGAUAG | 36 |
| hsa-mir-018a* | MIMAT0002891 | ACUGCCCUAAGUGCUCCUUCUGG | 37 |
| hsa-mir-019a | MIMAT0000073 | UGUGCAAAUCUAUGCAAAACUGA | 38 |

-continued

| microR *Biogenesis byproducts that are at low level, function unknown | miRBase Mature Sequence Accession # | Mature Sequence | SEQ ID NO |
|---|---|---|---|
| hsa-mir-019b-1 | MIMAT0000074 | UGUGCAAAUCCAUGCAAAACUGA | 39 |
| hsa-mir-019b-1* | MIMAT0004491 | AGUUUUGCAGGUUUGCAUCCAGC | 40 |
| hsa-mir-019b-2 | MIMAT0000074 | UGUGCAAAUCCAUGCAAAACUGA | 41 |
| hsa-mir-019b-2* | MIMAT0004492 | AGUUUUGCAGGUUUGCAUUUCA | 42 |
| hsa-mir-020a | MIMAT0000075 | UAAAGUGCUUAUAGUGCAGGUAG | 43 |
| hsa-mir-020a* | MIMAT0004493 | ACUGCAUUAUGAGCACUUAAAG | 44 |
| hsa-mir-020b | MIMAT0001413 | CAAAGUGCUCAUAGUGCAGGUAG | 45 |
| hsa-mir-021 | MIMAT0000076 | UAGCUUAUCAGACUGAUGUUGA | 46 |
| hsa-mir-021* | MIMAT0004494 | CAACACCAGUCGAUGGGCUGU | 47 |
| hsa-mir-023a | MIMAT0000078 | AUCACAUUGCCAGGGAUUUCC | 48 |
| hsa-mir-023a* | MIMAT0004496 | GGGGUUCCUGGGGAUGGGAUUU | 49 |
| hsa-mir-023b | MIMAT0004587 | UGGGUUCCUGGCAUGCUGAUUU | 50 |
| hsa-mir-024-1 | MIMAT0000080 | UGGCUCAGUUCAGCAGGAACAG | 51 |
| hsa-mir-024-1* | MIMAT0000079 | UGCCUACUGAGCUGAUAUCAGU | 52 |
| hsa-mir-024-2 | MIMAT0000080 | UGGCUCAGUUCAGCAGGAACAG | 53 |
| hsa-mir-024-2* | MIMAT0004497 | UGCCUACUGAGCUGAAACACAG | 54 |
| hsa-mir-025 | MIMAT0000081 | CAUUGCACUUGUCUCGGUCUGA | 55 |
| hsa-mir-025* | MIMAT0004498 | AGGCGGAGACUUGGGCAAUUG | 56 |
| hsa-mir-026a-1 | MIMAT0000082 | UUCAAGUAAUCCAGGAUAGGCU | 57 |
| hsa-mir-026a-1* | MIMAT0004499 | CCUAUUCUUGGUUACUUGCACG | 58 |
| hsa-mir-026a-2 | MIMAT0000082 | UUCAAGUAAUCCAGGAUAGGCU | 59 |
| hsa-mir-026a-2* | MIMAT0004681 | CCUAUUCUUGAUUACUUGUUUC | 60 |
| hsa-mir-026b | MIMAT0000083 | UUCAAGUAAUUCAGGAUAGGU | 61 |
| hsa-mir-026b* | MIMAT0004500 | CCUGUUCUCCAUUACUUGGCUC | 62 |
| hsa-mir-027a | MIMAT0000084 | UUCACAGUGGCUAAGUUCCGC | 63 |
| hsa-mir-027a* | MIMAT0004501 | AGGGCUUAGCUGCUUGUGAGCA | 64 |
| hsa-mir-027b | MIMAT0000419 | UUCACAGUGGCUAAGUUCUGC | 65 |
| hsa-mir-027b* | MIMAT0004588 | AGAGCUUAGCUGAUUGGUGAAC | 66 |
| hsa-mir-028-3p | MIMAT0004502 | CACUAGAUUGUGAGCUCCUGGA | 67 |
| hsa-mir-028-5p | MIMAT0000085 | AAGGAGCUCACAGUCUAUUGAG | 68 |
| hsa-mir-029a | MIMAT0000086 | UAGCACCAUCUGAAAUCGGUUA | 69 |
| hsa-mir-029a* | MIMAT0004503 | ACUGAUUUCUUUUGGUGUUCAG | 70 |
| hsa-mir-029b-1 | MIMAT0000100 | UAGCACCAUUUGAAAUCAGUGUU | 71 |
| hsa-mir-029b-1* | MIMAT0004514 | GCUGGUUUCAUAUGGUGGUUUAGA | 72 |
| hsa-mir-029b-2 | MIMAT0000100 | UAGCACCAUUUGAAAUCAGUGUU | 73 |
| hsa-mir-029b-2* | MIMAT0004515 | CUGGUUUCACAUGGUGGCUUAG | 74 |

-continued

| microR *Biogenesis byproducts that are at low level, function unknown | miRBase Mature Sequence Accession # | Mature Sequence | SEQ ID NO |
|---|---|---|---|
| hsa-mir-029b-3 | MIMAT0000100 | UAGCACCAUUUGAAAUCAGUGUU | 75 |
| hsa-mir-029c | MIMAT0000681 | UAGCACCAUUUGAAAUCGGUUA | 76 |
| hsa-mir-030a | MIMAT0000087 | UGUAAACAUCCUCGACUGGAAG | 77 |
| hsa-mir-030a* | MIMAT0000088 | CUUUCAGUCGGAUGUUUGCAGC | 78 |
| hsa-mir-030b | MIMAT0000420 | UGUAAACAUCCUACACUCAGCU | 79 |
| hsa-mir-030b* | MIMAT0004589 | CUGGGAGGUGGAUGUUUACUUC | 80 |
| hsa-mir-030c-1 | MIMAT0000244 | UGUAAACAUCCUACACUCUCAGC | 81 |
| hsa-mir-030c-2 | MIMAT0000244 | UGUAAACAUCCUACACUCUCAGC | 82 |
| hsa-mir-030c-2* | MIMAT0004550 | CUGGGAGAAGGCUGUUUACUCU | 83 |
| hsa-mir-030d | MIMAT0000245 | UGUAAACAUCCCCGACUGGAAG | 84 |
| hsa-mir-030d* | MIMAT0004551 | CUUUCAGUCAGAUGUUUGCUGC | 85 |
| hsa-mir-031 | MIMAT0000089 | AGGCAAGAUGCUGGCAUAGCU | 86 |
| hsa-mir-031* | MIMAT0004504 | UGCUAUGCCAACAUAUUGCCAU | 87 |
| hsa-mir-032 | MIMAT0000090 | UAUUGCACAUUACUAAGUUGCA | 88 |
| hsa-mir-032* | MIMAT0004505 | CAAUUUAGUGUGUGUGAUAUUU | 89 |
| hsa-mir-034a | MIMAT0000255 | UGGCAGUGUCUUAGCUGGUUGU | 90 |
| hsa-mir-034a* | MIMAT0004557 | CAAUCAGCAAGUAUACUGCCCU | 91 |
| hsa-mir-092a-1 | MIMAT0000092 | UAUUGCACUUGUCCCGGCCUGU | 92 |
| hsa-mir-092a-1* | MIMAT0004507 | AGGUUGGGAUCGGUUGCAAUGCU | 93 |
| hsa-mir-093 | MIMAT0000093 | CAAAGUGCUGUUCGUGCAGGUAG | 94 |
| hsa-mir-093* | MIMAT0004509 | ACUGCUGAGCUAGCACUUCCCG | 95 |
| hsa-mir-095 | MIMAT0000094 | UUCAACGGGUAUUUAUUGAGCA | 96 |
| hsa-mir-096 | MIMAT0000095 | UUUGGCACUAGCACAUUUUUGCU | 97 |
| hsa-mir-096* | MIMAT0004510 | AAUCAUGUGCAGUGCCAAUAUG | 98 |
| hsa-mir-098 | MIMAT0000096 | UGAGGUAGUAAGUUGUAUUGUU | 99 |
| hsa-mir-099b | MIMAT0000689 | CACCCGUAGAACCGACCUUGCG | 100 |
| hsa-mir-099b* | MIMAT0004678 | CAAGCUCGUGUCUGUGGGUCCG | 101 |
| hsa-mir-100 | MIMAT0000098 | AACCCGUAGAUCCGAACUUGUG | 102 |
| hsa-mir-100* | MIMAT0004512 | CAAGCUUGUAUCUAUAGGUAUG | 103 |
| hsa-mir-103-1 | MIMAT0000101 | AGCAGCAUUGUACAGGGCUAUGA | 104 |
| hsa-mir-103-2 | MIMAT0000101 | AGCAGCAUUGUACAGGGCUAUGA | 105 |
| hsa-mir-105-1 | MIMAT0000102 | UCAAAUGCUCAGACUCCUGUGGU | 106 |
| hsa-mir-105-1* | MIMAT0004516 | ACGGAUGUUUGAGCAUGUGCUA | 107 |
| hsa-mir-105-2 | MIMAT0000102 | UCAAAUGCUCAGACUCCUGUGGU | 108 |
| hsa-mir-105-2* | MIMAT0004516 | ACGGAUGUUUGAGCAUGUGCUA | 109 |
| hsa-mir-106a | MIMAT0000103 | AAAAGUGCUUACAGUGCAGGUAG | 110 |
| hsa-mir-106a* | MIMAT0004517 | CUGCAAUGUAAGCACUUCUUAC | 111 |

-continued

| microR *Biogenesis byproducts that are at low level, function unknown | miRBase Mature Sequence Accession # | Mature Sequence | SEQ ID NO |
|---|---|---|---|
| hsa-mir-106b | MIMAT0000680 | UAAAGUGCUGACAGUGCAGAU | 112 |
| hsa-mir-106b* | MIMAT0004672 | CCGCACUGUGGGUACUUGCUGC | 113 |
| hsa-mir-107 | MIMAT0000104 | AGCAGCAUUGUACAGGGCUAUCA | 114 |
| hsa-mir-122 | MIMAT0000421 | UGGAGUGUGACAAUGGUGUUUG | 115 |
| hsa-mir-122* | MIMAT0004590 | AACGCCAUUAUCACACUAAAUA | 116 |
| hsa-mir-125a-3p | MIMAT0004602 | ACAGGUGAGGUUCUUGGGAGCC | 117 |
| hsa-mir-125a-5p | MIMAT0000443 | UCCCUGAGACCCUUUAACCUGUGA | 118 |
| hsa-mir-125b-1 | MIMAT0000423 | UCCCUGAGACCCUAACUUGUGA | 119 |
| hsa-mir-125b-1* | MIMAT0004592 | ACGGGUUAGGCUCUUGGGAGCU | 120 |
| hsa-mir-125b-2 | MIMAT0000423 | UCCCUGAGACCCUAACUUGUGA | 121 |
| hsa-mir-125b-2* | MIMAT0004603 | UCACAAGUCAGGCUCUUGGGAC | 122 |
| hsa-mir-126 | MIMAT0000445 | UCGUACCGUGAGUAAUAAUGCG | 123 |
| hsa-mir-126* | MIMAT0000444 | CAUUAUUACUUUUGGUACGCG | 124 |
| hsa-mir-127-3p | MIMAT0000446 | UCGGAUCCGUCUGAGCUUGGCU | 125 |
| hsa-mir-127-5p | MIMAT0004604 | CUGAAGCUCAGAGGGCUCUGAU | 126 |
| hsa-mir-128-1 | MIMAT0000424 | UCACAGUGAACCGGUCUCUUU | 127 |
| hsa-mir-128-2 | MIMAT0000424 | UCACAGUGAACCGGUCUCUUU | 128 |
| hsa-mir-130a | MIMAT0000425 | CAGUGCAAUGUUAAAGGGCAU | 129 |
| hsa-mir-130a* | MIMAT0004593 | UUCACAUUGUGCUACUGUCUGC | 130 |
| hsa-mir-130b | MIMAT0000691 | CAGUGCAAUGAUGAAAGGGCAU | 131 |
| hsa-mir-130b* | MIMAT0004680 | ACUCUUUCCCUGUUGCACUAC | 132 |
| hsa-mir-132 | MIMAT0000426 | UAACAGUCUACAGCCAUGGUCG | 133 |
| hsa-mir-132* | MIMAT0004594 | ACCGUGGCUUUCGAUUGUUACU | 134 |
| hsa-mir-133a-1 | MIMAT0000427 | UUUGGUCCCCUUCAACCAGCUG | 135 |
| hsa-mir-133a-2 | MIMAT0000427 | UUUGGUCCCCUUCAACCAGCUG | 136 |
| hsa-mir-133b | MIMAT0000770 | UUUGGUCCCCUUCAACCAGCUA | 137 |
| hsa-mir-134 | MIMAT0000447 | UGUGACUGGUUGACCAGAGGGG | 138 |
| hsa-mir-135b | MIMAT0000758 | UAUGGCUUUUCAUUCCUAUGUGA | 139 |
| hsa-mir-135b* | MIMAT0004698 | AUGUAGGGCUAAAAGCCAUGGG | 140 |
| hsa-mir-140-3p | MIMAT0004597 | UACCACAGGGUAGAACCACGG | 141 |
| hsa-mir-140-5p | MIMAT0000431 | CAGUGGUUUUACCCUAUGGUAG | 142 |
| hsa-mir-142-3p | MIMAT0000434 | UGUAGUGUUUCCUACUUUAUGGA | 143 |
| hsa-mir-142-5p | MIMAT0000433 | CAUAAAGUAGAAAGCACUACU | 144 |
| hsa-mir-143 | MIMAT0000435 | UGAGAUGAAGCACUGUAGCUC | 145 |
| hsa-mir-143* | MIMAT0004599 | GGUGCAGUGCUGCAUCUCUGGU | 146 |
| hsa-mir-145 | MIMAT0000437 | GUCCAGUUUUCCCAGGAAUCCCU | 147 |

-continued

| microR *Biogenesis byproducts that are at low level, function unknown | miRBase Mature Sequence Accession # | Mature Sequence | SEQ ID NO |
|---|---|---|---|
| hsa-mir-145* | MIMAT0004601 | GGAUUCCUGGAAAUACUGUUCU | 148 |
| hsa-mir-146a | MIMAT0000449 | UGAGAACUGAAUUCCAUGGGUU | 149 |
| hsa-mir-146a* | MIMAT0004608 | CCUCUGAAAUUCAGUUCUUCAG | 150 |
| hsa-mir-146b-3p | MIMAT0004766 | UGCCCUGUGGACUCAGUUCUGG | 151 |
| hsa-mir-146b-5p | MIMAT0002809 | UGAGAACUGAAUUCCAUAGGCU | 152 |
| hsa-mir-147 | MIMAT0000251 | GUGUGUGGAAAUGCUUCUGC | 153 |
| hsa-mir-148a | MIMAT0000243 | UCAGUGCACUACAGAACUUUGU | 154 |
| hsa-mir-148a* | MIMAT0004549 | AAAGUUCUGAGACACUCCGACU | 155 |
| hsa-mir-148b | MIMAT0000759 | UCAGUGCAUCACAGAACUUUGU | 156 |
| hsa-mir-148b* | MIMAT0004699 | AAGUUCUGUUAUACACUCAGGC | 157 |
| hsa-mir-149 | MIMAT0000450 | UCUGGCUCCGUGUCUUCACUCCC | 158 |
| hsa-mir-149* | MIMAT0004609 | AGGGAGGGACGGGGGCUGUGC | 159 |
| hsa-mir-150 | MIMAT0000451 | UCUCCCAACCCUUGUACCAGUG | 160 |
| hsa-mir-150* | MIMAT0004610 | CUGGUACAGGCCUGGGGACAG | 161 |
| hsa-mir-151-3p | MIMAT0000757 | CUAGACUGAAGCUCCUUGAGG | 162 |
| hsa-mir-151-5p | MIMAT0004697 | UCGAGGAGCUCACAGUCUAGU | 163 |
| hsa-mir-155 | MIMAT0000646 | UUAAUGCUAAUCGUGAUAGGGGU | 164 |
| hsa-mir-155* | MIMAT0004658 | CUCCUACAUAUUAGCAUUAACA | 165 |
| hsa-mir-181a-1 | MIMAT0000256 | AACAUUCAACGCUGUCGGUGAGU | 166 |
| hsa-mir-181a-1* | MIMAT0000270 | ACCAUCGACCGUUGAUUGUACC | 167 |
| hsa-mir-181a-2 | MIMAT0000256 | AACAUUCAACGCUGUCGGUGAGU | 168 |
| hsa-mir-181a-2* | MIMAT0004558 | ACCACUGACCGUUGACUGUACC | 169 |
| hsa-mir-181b-1 | MIMAT0000257 | AACAUUCAUUGCUGUCGGUGGGU | 170 |
| hsa-mir-181b-2 | MIMAT0000257 | AACAUUCAUUGCUGUCGGUGGGU | 171 |
| hsa-mir-181d | MIMAT0002821 | AACAUUCAUUGUUGUCGGUGGGU | 172 |
| hsa-mir-182 | MIMAT0000259 | UUUGGCAAUGGUAGAACUCACACU | 173 |
| hsa-mir-182* | MIMAT0000260 | UGGUUCUAGACUUGCCAACUA | 174 |
| hsa-mir-183 | MIMAT0000261 | UAUGGCACUGGUAGAAUUCACU | 175 |
| hsa-mir-183* | MIMAT0004560 | GUGAAUUACCGAAGGGCCAUAA | 176 |
| hsa-mir-185 | MIMAT0000455 | UGGAGAGAAAGGCAGUUCCUGA | 177 |
| hsa-mir-185* | MIMAT0004611 | AGGGGCUGGCUUUCCUCUGGUC | 178 |
| hsa-mir-186 | MIMAT0000456 | CAAAGAAUUCUCCUUUUGGGCU | 179 |
| hsa-mir-186* | MIMAT0004612 | GCCCAAAGGUGAAUUUUUUGGG | 180 |
| hsa-mir-190 | MIMAT0000458 | UGAUAUGUUUGAUAUAUUAGGU | 181 |
| hsa-mir-191 | MIMAT0000440 | CAACGGAAUCCCAAAAGCAGCUG | 182 |
| hsa-mir-191* | MIMAT0001618 | GCUGCGCUUGGAUUUCGUCCCC | 183 |
| hsa-mir-192 | MIMAT0000222 | CUGACCUAUGAAUUGACAGCC | 184 |

-continued

| microR *Biogenesis byproducts that are at low level, function unknown | miRBase Mature Sequence Accession # | Mature Sequence | SEQ ID NO |
|---|---|---|---|
| hsa-mir-192* | MIMAT0004543 | CUGCCAAUUCCAUAGGUCACAG | 185 |
| hsa-mir-193a-3p | MIMAT0000459 | AACUGGCCUACAAAGUCCCAGU | 186 |
| hsa-mir-193a-5p | MIMAT0004614 | UGGGUCUUUGCGGGCGAGAUGA | 187 |
| hsa-mir-193b | MIMAT0002819 | AACUGGCCCUCAAAGUCCCGCU | 188 |
| hsa-mir-193b* | MIMAT0004767 | CGGGGUUUUGAGGGCGAGAUGA | 189 |
| hsa-mir-195 | MIMAT0000461 | UAGCAGCACAGAAAUAUUGGC | 190 |
| hsa-mir-195* | MIMAT0004615 | CCAAUAUUGGCUGUGCUGCUCC | 191 |
| hsa-mir-196a* | MIMAT0004562 | CGGCAACAAGAAACUGCCUGAG | 192 |
| hsa-mir-196a-1 | MIMAT0000226 | UAGGUAGUUUCAUGUUGUUGGG | 193 |
| hsa-mir-196a-2 | MIMAT0000226 | UAGGUAGUUUCAUGUUGUUGGG | 194 |
| hsa-mir-196b | MIMAT0001080 | UAGGUAGUUUCCUGUUGUUGGG | 195 |
| hsa-mir-197 | MIMAT0000227 | UUCACCACCUUCUCCACCCAGC | 196 |
| hsa-mir-198 | MIMAT0000228 | GGUCCAGAGGGGAGAUAGGUUC | 197 |
| hsa-mir-199a-3p | MIMAT0000232 | ACAGUAGUCUGCACAUUGGUUA | 198 |
| hsa-mir-199a-5p | MIMAT0000231 | CCCAGUGUUCAGACUACCUGUUC | 199 |
| hsa-mir-199a-5p | MIMAT0000231 | CCCAGUGUUCAGACUACCUGUUC | 200 |
| hsa-mir-199b-3p | MIMAT0004563 | ACAGUAGUCUGCACAUUGGUUA | 201 |
| hsa-mir-199b-5p | MIMAT0000263 | CCCAGUGUUUAGACUAUCUGUUC | 202 |
| hsa-mir-200a | MIMAT0000682 | UAACACUGUCUGGUAACGAUGU | 203 |
| hsa-mir-200a* | MIMAT0001620 | CAUCUUACCGGACAGUGCUGGA | 204 |
| hsa-mir-200b | MIMAT0000318 | UAAUACUGCCUGGUAAUGAUGA | 205 |
| hsa-mir-200b* | MIMAT0004571 | CAUCUUACUGGGCAGCAUUGGA | 206 |
| hsa-mir-200c | MIMAT0000617 | UAAUACUGCCGGGUAAUGAUGGA | 207 |
| hsa-mir-200c* | MIMAT0004657 | CGUCUUACCCAGCAGUGUUUGG | 208 |
| hsa-mir-203 | MIMAT0000264 | GUGAAAUGUUUAGGACCACUAG | 209 |
| hsa-mir-204 | MIMAT0000265 | UUCCCUUUGUCAUCCUAUGCCU | 210 |
| hsa-mir-205 | MIMAT0000266 | UCCUUCAUUCCACCGGAGUCUG | 211 |
| hsa-mir-210 | MIMAT0000267 | CUGUGCGUGUGACAGCGGCUGA | 212 |
| hsa-mir-213 | MIMAT0000256 | AACAUUCAACGCUGUCGGUGAGU | 213 |
| hsa-mir-214 | MIMAT0000271 | ACAGCAGGCACAGACAGGCAGU | 214 |
| hsa-mir-214* | MIMAT0004564 | UGCCUGUCUACACUUGCUGUGC | 215 |
| hsa-mir-216a | MIMAT0000273 | UAAUCUCAGCUGGCAACUGUGA | 216 |
| hsa-mir-216b | MIMAT0004959 | AAAUCUCUGCAGGCAAAUGUGA | 217 |
| hsa-mir-217 | MIMAT0000274 | UACUGCAUCAGGAACUGAUUGGA | 218 |
| hsa-mir-218-1 | MIMAT0000275 | UUGUGCUUGAUCUAACCAUGU | 219 |
| hsa-mir-218-1* | MIMAT0004565 | AUGGUUCCGUCAAGCACCAUGG | 220 |

| microR *Biogenesis byproducts that are at low level, function unknown | miRBase Mature Sequence Accession # | Mature Sequence | SEQ ID NO |
|---|---|---|---|
| hsa-mir-218-2 | MIMAT0000275 | UUGUGCUUGAUCUAACCAUGU | 221 |
| hsa-mir-218-2* | MIMAT0004566 | CAUGGUUCUGUCAAGCACCGCG | 222 |
| hsa-mir-221 | MIMAT0000278 | AGCUACAUUGUCUGCUGGGUUUC | 223 |
| hsa-mir-221* | MIMAT0004568 | ACCUGGCAUACAAUGUAGAUUU | 224 |
| hsa-mir-222 | MIMAT0000279 | AGCUACAUCUGGCUACUGGGU | 225 |
| hsa-mir-222* | MIMAT0004569 | CUCAGUAGCCAGUGUAGAUCCU | 226 |
| hsa-mir-223 | MIMAT0000280 | UGUCAGUUUGUCAAAUACCCCA | 227 |
| hsa-mir-223* | MIMAT0004570 | CGUGUAUUUGACAAGCUGAGUU | 228 |
| hsa-mir-224 | MIMAT0000281 | CAAGUCACUAGUGGUUCCGUU | 229 |
| hsa-mir-302a | MIMAT0000684 | UAAGUGCUUCCAUGUUUUGGUGA | 230 |
| hsa-mir-302a* | MIMAT0000683 | ACUUAAACGUGGAUGUACUUGCU | 231 |
| hsa-mir-302b | MIMAT0000715 | UAAGUGCUUCCAUGUUUUAGUAG | 232 |
| hsa-mir-302b* | MIMAT0000714 | ACUUUAACAUGGAAGUGCUUUC | 233 |
| hsa-mir-302c | MIMAT0000717 | UAAGUGCUUCCAUGUUUCAGUGG | 234 |
| hsa-mir-302c* | MIMAT0000716 | UUUAACAUGGGGGUACCUGCUG | 235 |
| hsa-mir-302d | MIMAT0000718 | UAAGUGCUUCCAUGUUUGAGUGU | 236 |
| hsa-mir-302d* | MIMAT0004685 | ACUUUAACAUGGAGGCACUUGC | 237 |
| hsa-mir-302e | MIMAT0005931 | UAAGUGCUUCCAUGCUU | 238 |
| hsa-mir-302f | MIMAT0005932 | UAAUUGCUUCCAUGUUU | 239 |
| hsa-mir-320a | MIMAT0000510 | AAAAGCUGGGUUGAGAGGGCGA | 240 |
| hsa-mir-320b-1 | MIMAT0005792 | AAAAGCUGGGUUGAGAGGGCAA | 241 |
| hsa-mir-320b-2 | MIMAT0005792 | AAAAGCUGGGUUGAGAGGGCAA | 242 |
| hsa-mir-320c-1 | MIMAT0005793 | AAAAGCUGGGUUGAGAGGGU | 243 |
| hsa-mir-320c-2 | MIMAT0005793 | AAAAGCUGGGUUGAGAGGGU | 244 |
| hsa-mir-320d-1 | MIMAT0006764 | AAAAGCUGGGUUGAGAGGA | 245 |
| hsa-mir-320d-2 | MIMAT0006764 | AAAAGCUGGGUUGAGAGGA | 246 |
| hsa-mir-324-3p | MIMAT0000762 | ACUGCCCCAGGUGCUGCUGG | 247 |
| hsa-mir-324-5p | MIMAT0000761 | CGCAUCCCCUAGGGCAUUGGUGU | 248 |
| hsa-mir-326 | MIMAT0000756 | CCUCUGGGCCCUUCCUCCAG | 249 |
| hsa-mir-328 | MIMAT0000752 | CUGGCCCUCUCUGCCCUUCCGU | 250 |
| hsa-mir-330-3p | MIMAT0000751 | GCAAAGCACACGGCCUGCAGAGA | 251 |
| hsa-mir-330-5p | MIMAT0004693 | UCUCUGGGCCUGUGUCUUAGGC | 252 |
| hsa-mir-331-3p | MIMAT0000760 | GCCCCUGGGCCUAUCCUAGAA | 253 |
| hsa-mir-331-5p | MIMAT0004700 | CUAGGUAUGGUCCCAGGGAUCC | 254 |
| hsa-mir-335 | MIMAT0000765 | UCAAGAGCAAUAACGAAAAAUGU | 255 |
| hsa-mir-335* | MIMAT0004703 | UUUUUCAUUAUUGCUCCUGACC | 256 |
| hsa-mir-339-3p | MIMAT0004702 | UGAGCGCCUCGACGACAGAGCCG | 257 |

| microR *Biogenesis byproducts that are at low level, function unknown | miRBase Mature Sequence Accession # | Mature Sequence | SEQ ID NO |
|---|---|---|---|
| hsa-mir-339-5p | MIMAT0000764 | UCCCUGUCCUCCAGGAGCUCACG | 258 |
| hsa-mir-340 | MIMAT0004692 | UUAUAAAGCAAUGAGACUGAUU | 259 |
| hsa-mir-340* | MIMAT0000750 | UCCGUCUCAGUUACUUUAUAGC | 260 |
| hsa-mir-342-3p | MIMAT0000753 | UCUCACACAGAAAUCGCACCCGU | 261 |
| hsa-mir-342-5p | MIMAT0004694 | AGGGGUGCUAUCUGUGAUUGA | 262 |
| hsa-mir-345 | MIMAT0000772 | GCUGACUCCUAGUCCAGGGCUC | 263 |
| hsa-mir-361-3p | MIMAT0004682 | UCCCCCAGGUGUGAUUCUGAUUU | 264 |
| hsa-mir-361-5p | MIMAT0000703 | UUAUCAGAAUCUCCAGGGGUAC | 265 |
| hsa-mir-370 | MIMAT0000722 | GCCUGCUGGGGUGGAACCUGGU | 266 |
| hsa-mir-374a | MIMAT0000727 | UUAUAAUACAACCUGAUAAGUG | 267 |
| hsa-mir-374b | MIMAT0004955 | AUAUAAUACAACCUGCUAAGUG | 268 |
| hsa-mir-376a* | MIMAT0003386 | GUAGAUUCUCCUUCUAUGAGUA | 269 |
| hsa-mir-376a-1 | MIMAT0000729 | AUCAUAGAGGAAAAUCCACGU | 270 |
| hsa-mir-376a-2 | MIMAT0000729 | AUCAUAGAGGAAAAUCCACGU | 271 |
| hsa-mir-376b | MIMAT0002172 | AUCAUAGAGGAAAAUCCAUGUU | 272 |
| hsa-mir-376c | MIMAT0000720 | AACAUAGAGGAAAUUCCACGU | 273 |
| hsa-mir-378 | MIMAT0000732 | ACUGGACUUGGAGUCAGAAGG | 274 |
| hsa-mir-378* | MIMAT0000731 | CUCCUGACUCCAGGUCCUGUGU | 275 |
| hsa-mir-382 | MIMAT0000737 | GAAGUUGUUCGUGGUGGAUUCG | 276 |
| hsa-mir-411 | MIMAT0003329 | UAGUAGACCGUAUAGCGUACG | 277 |
| hsa-mir-411* | MIMAT0004813 | UAUGUAACACGGUCCACUAACC | 278 |
| hsa-mir-423 | MIMAT0004748 | UGAGGGGCAGAGAGCGAGACUUU | 279 |
| hsa-mir-423* | MIMAT0001340 | AGCUCGGUCUGAGGCCCCUCAGU | 280 |
| hsa-mir-425-3p | MIMAT0001343 | AUCGGGAAUGUCGUGUCCGCCC | 281 |
| hsa-mir-425-5p | MIMAT0003393 | AAUGACACGAUCACUCCCGUUGA | 282 |
| hsa-mir-432 | MIMAT0002814 | UCUUGGAGUAGGUCAUUGGGUGG | 283 |
| hsa-mir-432* | MIMAT0002815 | CUGGAUGGCUCCUCCAUGUCU | 284 |
| hsa-mir-433 | MIMAT0001627 | AUCAUGAUGGGCUCCUCGGUGU | 285 |
| hsa-mir-484 | MIMAT0002174 | UCAGGCUCAGUCCCCUCCCGAU | 286 |
| hsa-mir-485-3p | MIMAT0002176 | GUCAUACACGGCUCUCCUCUCU | 287 |
| hsa-mir-485-5p | MIMAT0002175 | AGAGGCUGGCCGUGAUGAAUUC | 288 |
| hsa-mir-486-3p | MIMAT0004762 | CGGGGCAGCUCAGUACAGGAU | 289 |
| hsa-mir-486-5p | MIMAT0002177 | UCCUGUACUGAGCUGCCCCGAG | 290 |
| hsa-mir-487a | MIMAT0002178 | AAUCAUACAGGGACAUCCAGUU | 291 |
| hsa-mir-487b | MIMAT0003180 | AAUCGUACAGGGUCAUCCACUU | 292 |
| hsa-mir-532 | MIMAT0002888 | CAUGCCUUGAGUGUAGGACCGU | 293 |

| microR *Biogenesis byproducts that are at low level, function unknown | miRBase Mature Sequence Accession # | Mature Sequence | SEQ ID NO |
|---|---|---|---|
| hsa-mir-532-5p | MIMAT0004780 | CCUCCCACACCCAAGGCUUGCA | 294 |
| hsa-mir-539 | MIMAT0003163 | GGAGAAAUUAUCCUUGGUGUGU | 295 |
| hsa-mir-574-3p | MIMAT0003239 | CACGCUCAUGCACACACCCACA | 296 |
| hsa-mir-574-5p | MIMAT0004795 | UGAGUGUGUGUGUGUGAGUGUGU | 297 |
| hsa-mir-584 | MIMAT0003249 | UUAUGGUUUGCCUGGGACUGAG | 298 |
| hsa-mir-628-3p | MIMAT0003297 | UCUAGUAAGAGUGGCAGUCGA | 299 |
| hsa-mir-628-5p | MIMAT0004809 | AUGCUGACAUAUUUACUAGAGG | 300 |
| hsa-mir-643 | MIMAT0003313 | ACUUGUAUGCUAGCUCAGGUAG | 301 |
| hsa-mir-660 | MIMAT0003338 | UACCCAUUGCAUAUCGGAGUUG | 302 |

REFERENCES

1. Baj-Krzyworzeka M, Szatanek R, Weglarczyk K, Baran 7, Urbanowicz B, Branski P, Ratajczak M Z, Zembala M. Tumour-derived microvesicles carry several surface determinants and mRNA of tumour cells and transfer some of these determinants to monocytes. Cancer Immunol Immunother. 2006; 55:808818.
2. Rauch U, Bonderman D, Bohrmann B, Badimon J J, Himber J, Riederer M A, Nemerson Y. Transfer of tissue factor from leukocytes to platelets is mediated by CD15 and tissue factor. Blood. 2000; 96:170-175.
3. Jungi T W, Spycher M O, Nydegger U E, Barandun S. Platelet-leukocyte interaction: selective binding of thrombin-stimulated platelets to human monocytes, polymorphonuclear leukocytes, and related cell lines. Blood. 1986; 67:629-636.
4. Lyberg T, Nakstad B, Hetland O, Boye N P. Procoagulant (thromboplastin) activity in human bronchoalveolar lavage fluids is derived from alveolar macrophages. Eur Respir J. 1990; 3:61-67.
5. Thiagarajan P, Le A, Benedict CR. Beta(2)-glycoprotein I promotes the binding of anionic phospholipid vesicles by macrophages. Arterioscler Thromb Vase Biol. 1999; 19:2807-2811.
6. Setzer F, Oberle V, Blass M, Moller E, Russwurm S, Deigner H P, Claus R A, Bauer M, Reinhart K, Losche W. Platelet-derived microvesicles induce differential gene expression in monocytic cells: a DNA microarray study. Platelets. 2006;17:571-576.
7. Plasterk R H. Micro RNAs in animal development. Cell. 2006;124:877-881.
8. Willingham A T, Gingeras T R. TUF love for "junk" DNA. Cell. 2006;125:12151220.
9. Liu C G, Calin G A, Meloon B, Gamliel N, Sevignani C, Ferracin M, Dumitru C D, Shimizu M, Zupo S, Dono M, Alder H, Bullrich F, Negrini M, Croce C M. An oligonucleotide microchip for genome-wide microRNA profiling in human and mouse tissues. Proc Natl Acad Sci USA. 2004;101:9740-9744.
10. Calin G A, Croce C M. Genomics of chronic lymphocytic leukemia microRNAs as new players with clinical significance. Semin Oncol. 2006;33:167-173.
11. Hebert C, Norris K, Scheper M A, Nikitakis N, Sauk B. High mobility group A2 is a target for miRNA-98 in head and neck squamous cell carcinoma. Mol Cancer. 2007;6: 5.
12. Voorhoeve P M, Agami R. Classifying microRNAs in cancer: The good, the bad and the ugly. Biochim Biophys Acta. 2006.
13. Taganov K D, Boldin M P, Chang K J, Baltimore D. NF-kappaB-dependent induction of microRNA miR-146, an inhibitor targeted to signaling proteins of innate immune responses. Proc Natl Acad Sci USA. 2006;103: 12481-12486.

What is claimed is:

1. A method of diagnosing or prognosticating a colorectal cancer in a subject, comprising:
   i) isolating microvesicles from a sample from the subject;
   ii) determining a level of at least one miR gene product in the microvesicles, wherein the at least one miR gene product comprises miR-19a, miR-21, miR-127, miR-31, miR-96, miR-135b, miR-183, miR-30c, miR-133a, miR-143, miR-133b or miR-145; and
   iii) comparing the level of the at least one miR gene product in the sample to a control;
   iv) detecting an increased level of the at least one miR gene product in the sample compared to the control, wherein the at least one miR gene product comprises miR-19a, miR-21, miR-127, miR-31, miR-96, miR-135b or miR-183, and/or
   detecting a decreased level of the at least one miR gene product in the sample compared to the control, wherein the at least one miR gene product comprises miR-30c, miR-133a, miR-143, miR-133b, or miR-145;and
   v) diagnosing or prognosticating colorectal cancer from the detected increased level of the at least one miR gene product that comprises miR-19a, miR-21, miR-127, miR-31, miR-96, miR-135b or miR-183, or from the decreased level of the at least one miR gene product that comprises miR-30c, miR-133a, miR-143, miR-133b, or miR-145.

2. The method of claim 1, wherein the control is selected from the group consisting of:
   i) a reference standard;
   ii) the level of the at least one miR gene product from a subject that does not have colorectal cancer; and
   iii) the level of the at least one miR gene product from a sample of the subject that does not exhibit colorectal cancer.

3. The method of claim 1, wherein the subject is a human.

4. The method of claim 1, wherein determining the level of at least one miR gene product comprises:
   (a) labeling the miR isolated from the sample from the subject;
   (b) hybridizing the miR to an miR array; and
   (c) determining miR hybridization to the array.

5. The method of claim 1, wherein the comparing and detecting comprise generating an miR profile for the sample and evaluating the miR profile to determine whether miR in the sample are differentially expressed compared to a normal sample.

6. The method of claim 1, wherein the sample comprises a peripheral fluid.

7. The method of claim 6, wherein the peripheral fluid comprises blood or a fraction thereof.

8. The method of claim 1, wherein determining the level of at least one miR gene product comprises using real-time PCR.

9. The method of claim 1, wherein the microvesicles are isolated from the sample using ultracentrifugation and/or flow cytometry.

10. The method of claim 1, wherein the determining step comprises determining a level of miR-19a, miR-21, miR-127, miR-31, miR-96, miR-135b, miR-183, miR-30c, miR-133a, miR-143, miR-133b, and miR-145.

11. The method according to claim 1, further comprising administering at least one therapeutic agent to the subject to modulate the level of the at least one miR gene product in the subject.

12. The method according to claim 11, wherein the at least one miR gene product comprises miR-30c, miR-133a, miR-143, miR-133b, or miR-145,
   wherein a decreased level of the at least one miR gene product has been detected in the sample, and
   wherein the administering step comprises administering, as the therapeutic agent, an effective amount of said miR gene product to the subject.

13. The method according to claim 11, wherein the at least one miR gene product comprises miR-19a, miR-21, miR-127, miR-31, miR-96, miR-135b or miR-183,
   wherein an increased level of the at least one miR gene product has been detected in the sample, and
   wherein the administering step comprises administering to the subject, as the therapeutic agent, an effective amount of a compound that inhibits expression of said miR gene product in the subject, said compound comprising at least one member selected from the group consisting of double-stranded RNA, antisense nucleic acid, and enzymatic RNA.

14. A method of diagnosing or prognosticating a colorectal cancer in a subject, comprising:
   i) isolating microvesicles from a sample from the subject;
   ii) determining a level of at least one miR gene product in the microvesicles, wherein the at least one miR gene product comprises miR-127, miR-30c, miR-133a, or miR-143; and
   iii) comparing the level of the at least one miR gene product in the sample to a control;
   iv) detecting an increased level of the at least one miR gene product in the sample compared to the control, wherein the at least one miR gene product comprises miR-127and/or
   detecting a decreased level of the at least one miR gene product in the sample compared to the control, wherein the at least one miR gene product comprises miR-30c, miR-133a, or miR-143; and
   v) diagnosing or prognosticating colorectal cancer from the detected increased level of the at least one miR gene product that comprises miR-127, or from the decreased level of the at least one miR gene product that comprises miR-30c, miR-133a, or miR-143.

* * * * *

SEQUENCE LISTING

```
<160> NUMBER OF SEQ ID NOS: 302

<210> SEQ ID NO 1
<211> LENGTH: 21
<212> TYPE: RNA
<213> ORGANISM: Homo sapiens

<400> SEQUENCE: 1
cuauacaauc uacugucuuu c                                              21

<210> SEQ ID NO 2
<211> LENGTH: 22
```

```
<212> TYPE: RNA
<213> ORGANISM: Homo sapiens

<400> SEQUENCE: 2
ugagguagua gguuguauag uu                                              22

<210> SEQ ID NO 3
<211> LENGTH: 22
<212> TYPE: RNA
<213> ORGANISM: Homo sapiens

<400> SEQUENCE: 3
ugagguagua gguuguauag uu                                              22

<210> SEQ ID NO 4
<211> LENGTH: 22
<212> TYPE: RNA
<213> ORGANISM: Homo sapiens

<400> SEQUENCE: 4
ugagguagua gguuguauag uu                                              22

<210> SEQ ID NO 5
<211> LENGTH: 22
<212> TYPE: RNA
<213> ORGANISM: Homo sapiens

<400> SEQUENCE: 5
ugagguagua gguugugugg uu                                              22

<210> SEQ ID NO 6
<211> LENGTH: 22
<212> TYPE: RNA
<213> ORGANISM: Homo sapiens

<400> SEQUENCE: 6
cuauacaacc uacugccuuc cc                                              22

<210> SEQ ID NO 7
<211> LENGTH: 22
<212> TYPE: RNA
<213> ORGANISM: Homo sapiens

<400> SEQUENCE: 7
ugagguagua gguuguaugg uu                                              22

<210> SEQ ID NO 8
<211> LENGTH: 22
<212> TYPE: RNA
<213> ORGANISM: Homo sapiens

<400> SEQUENCE: 8
uagaguuaca cccugggagu ua                                              22

<210> SEQ ID NO 9
<211> LENGTH: 22
<212> TYPE: RNA
<213> ORGANISM: Homo sapiens

<400> SEQUENCE: 9
agagguagua gguugcauag uu                                              22

<210> SEQ ID NO 10
```

```
<211> LENGTH: 22
<212> TYPE: RNA
<213> ORGANISM: Homo sapiens

<400> SEQUENCE: 10
cuauacgacc ugcugccuuu cu                                              22

<210> SEQ ID NO 11
<211> LENGTH: 22
<212> TYPE: RNA
<213> ORGANISM: Homo sapiens

<400> SEQUENCE: 11
ugagguagga gguuguauag uu                                              22

<210> SEQ ID NO 12
<211> LENGTH: 22
<212> TYPE: RNA
<213> ORGANISM: Homo sapiens

<400> SEQUENCE: 12
cuauacggcc uccuagcuuu cc                                              22

<210> SEQ ID NO 13
<211> LENGTH: 22
<212> TYPE: RNA
<213> ORGANISM: Homo sapiens

<400> SEQUENCE: 13
ugagguagua gauuguauag uu                                              22

<210> SEQ ID NO 14
<211> LENGTH: 22
<212> TYPE: RNA
<213> ORGANISM: Homo sapiens

<400> SEQUENCE: 14
cuauacaauc uauugccuuc cc                                              22

<210> SEQ ID NO 15
<211> LENGTH: 22
<212> TYPE: RNA
<213> ORGANISM: Homo sapiens

<400> SEQUENCE: 15
ugagguagua gauuguauag uu                                              22

<210> SEQ ID NO 16
<211> LENGTH: 22
<212> TYPE: RNA
<213> ORGANISM: Homo sapiens

<400> SEQUENCE: 16
cuauacaguc uacugucuuu cc                                              22

<210> SEQ ID NO 17
<211> LENGTH: 22
<212> TYPE: RNA
<213> ORGANISM: Homo sapiens

<400> SEQUENCE: 17
ugagguagua guuuguacag uu                                              22
```

-continued

```
<210> SEQ ID NO 18
<211> LENGTH: 21
<212> TYPE: RNA
<213> ORGANISM: Homo sapiens

<400> SEQUENCE: 18 cguacaggc cacugccuug c                                              21

<210> SEQ ID NO 19
<211> LENGTH: 22
<212> TYPE: RNA
<213> ORGANISM: Homo sapiens

<400> SEQUENCE: 19
ugagguagua guuugugcug uu                                            22

<210> SEQ ID NO 20
<211> LENGTH: 22
<212> TYPE: RNA
<213> ORGANISM: Homo sapiens

<400> SEQUENCE: 20
cugcgcaagc uacugccuug cu                                            22

<210> SEQ ID NO 21
<211> LENGTH: 23
<212> TYPE: RNA
<213> ORGANISM: Homo sapiens

<400> SEQUENCE: 21
ucuuugguua ucuagcugua uga                                           23

<210> SEQ ID NO 22
<211> LENGTH: 22
<212> TYPE: RNA
<213> ORGANISM: Homo sapiens

<400> SEQUENCE: 22
auaaagcuag auaaccgaaa gu                                            22

<210> SEQ ID NO 23
<211> LENGTH: 23
<212> TYPE: RNA
<213> ORGANISM: Homo sapiens

<400> SEQUENCE: 23
ucuuugguua ucuagcugua uga                                           23

<210> SEQ ID NO 24
<211> LENGTH: 23
<212> TYPE: RNA
<213> ORGANISM: Homo sapiens

<400> SEQUENCE: 24
ucuuugguua ucuagcugua uga                                           23

<210> SEQ ID NO 25
<211> LENGTH: 23
<212> TYPE: RNA
<213> ORGANISM: Homo sapiens

<400> SEQUENCE: 25
uacccuguag auccgaauuu gug                                           23
```

```
<210> SEQ ID NO 26
<211> LENGTH: 22
<212> TYPE: RNA
<213> ORGANISM: Homo sapiens

<400> SEQUENCE: 26
caaauucgua ucuaggggaa ua                                              22

<210> SEQ ID NO 27
<211> LENGTH: 22
<212> TYPE: RNA
<213> ORGANISM: Homo sapiens

<400> SEQUENCE: 27
uagcagcaca uaaugguuug ug                                              22

<210> SEQ ID NO 28
<211> LENGTH: 22
<212> TYPE: RNA
<213> ORGANISM: Homo sapiens

<400> SEQUENCE: 28
uagcagcaca ucaugguuua ca                                              22

<210> SEQ ID NO 29
<211> LENGTH: 22
<212> TYPE: RNA
<213> ORGANISM: Homo sapiens

<400> SEQUENCE: 29
cgaaucauua uuugcugcuc ua                                              22

<210> SEQ ID NO 30
<211> LENGTH: 22
<212> TYPE: RNA
<213> ORGANISM: Homo sapiens

<400> SEQUENCE: 30
uagcagcacg uaaauauugg cg                                              22

<210> SEQ ID NO 31
<211> LENGTH: 22
<212> TYPE: RNA
<213> ORGANISM: Homo sapiens

<400> SEQUENCE: 31
ccaguauuaa cugugcugcu ga                                              22

<210> SEQ ID NO 32
<211> LENGTH: 22
<212> TYPE: RNA
<213> ORGANISM: Homo sapiens

<400> SEQUENCE: 32
uagcagcacg uaaauauugg cg                                              22

<210> SEQ ID NO 33
<211> LENGTH: 22
<212> TYPE: RNA
<213> ORGANISM: Homo sapiens

<400> SEQUENCE: 33
ccaauauuac ugugcugcuu ua                                              22
```

<210> SEQ ID NO 34
<211> LENGTH: 22
<212> TYPE: RNA
<213> ORGANISM: Homo sapiens

<400> SEQUENCE: 34
acugcaguga aggcacuugu ag                                    22

<210> SEQ ID NO 35
<211> LENGTH: 23
<212> TYPE: RNA
<213> ORGANISM: Homo sapiens

<400> SEQUENCE: 35
caaagugcuu acagugcagg uag                                   23

<210> SEQ ID NO 36
<211> LENGTH: 23
<212> TYPE: RNA
<213> ORGANISM: Homo sapiens

<400> SEQUENCE: 36
uaaggugcau cuagugcaga uag                                   23

<210> SEQ ID NO 37
<211> LENGTH: 23
<212> TYPE: RNA
<213> ORGANISM: Homo sapiens

<400> SEQUENCE: 37
acugcccuaa gugcuccuuc ugg                                   23

<210> SEQ ID NO 38
<211> LENGTH: 23
<212> TYPE: RNA
<213> ORGANISM: Homo sapiens

<400> SEQUENCE: 38
ugugcaaauc uaugcaaaac uga                                   23

<210> SEQ ID NO 39
<211> LENGTH: 23
<212> TYPE: RNA
<213> ORGANISM: Homo sapiens

<400> SEQUENCE: 39
ugugcaaauc caugcaaaac uga                                   23

<210> SEQ ID NO 40
<211> LENGTH: 23
<212> TYPE: RNA
<213> ORGANISM: Homo sapiens

<400> SEQUENCE: 40
aguuuugcag guuugcaucc agc                                   23

<210> SEQ ID NO 41
<211> LENGTH: 23
<212> TYPE: RNA
<213> ORGANISM: Homo sapiens

<400> SEQUENCE: 41
ugugcaaauc caugcaaaac uga                                            23

<210> SEQ ID NO 42
<211> LENGTH: 22
<212> TYPE: RNA
<213> ORGANISM: Homo sapiens

<400> SEQUENCE: 42
aguuuugcag guuugcauuu ca                                             22

<210> SEQ ID NO 43
<211> LENGTH: 23
<212> TYPE: RNA
<213> ORGANISM: Homo sapiens

<400> SEQUENCE: 43
uaaagugcuu auagugcagg uag                                            23

<210> SEQ ID NO 44
<211> LENGTH: 22
<212> TYPE: RNA
<213> ORGANISM: Homo sapiens

<400> SEQUENCE: 44
acugcauuau gagcacuuaa ag                                             22

<210> SEQ ID NO 45
<211> LENGTH: 23
<212> TYPE: RNA
<213> ORGANISM: Homo sapiens

<400> SEQUENCE: 45
caaagugcuc auagugcagg uag                                            23

<210> SEQ ID NO 46
<211> LENGTH: 22
<212> TYPE: RNA
<213> ORGANISM: Homo sapiens

<400> SEQUENCE: 46
uagcuuauca gacugauguu ga                                             22

<210> SEQ ID NO 47
<211> LENGTH: 21
<212> TYPE: RNA
<213> ORGANISM: Homo sapiens

<400> SEQUENCE: 47
caacaccagu cgaugggcug u                                              21

<210> SEQ ID NO 48
<211> LENGTH: 21
<212> TYPE: RNA
<213> ORGANISM: Homo sapiens

<400> SEQUENCE: 48
aucacauugc cagggauuuc c                                              21

<210> SEQ ID NO 49
<211> LENGTH: 22
<212> TYPE: RNA
<213> ORGANISM: Homo sapiens

<400> SEQUENCE: 49
gggguuccug gggaugggau uu                                              22

<210> SEQ ID NO 50
<211> LENGTH: 22
<212> TYPE: RNA
<213> ORGANISM: Homo sapiens

<400> SEQUENCE: 50
uggguuccug gcaugcugau uu                                              22

<210> SEQ ID NO 51
<211> LENGTH: 22
<212> TYPE: RNA
<213> ORGANISM: Homo sapiens

<400> SEQUENCE: 51
uggcucaguu cagcaggaac ag                                              22

<210> SEQ ID NO 52
<211> LENGTH: 22
<212> TYPE: RNA
<213> ORGANISM: Homo sapiens

<400> SEQUENCE: 52
ugccuacuga gcugauauca gu                                              22

<210> SEQ ID NO 53
<211> LENGTH: 22
<212> TYPE: RNA
<213> ORGANISM: Homo sapiens

<400> SEQUENCE: 53
uggcucaguu cagcaggaac ag                                              22

<210> SEQ ID NO 54
<211> LENGTH: 22
<212> TYPE: RNA
<213> ORGANISM: Homo sapiens

<400> SEQUENCE: 54
ugccuacuga gcugaaacac ag                                              22

<210> SEQ ID NO 55
<211> LENGTH: 22
<212> TYPE: RNA
<213> ORGANISM: Homo sapiens

<400> SEQUENCE: 55
cauugcacuu gucucggucu ga                                              22

<210> SEQ ID NO 56
<211> LENGTH: 21
<212> TYPE: RNA
<213> ORGANISM: Homo sapiens

<400> SEQUENCE: 56
aggcggagac uugggcaauu g                                               21

<210> SEQ ID NO 57
<211> LENGTH: 22
<212> TYPE: RNA
<213> ORGANISM: Homo sapiens -continued

```
<400> SEQUENCE: 57
uucaaguaau ccaggauagg cu                                              22

<210> SEQ ID NO 58
<211> LENGTH: 22
<212> TYPE: RNA
<213> ORGANISM: Homo sapiens

<400> SEQUENCE: 58
ccuauucuug guuacuugca cg                                              22

<210> SEQ ID NO 59
<211> LENGTH: 22
<212> TYPE: RNA
<213> ORGANISM: Homo sapiens

<400> SEQUENCE: 59
uucaaguaau ccaggauagg cu                                              22

<210> SEQ ID NO 60
<211> LENGTH: 22
<212> TYPE: RNA
<213> ORGANISM: Homo sapiens

<400> SEQUENCE: 60
ccuauucuug auuacuuguu uc                                              22

<210> SEQ ID NO 61
<211> LENGTH: 21
<212> TYPE: RNA
<213> ORGANISM: Homo sapiens

<400> SEQUENCE: 61
uucaaguaau ucaggauagg u                                               21

<210> SEQ ID NO 62
<211> LENGTH: 22
<212> TYPE: RNA
<213> ORGANISM: Homo sapiens

<400> SEQUENCE: 62
ccuguucucc auuacuuggc uc                                              22

<210> SEQ ID NO 63
<211> LENGTH: 21
<212> TYPE: RNA
<213> ORGANISM: Homo sapiens

<400> SEQUENCE: 63
uucacagugg cuaaguuccg c                                               21

<210> SEQ ID NO 64
<211> LENGTH: 22
<212> TYPE: RNA
<213> ORGANISM: Homo sapiens

<400> SEQUENCE: 64
agggcuuagc ugcuugugag ca                                              22

<210> SEQ ID NO 65
<211> LENGTH: 21
<212> TYPE: RNA
<213> ORGANISM: Homo sapiens
```

-continued

```
<400> SEQUENCE: 65
uucacagugg cuaaguucug c                                          21

<210> SEQ ID NO 66
<211> LENGTH: 22
<212> TYPE: RNA
<213> ORGANISM: Homo sapiens

<400> SEQUENCE: 66
agagcuuagc ugauugguga ac                                         22

<210> SEQ ID NO 67
<211> LENGTH: 22
<212> TYPE: RNA
<213> ORGANISM: Homo sapiens

<400> SEQUENCE: 67
cacuagauug ugagcuccug ga                                         22

<210> SEQ ID NO 68
<211> LENGTH: 22
<212> TYPE: RNA
<213> ORGANISM: Homo sapiens

<400> SEQUENCE: 68
aaggagcuca cagucuauug ag                                         22

<210> SEQ ID NO 69
<211> LENGTH: 22
<212> TYPE: RNA
<213> ORGANISM: Homo sapiens

<400> SEQUENCE: 69
uagcaccauc ugaaaucggu ua                                         22

<210> SEQ ID NO 70
<211> LENGTH: 22
<212> TYPE: RNA
<213> ORGANISM: Homo sapiens

<400> SEQUENCE: 70
acugauuucu uuggguguuc ag                                         22

<210> SEQ ID NO 71
<211> LENGTH: 23
<212> TYPE: RNA
<213> ORGANISM: Homo sapiens

<400> SEQUENCE: 71
uagcaccauu ugaaaucagu guu                                        23

<210> SEQ ID NO 72
<211> LENGTH: 24
<212> TYPE: RNA
<213> ORGANISM: Homo sapiens

<400> SEQUENCE: 72
gcugguuuca uauggugguu uaga                                       24

<210> SEQ ID NO 73
<211> LENGTH: 23
<212> TYPE: RNA
```

<213> ORGANISM: Homo sapiens

<400> SEQUENCE: 73
uagcaccauu ugaaaucagu guu                                    23

<210> SEQ ID NO 74
<211> LENGTH: 22
<212> TYPE: RNA
<213> ORGANISM: Homo sapiens

<400> SEQUENCE: 74
cugguuucac augguggcuu ag                                     22

<210> SEQ ID NO 75
<211> LENGTH: 23
<212> TYPE: RNA
<213> ORGANISM: Homo sapiens

<400> SEQUENCE: 75
uagcaccauu ugaaaucagu guu                                    23

<210> SEQ ID NO 76
<211> LENGTH: 22
<212> TYPE: RNA
<213> ORGANISM: Homo sapiens

<400> SEQUENCE: 76
uagcaccauu ugaaaucggu ua                                     22

<210> SEQ ID NO 77
<211> LENGTH: 22
<212> TYPE: RNA
<213> ORGANISM: Homo sapiens

<400> SEQUENCE: 77
uguaaacauc cucgacugga ag                                     22

<210> SEQ ID NO 78
<211> LENGTH: 22
<212> TYPE: RNA
<213> ORGANISM: Homo sapiens

<400> SEQUENCE: 78
cuuucagucg gauguuugca gc                                     22

<210> SEQ ID NO 79
<211> LENGTH: 22
<212> TYPE: RNA
<213> ORGANISM: Homo sapiens

<400> SEQUENCE: 79
uguaaacauc cuacacucag cu                                     22

<210> SEQ ID NO 80
<211> LENGTH: 22
<212> TYPE: RNA
<213> ORGANISM: Homo sapiens

<400> SEQUENCE: 80
cugggaggug gauguuuacu uc                                     22

<210> SEQ ID NO 81
<211> LENGTH: 23

```
<212> TYPE: RNA
<213> ORGANISM: Homo sapiens

<400> SEQUENCE: 81
uguaaacauc cuacacucuc agc                                              23

<210> SEQ ID NO 82
<211> LENGTH: 23
<212> TYPE: RNA
<213> ORGANISM: Homo sapiens

<400> SEQUENCE: 82
uguaaacauc cuacacucuc agc                                              23

<210> SEQ ID NO 83
<211> LENGTH: 22
<212> TYPE: RNA
<213> ORGANISM: Homo sapiens

<400> SEQUENCE: 83
cugggagaag gcuguuuacu cu                                               22

<210> SEQ ID NO 84
<211> LENGTH: 22
<212> TYPE: RNA
<213> ORGANISM: Homo sapiens

<400> SEQUENCE: 84
uguaaacauc cccgacugga ag                                               22

<210> SEQ ID NO 85
<211> LENGTH: 22
<212> TYPE: RNA
<213> ORGANISM: Homo sapiens

<400> SEQUENCE: 85
cuuucaguca gauguuugcu gc                                               22

<210> SEQ ID NO 86
<211> LENGTH: 21
<212> TYPE: RNA
<213> ORGANISM: Homo sapiens

<400> SEQUENCE: 86
aggcaagaug cuggcauagc u                                                21

<210> SEQ ID NO 87
<211> LENGTH: 22
<212> TYPE: RNA
<213> ORGANISM: Homo sapiens

<400> SEQUENCE: 87
ugcuaugcca acauauugcc au                                               22

<210> SEQ ID NO 88
<211> LENGTH: 22
<212> TYPE: RNA
<213> ORGANISM: Homo sapiens

<400> SEQUENCE: 88
uauugcacau uacuaaguug ca                                               22

<210> SEQ ID NO 89
```

```
<211> LENGTH: 22
<212> TYPE: RNA
<213> ORGANISM: Homo sapiens

<400> SEQUENCE: 89
caauuuagug ugugugauau uu                                              22

<210> SEQ ID NO 90
<211> LENGTH: 22
<212> TYPE: RNA
<213> ORGANISM: Homo sapiens

<400> SEQUENCE: 90
uggcaguguc uuagcugguu gu                                              22

<210> SEQ ID NO 91
<211> LENGTH: 22
<212> TYPE: RNA
<213> ORGANISM: Homo sapiens

<400> SEQUENCE: 91
caaucagcaa guauacugcc cu                                              22

<210> SEQ ID NO 92
<211> LENGTH: 22
<212> TYPE: RNA
<213> ORGANISM: Homo sapiens

<400> SEQUENCE: 92
uauugcacuu gucccggccu gu                                              22

<210> SEQ ID NO 93
<211> LENGTH: 23
<212> TYPE: RNA
<213> ORGANISM: Homo sapiens

<400> SEQUENCE: 93
agguugggau cgguugcaau gcu                                             23

<210> SEQ ID NO 94
<211> LENGTH: 23
<212> TYPE: RNA
<213> ORGANISM: Homo sapiens

<400> SEQUENCE: 94
caaagugcug uucgugcagg uag                                             23

<210> SEQ ID NO 95
<211> LENGTH: 22
<212> TYPE: RNA
<213> ORGANISM: Homo sapiens

<400> SEQUENCE: 95
acugcugagc uagcacuucc cg                                              22

<210> SEQ ID NO 96
<211> LENGTH: 22
<212> TYPE: RNA
<213> ORGANISM: Homo sapiens

<400> SEQUENCE: 96
uucaacgggu auuuauugag ca                                              22
```

```
<210> SEQ ID NO 97
<211> LENGTH: 23
<212> TYPE: RNA
<213> ORGANISM: Homo sapiens

<400> SEQUENCE: 97
uuuggcacua gcacauuuuu gcu                                              23

<210> SEQ ID NO 98
<211> LENGTH: 22
<212> TYPE: RNA
<213> ORGANISM: Homo sapiens

<400> SEQUENCE: 98
aaucaugugc agugccaaua ug                                               22

<210> SEQ ID NO 99
<211> LENGTH: 22
<212> TYPE: RNA
<213> ORGANISM: Homo sapiens

<400> SEQUENCE: 99
ugagguagua aguuguauug uu                                               22

<210> SEQ ID NO 100
<211> LENGTH: 22
<212> TYPE: RNA
<213> ORGANISM: Homo sapiens

<400> SEQUENCE: 100
cacccguaga accgaccuug cg                                               22

<210> SEQ ID NO 101
<211> LENGTH: 22
<212> TYPE: RNA
<213> ORGANISM: Homo sapiens

<400> SEQUENCE: 101
caagcucgug ucuguggguc cg                                               22

<210> SEQ ID NO 102
<211> LENGTH: 22
<212> TYPE: RNA
<213> ORGANISM: Homo sapiens

<400> SEQUENCE: 102
aacccguaga uccgaacuug ug                                               22

<210> SEQ ID NO 103
<211> LENGTH: 22
<212> TYPE: RNA
<213> ORGANISM: Homo sapiens

<400> SEQUENCE: 103
caagcuugua ucuauaggua ug                                               22

<210> SEQ ID NO 104
<211> LENGTH: 23
<212> TYPE: RNA
<213> ORGANISM: Homo sapiens

<400> SEQUENCE: 104
agcagcauug uacagggcua uga                                              23
```

```
<210> SEQ ID NO 105
<211> LENGTH: 23
<212> TYPE: RNA
<213> ORGANISM: Homo sapiens

<400> SEQUENCE: 105
agcagcauug uacagggcua uga                                              23

<210> SEQ ID NO 106
<211> LENGTH: 23
<212> TYPE: RNA
<213> ORGANISM: Homo sapiens

<400> SEQUENCE: 106
ucaaaugcuc agacuccugu ggu                                              23

<210> SEQ ID NO 107
<211> LENGTH: 22
<212> TYPE: RNA
<213> ORGANISM: Homo sapiens

<400> SEQUENCE: 107
acggauguuu gagcaugugc ua                                               22

<210> SEQ ID NO 108
<211> LENGTH: 23
<212> TYPE: RNA
<213> ORGANISM: Homo sapiens

<400> SEQUENCE: 108
ucaaaugcuc agacuccugu ggu                                              23

<210> SEQ ID NO 109
<211> LENGTH: 22
<212> TYPE: RNA
<213> ORGANISM: Homo sapiens

<400> SEQUENCE: 109
acggauguuu gagcaugugc ua                                               22

<210> SEQ ID NO 110
<211> LENGTH: 23
<212> TYPE: RNA
<213> ORGANISM: Homo sapiens

<400> SEQUENCE: 110
aaaagugcuu acagugcagg uag                                              23

<210> SEQ ID NO 111
<211> LENGTH: 22
<212> TYPE: RNA
<213> ORGANISM: Homo sapiens

<400> SEQUENCE: 111
cugcaaugua agcacuucuu ac                                               22

<210> SEQ ID NO 112
<211> LENGTH: 21
<212> TYPE: RNA
<213> ORGANISM: Homo sapiens

<400> SEQUENCE: 112
uaaagugcug acagugcaga u                                                21
```

<210> SEQ ID NO 113
<211> LENGTH: 22
<212> TYPE: RNA
<213> ORGANISM: Homo sapiens

<400> SEQUENCE: 113
ccgcacugug gguacuugcu gc                                              22

<210> SEQ ID NO 114
<211> LENGTH: 23
<212> TYPE: RNA
<213> ORGANISM: Homo sapiens

<400> SEQUENCE: 114
agcagcauug uacagggcua uca                                             23

<210> SEQ ID NO 115
<211> LENGTH: 22
<212> TYPE: RNA
<213> ORGANISM: Homo sapiens

<400> SEQUENCE: 115
uggaguguga caauggeguu ug                                              22

<210> SEQ ID NO 116
<211> LENGTH: 22
<212> TYPE: RNA
<213> ORGANISM: Homo sapiens

<400> SEQUENCE: 116
aacgccauua ucacacuaaa ua                                              22

<210> SEQ ID NO 117
<211> LENGTH: 22
<212> TYPE: RNA
<213> ORGANISM: Homo sapiens

<400> SEQUENCE: 117
acaggugagg uucuugggag cc                                              22

<210> SEQ ID NO 118
<211> LENGTH: 24
<212> TYPE: RNA
<213> ORGANISM: Homo sapiens

<400> SEQUENCE: 118
ucccugagac ccuuuaaccu guga                                            24

<210> SEQ ID NO 119
<211> LENGTH: 22
<212> TYPE: RNA
<213> ORGANISM: Homo sapiens

<400> SEQUENCE: 119
ucccugagac ccuaacuugu ga                                              22

<210> SEQ ID NO 120
<211> LENGTH: 22
<212> TYPE: RNA
<213> ORGANISM: Homo sapiens

<400> SEQUENCE: 120

```
acggguuagg cucuugggag cu                                              22

<210> SEQ ID NO 121
<211> LENGTH: 22
<212> TYPE: RNA
<213> ORGANISM: Homo sapiens

<400> SEQUENCE: 121
ucccugagac ccuaacuugu ga                                              22

<210> SEQ ID NO 122
<211> LENGTH: 22
<212> TYPE: RNA
<213> ORGANISM: Homo sapiens

<400> SEQUENCE: 122
ucacaaguca ggcucuuggg ac                                              22

<210> SEQ ID NO 123
<211> LENGTH: 22
<212> TYPE: RNA
<213> ORGANISM: Homo sapiens

<400> SEQUENCE: 123
ucguaccgug aguaauaaug cg                                              22

<210> SEQ ID NO 124
<211> LENGTH: 21
<212> TYPE: RNA
<213> ORGANISM: Homo sapiens

<400> SEQUENCE: 124
cauuauuacu uuggguacgc g                                               21

<210> SEQ ID NO 125
<211> LENGTH: 22
<212> TYPE: RNA
<213> ORGANISM: Homo sapiens

<400> SEQUENCE: 125
ucggauccgu cugagcuugg cu                                              22

<210> SEQ ID NO 126
<211> LENGTH: 22
<212> TYPE: RNA
<213> ORGANISM: Homo sapiens

<400> SEQUENCE: 126
cugaagcuca gagggcucug au                                              22

<210> SEQ ID NO 127
<211> LENGTH: 21
<212> TYPE: RNA
<213> ORGANISM: Homo sapiens

<400> SEQUENCE: 127
ucacagugaa ccggucucuu u                                               21

<210> SEQ ID NO 128
<211> LENGTH: 21
<212> TYPE: RNA
<213> ORGANISM: Homo sapiens

<400> SEQUENCE: 128
```

```
ucacagugaa ccgucucuu u                                    21

<210> SEQ ID NO 129
<211> LENGTH: 22
<212> TYPE: RNA
<213> ORGANISM: Homo sapiens

<400> SEQUENCE: 129
cagugcaaug uuaaaagggc au                                  22

<210> SEQ ID NO 130
<211> LENGTH: 22
<212> TYPE: RNA
<213> ORGANISM: Homo sapiens

<400> SEQUENCE: 130
uucacauugu gcuacugucu gc                                  22

<210> SEQ ID NO 131
<211> LENGTH: 22
<212> TYPE: RNA
<213> ORGANISM: Homo sapiens

<400> SEQUENCE: 131
cagugcaaug augaaagggc au                                  22

<210> SEQ ID NO 132
<211> LENGTH: 21
<212> TYPE: RNA
<213> ORGANISM: Homo sapiens

<400> SEQUENCE: 132
acucuuuccc uguugcacua c                                   21

<210> SEQ ID NO 133
<211> LENGTH: 22
<212> TYPE: RNA
<213> ORGANISM: Homo sapiens

<400> SEQUENCE: 133
uaacagucua cagccauggu cg                                  22

<210> SEQ ID NO 134
<211> LENGTH: 22
<212> TYPE: RNA
<213> ORGANISM: Homo sapiens

<400> SEQUENCE: 134
accguggcuu ucgauuguua cu                                  22

<210> SEQ ID NO 135
<211> LENGTH: 22
<212> TYPE: RNA
<213> ORGANISM: Homo sapiens

<400> SEQUENCE: 135
uuuggucccc uucaaccagc ug                                  22

<210> SEQ ID NO 136
<211> LENGTH: 22
<212> TYPE: RNA
<213> ORGANISM: Homo sapiens
```

```
<400> SEQUENCE: 136
uuuggucccc uucaaccagc ug                                            22

<210> SEQ ID NO 137
<211> LENGTH: 22
<212> TYPE: RNA
<213> ORGANISM: Homo sapiens

<400> SEQUENCE: 137
uuuggucccc uucaaccagc ua                                            22

<210> SEQ ID NO 138
<211> LENGTH: 22
<212> TYPE: RNA
<213> ORGANISM: Homo sapiens

<400> SEQUENCE: 138
ugugacuggu ugaccagagg gg                                            22

<210> SEQ ID NO 139
<211> LENGTH: 23
<212> TYPE: RNA
<213> ORGANISM: Homo sapiens

<400> SEQUENCE: 139
uauggcuuuu cauuccuaug uga                                           23

<210> SEQ ID NO 140
<211> LENGTH: 22
<212> TYPE: RNA
<213> ORGANISM: Homo sapiens

<400> SEQUENCE: 140
auguagggcu aaaagccaug gg                                            22

<210> SEQ ID NO 141
<211> LENGTH: 21
<212> TYPE: RNA
<213> ORGANISM: Homo sapiens

<400> SEQUENCE: 141
uaccacaggg uagaaccacg g                                             21

<210> SEQ ID NO 142
<211> LENGTH: 22
<212> TYPE: RNA
<213> ORGANISM: Homo sapiens

<400> SEQUENCE: 142
cagugguuuu acccuauggu ag                                            22

<210> SEQ ID NO 143
<211> LENGTH: 23
<212> TYPE: RNA
<213> ORGANISM: Homo sapiens

<400> SEQUENCE: 143
uguaguguuu ccuacuuuau gga                                           23

<210> SEQ ID NO 144
<211> LENGTH: 21
<212> TYPE: RNA
<213> ORGANISM: Homo sapiens
```

```
<400> SEQUENCE: 144
cauaaaguag aaagcacuac u                                              21

<210> SEQ ID NO 145
<211> LENGTH: 21
<212> TYPE: RNA
<213> ORGANISM: Homo sapiens

<400> SEQUENCE: 145
ugagaugaag cacuguagcu c                                              21

<210> SEQ ID NO 146
<211> LENGTH: 22
<212> TYPE: RNA
<213> ORGANISM: Homo sapiens

<400> SEQUENCE: 146
ggugcagugc ugcaucucug gu                                             22

<210> SEQ ID NO 147
<211> LENGTH: 23
<212> TYPE: RNA
<213> ORGANISM: Homo sapiens

<400> SEQUENCE: 147
guccaguuuu cccaggaauc ccu                                            23

<210> SEQ ID NO 148
<211> LENGTH: 22
<212> TYPE: RNA
<213> ORGANISM: Homo sapiens

<400> SEQUENCE: 148
ggauuccugg aaauacuguu cu                                             22

<210> SEQ ID NO 149
<211> LENGTH: 22
<212> TYPE: RNA
<213> ORGANISM: Homo sapiens

<400> SEQUENCE: 149
ugagaacuga auuccauggg uu                                             22

<210> SEQ ID NO 150
<211> LENGTH: 22
<212> TYPE: RNA
<213> ORGANISM: Homo sapiens

<400> SEQUENCE: 150
ccucugaaau ucaguucuuc ag                                             22

<210> SEQ ID NO 151
<211> LENGTH: 22
<212> TYPE: RNA
<213> ORGANISM: Homo sapiens

<400> SEQUENCE: 151
ugcccugugg acucaguucu gg                                             22

<210> SEQ ID NO 152
<211> LENGTH: 22
<212> TYPE: RNA
```

-continued

<213> ORGANISM: Homo sapiens

<400> SEQUENCE: 152
ugagaacuga auuccauagg cu                                          22

<210> SEQ ID NO 153
<211> LENGTH: 20
<212> TYPE: RNA
<213> ORGANISM: Homo sapiens

<400> SEQUENCE: 153
guguguggaa augcuucugc                                             20

<210> SEQ ID NO 154
<211> LENGTH: 22
<212> TYPE: RNA
<213> ORGANISM: Homo sapiens

<400> SEQUENCE: 154
ucagugcacu acagaacuuu gu                                          22

<210> SEQ ID NO 155
<211> LENGTH: 22
<212> TYPE: RNA
<213> ORGANISM: Homo sapiens

<400> SEQUENCE: 155
aaaguucuga gacacuccga cu                                          22

<210> SEQ ID NO 156
<211> LENGTH: 22
<212> TYPE: RNA
<213> ORGANISM: Homo sapiens

<400> SEQUENCE: 156
ucagugcauc acagaacuuu gu                                          22

<210> SEQ ID NO 157
<211> LENGTH: 22
<212> TYPE: RNA
<213> ORGANISM: Homo sapiens

<400> SEQUENCE: 157
aaguucuguu auacacucag gc                                          22

<210> SEQ ID NO 158
<211> LENGTH: 23
<212> TYPE: RNA
<213> ORGANISM: Homo sapiens

<400> SEQUENCE: 158
ucuggcuccg ugucuucacu ccc                                         23

<210> SEQ ID NO 159
<211> LENGTH: 21
<212> TYPE: RNA
<213> ORGANISM: Homo sapiens

<400> SEQUENCE: 159
agggagggac gggggcugug c                                           21

<210> SEQ ID NO 160
<211> LENGTH: 22

```
<212> TYPE: RNA
<213> ORGANISM: Homo sapiens

<400> SEQUENCE: 160
ucucccaacc cuuguaccag ug                                    22

<210> SEQ ID NO 161
<211> LENGTH: 22
<212> TYPE: RNA
<213> ORGANISM: Homo sapiens

<400> SEQUENCE: 161
cugguacagg ccuggggac ag                                     22

<210> SEQ ID NO 162
<211> LENGTH: 21
<212> TYPE: RNA
<213> ORGANISM: Homo sapiens

<400> SEQUENCE: 162
cuagacugaa gcuccuugag g                                     21

<210> SEQ ID NO 163
<211> LENGTH: 21
<212> TYPE: RNA
<213> ORGANISM: Homo sapiens

<400> SEQUENCE: 163
ucgaggagcu cacagucuag u                                     21

<210> SEQ ID NO 164
<211> LENGTH: 23
<212> TYPE: RNA
<213> ORGANISM: Homo sapiens

<400> SEQUENCE: 164
uuaaugcuaa ucgugauagg ggu                                   23

<210> SEQ ID NO 165
<211> LENGTH: 22
<212> TYPE: RNA
<213> ORGANISM: Homo sapiens

<400> SEQUENCE: 165
cuccuacaua uuagcauuaa ca                                    22

<210> SEQ ID NO 166
<211> LENGTH: 23
<212> TYPE: RNA
<213> ORGANISM: Homo sapiens

<400> SEQUENCE: 166
aacauucaac gcugucggug agu                                   23

<210> SEQ ID NO 167
<211> LENGTH: 22
<212> TYPE: RNA
<213> ORGANISM: Homo sapiens

<400> SEQUENCE: 167
accaucgacc guugauugua cc                                    22

<210> SEQ ID NO 168
```

```
<211> LENGTH: 23
<212> TYPE: RNA
<213> ORGANISM: Homo sapiens

<400> SEQUENCE: 168
aacauucaac gcugucggug agu                                              23

<210> SEQ ID NO 169
<211> LENGTH: 22
<212> TYPE: RNA
<213> ORGANISM: Homo sapiens

<400> SEQUENCE: 169
accacugacc guugacugua cc                                               22

<210> SEQ ID NO 170
<211> LENGTH: 23
<212> TYPE: RNA
<213> ORGANISM: Homo sapiens

<400> SEQUENCE: 170
aacauucauu gcugucggug ggu                                              23

<210> SEQ ID NO 171
<211> LENGTH: 23
<212> TYPE: RNA
<213> ORGANISM: Homo sapiens

<400> SEQUENCE: 171
aacauucauu gcugucggug ggu                                              23

<210> SEQ ID NO 172
<211> LENGTH: 23
<212> TYPE: RNA
<213> ORGANISM: Homo sapiens

<400> SEQUENCE: 172
aacauucauu guugucggug ggu                                              23

<210> SEQ ID NO 173
<211> LENGTH: 24
<212> TYPE: RNA
<213> ORGANISM: Homo sapiens

<400> SEQUENCE: 173
uuuggcaaug guagaacuca cacu                                             24

<210> SEQ ID NO 174
<211> LENGTH: 21
<212> TYPE: RNA
<213> ORGANISM: Homo sapiens

<400> SEQUENCE: 174
ugguucuaga cuugccaacu a                                                21

<210> SEQ ID NO 175
<211> LENGTH: 22
<212> TYPE: RNA
<213> ORGANISM: Homo sapiens

<400> SEQUENCE: 175
uauggcacug guagaauuca cu                                               22
```

```
<210> SEQ ID NO 176
<211> LENGTH: 22
<212> TYPE: RNA
<213> ORGANISM: Homo sapiens

<400> SEQUENCE: 176
gugaauuacc gaagggccau aa                                              22

<210> SEQ ID NO 177
<211> LENGTH: 22
<212> TYPE: RNA
<213> ORGANISM: Homo sapiens

<400> SEQUENCE: 177
uggagagaaa ggcaguuccu ga                                              22

<210> SEQ ID NO 178
<211> LENGTH: 22
<212> TYPE: RNA
<213> ORGANISM: Homo sapiens

<400> SEQUENCE: 178
aggggcuggc uuuccucugg uc                                              22

<210> SEQ ID NO 179
<211> LENGTH: 22
<212> TYPE: RNA
<213> ORGANISM: Homo sapiens

<400> SEQUENCE: 179
caaagaauuc uccuuuuggg cu                                              22

<210> SEQ ID NO 180
<211> LENGTH: 22
<212> TYPE: RNA
<213> ORGANISM: Homo sapiens

<400> SEQUENCE: 180
gcccaaaggu gaauuuuuug gg                                              22

<210> SEQ ID NO 181
<211> LENGTH: 22
<212> TYPE: RNA
<213> ORGANISM: Homo sapiens

<400> SEQUENCE: 181
ugauauguuu gauauauuag gu                                              22

<210> SEQ ID NO 182
<211> LENGTH: 23
<212> TYPE: RNA
<213> ORGANISM: Homo sapiens

<400> SEQUENCE: 182
caacggaauc ccaaaagcag cug                                             23

<210> SEQ ID NO 183
<211> LENGTH: 22
<212> TYPE: RNA
<213> ORGANISM: Homo sapiens

<400> SEQUENCE: 183
gcugcgcuug gauuucgucc cc                                              22
```

<210> SEQ ID NO 184
<211> LENGTH: 21
<212> TYPE: RNA
<213> ORGANISM: Homo sapiens

<400> SEQUENCE: 184
cugaccuaug aauugacagc c                                              21

<210> SEQ ID NO 185
<211> LENGTH: 22
<212> TYPE: RNA
<213> ORGANISM: Homo sapiens

<400> SEQUENCE: 185
cugccaauuc cauaggucac ag                                             22

<210> SEQ ID NO 186
<211> LENGTH: 22
<212> TYPE: RNA
<213> ORGANISM: Homo sapiens

<400> SEQUENCE: 186
aacuggccua caaagcccca gu                                             22

<210> SEQ ID NO 187
<211> LENGTH: 22
<212> TYPE: RNA
<213> ORGANISM: Homo sapiens

<400> SEQUENCE: 187
ugggucuuug cgggcgagau ga                                             22

<210> SEQ ID NO 188
<211> LENGTH: 22
<212> TYPE: RNA
<213> ORGANISM: Homo sapiens

<400> SEQUENCE: 188
aacuggcccu caaagucccg cu                                             22

<210> SEQ ID NO 189
<211> LENGTH: 22
<212> TYPE: RNA
<213> ORGANISM: Homo sapiens

<400> SEQUENCE: 189
cgggguuuug agggcgagau ga                                             22

<210> SEQ ID NO 190
<211> LENGTH: 21
<212> TYPE: RNA
<213> ORGANISM: Homo sapiens

<400> SEQUENCE: 190
uagcagcaca gaaauauugg c                                              21

<210> SEQ ID NO 191
<211> LENGTH: 22
<212> TYPE: RNA
<213> ORGANISM: Homo sapiens

<400> SEQUENCE: 191
ccaauauugg cugugcugcu cc                                             22

```
<210> SEQ ID NO 192
<211> LENGTH: 22
<212> TYPE: RNA
<213> ORGANISM: Homo sapiens

<400> SEQUENCE: 192
cggcaacaag aaacugccug ag                                              22

<210> SEQ ID NO 193
<211> LENGTH: 22
<212> TYPE: RNA
<213> ORGANISM: Homo sapiens

<400> SEQUENCE: 193
uagguaguuu cauguuguug gg                                              22

<210> SEQ ID NO 194
<211> LENGTH: 22
<212> TYPE: RNA
<213> ORGANISM: Homo sapiens

<400> SEQUENCE: 194
uagguaguuu cauguuguug gg                                              22

<210> SEQ ID NO 195
<211> LENGTH: 22
<212> TYPE: RNA
<213> ORGANISM: Homo sapiens

<400> SEQUENCE: 195
uagguaguuu ccuguuguug gg                                              22

<210> SEQ ID NO 196
<211> LENGTH: 22
<212> TYPE: RNA
<213> ORGANISM: Homo sapiens

<400> SEQUENCE: 196
uucaccaccu ucuccaccca gc                                              22

<210> SEQ ID NO 197
<211> LENGTH: 22
<212> TYPE: RNA
<213> ORGANISM: Homo sapiens

<400> SEQUENCE: 197
gguccagagg ggagauaggu uc                                              22

<210> SEQ ID NO 198
<211> LENGTH: 22
<212> TYPE: RNA
<213> ORGANISM: Homo sapiens

<400> SEQUENCE: 198
acaguagucu gcacauuggu ua                                              22

<210> SEQ ID NO 199
<211> LENGTH: 23
<212> TYPE: RNA
<213> ORGANISM: Homo sapiens

<400> SEQUENCE: 199
```
cccaguguuc agacuaccug uuc                                              23

<210> SEQ ID NO 200
<211> LENGTH: 23
<212> TYPE: RNA
<213> ORGANISM: Homo sapiens

<400> SEQUENCE: 200
cccaguguuc agacuaccug uuc                                              23

<210> SEQ ID NO 201
<211> LENGTH: 22
<212> TYPE: RNA
<213> ORGANISM: Homo sapiens

<400> SEQUENCE: 201
acaguagucu gcacauuggu ua                                               22

<210> SEQ ID NO 202
<211> LENGTH: 23
<212> TYPE: RNA
<213> ORGANISM: Homo sapiens

<400> SEQUENCE: 202
cccaguguuu agacuaucug uuc                                              23

<210> SEQ ID NO 203
<211> LENGTH: 22
<212> TYPE: RNA
<213> ORGANISM: Homo sapiens

<400> SEQUENCE: 203
uaacacuguc ugguaacgau gu                                               22

<210> SEQ ID NO 204
<211> LENGTH: 22
<212> TYPE: RNA
<213> ORGANISM: Homo sapiens

<400> SEQUENCE: 204
caucuuaccg gacagugcug ga                                               22

<210> SEQ ID NO 205
<211> LENGTH: 22
<212> TYPE: RNA
<213> ORGANISM: Homo sapiens

<400> SEQUENCE: 205
uaauacugcc ugguaaugau ga                                               22

<210> SEQ ID NO 206
<211> LENGTH: 22
<212> TYPE: RNA
<213> ORGANISM: Homo sapiens

<400> SEQUENCE: 206
caucuuacug ggcagcauug ga                                               22

<210> SEQ ID NO 207
<211> LENGTH: 23
<212> TYPE: RNA
<213> ORGANISM: Homo sapiens

<400> SEQUENCE: 207
uaauacugcc ggguaaugau gga 23

<210> SEQ ID NO 208
<211> LENGTH: 22
<212> TYPE: RNA
<213> ORGANISM: Homo sapiens

<400> SEQUENCE: 208
cgucuuaccc agcaguguuu gg 22

<210> SEQ ID NO 209
<211> LENGTH: 22
<212> TYPE: RNA
<213> ORGANISM: Homo sapiens

<400> SEQUENCE: 209
gugaaauguu uaggaccacu ag 22

<210> SEQ ID NO 210
<211> LENGTH: 22
<212> TYPE: RNA
<213> ORGANISM: Homo sapiens

<400> SEQUENCE: 210
uucccuuugu cauccuaugc cu 22

<210> SEQ ID NO 211
<211> LENGTH: 22
<212> TYPE: RNA
<213> ORGANISM: Homo sapiens

<400> SEQUENCE: 211
uccuucauuc caccggaguc ug 22

<210> SEQ ID NO 212
<211> LENGTH: 22
<212> TYPE: RNA
<213> ORGANISM: Homo sapiens

<400> SEQUENCE: 212
cugugcgugu gacagcggcu ga 22

<210> SEQ ID NO 213
<211> LENGTH: 23
<212> TYPE: RNA
<213> ORGANISM: Homo sapiens

<400> SEQUENCE: 213
aacauucaac gcugucggug agu 23

<210> SEQ ID NO 214
<211> LENGTH: 22
<212> TYPE: RNA
<213> ORGANISM: Homo sapiens

<400> SEQUENCE: 214
acagcaggca cagacaggca gu 22

<210> SEQ ID NO 215
<211> LENGTH: 22
<212> TYPE: RNA
<213> ORGANISM: Homo sapiens

```
<400> SEQUENCE: 215
ugccugucua cacuugcugu gc                                              22

<210> SEQ ID NO 216
<211> LENGTH: 22
<212> TYPE: RNA
<213> ORGANISM: Homo sapiens

<400> SEQUENCE: 216
uaaucucagc uggcaacugu ga                                              22

<210> SEQ ID NO 217
<211> LENGTH: 22
<212> TYPE: RNA
<213> ORGANISM: Homo sapiens

<400> SEQUENCE: 217
aaaucucugc aggcaaaugu ga                                              22

<210> SEQ ID NO 218
<211> LENGTH: 23
<212> TYPE: RNA
<213> ORGANISM: Homo sapiens

<400> SEQUENCE: 218
uacugcauca ggaacugauu gga                                             23

<210> SEQ ID NO 219
<211> LENGTH: 21
<212> TYPE: RNA
<213> ORGANISM: Homo sapiens

<400> SEQUENCE: 219
uugugcuuga ucuaaccaug u                                               21

<210> SEQ ID NO 220
<211> LENGTH: 22
<212> TYPE: RNA
<213> ORGANISM: Homo sapiens

<400> SEQUENCE: 220
augguuccgu caagcaccau gg                                              22

<210> SEQ ID NO 221
<211> LENGTH: 21
<212> TYPE: RNA
<213> ORGANISM: Homo sapiens

<400> SEQUENCE: 221
uugugcuuga ucuaaccaug u                                               21

<210> SEQ ID NO 222
<211> LENGTH: 22
<212> TYPE: RNA
<213> ORGANISM: Homo sapiens

<400> SEQUENCE: 222
caugguucug ucaagcaccg cg                                              22

<210> SEQ ID NO 223
<211> LENGTH: 23
<212> TYPE: RNA
<213> ORGANISM: Homo sapiens
```

```
<400> SEQUENCE: 223
agcuacauug ucugcugggu uuc                                          23

<210> SEQ ID NO 224
<211> LENGTH: 22
<212> TYPE: RNA
<213> ORGANISM: Homo sapiens

<400> SEQUENCE: 224
accuggcaua caauguagau uu                                           22

<210> SEQ ID NO 225
<211> LENGTH: 21
<212> TYPE: RNA
<213> ORGANISM: Homo sapiens

<400> SEQUENCE: 225
agcuacaucu ggcuacuggg u                                            21

<210> SEQ ID NO 226
<211> LENGTH: 22
<212> TYPE: RNA
<213> ORGANISM: Homo sapiens

<400> SEQUENCE: 226
cucaguagcc aguguagauc cu                                           22

<210> SEQ ID NO 227
<211> LENGTH: 22
<212> TYPE: RNA
<213> ORGANISM: Homo sapiens

<400> SEQUENCE: 227
ugucaguuug ucaaauaccc ca                                           22

<210> SEQ ID NO 228
<211> LENGTH: 22
<212> TYPE: RNA
<213> ORGANISM: Homo sapiens

<400> SEQUENCE: 228
cguguauuug acaagcugag uu                                           22

<210> SEQ ID NO 229
<211> LENGTH: 21
<212> TYPE: RNA
<213> ORGANISM: Homo sapiens

<400> SEQUENCE: 229
caagucacua gugguuccgu u                                            21

<210> SEQ ID NO 230
<211> LENGTH: 23
<212> TYPE: RNA
<213> ORGANISM: Homo sapiens

<400> SEQUENCE: 230
uaagugcuuc cauguuuugg uga                                          23

<210> SEQ ID NO 231
<211> LENGTH: 23
<212> TYPE: RNA
```

```
<213> ORGANISM: Homo sapiens

<400> SEQUENCE: 231
acuuaaacgu ggauguacuu gcu                                              23

<210> SEQ ID NO 232
<211> LENGTH: 23
<212> TYPE: RNA
<213> ORGANISM: Homo sapiens

<400> SEQUENCE: 232
uaagugcuuc cauguuuuag uag                                              23

<210> SEQ ID NO 233
<211> LENGTH: 22
<212> TYPE: RNA
<213> ORGANISM: Homo sapiens

<400> SEQUENCE: 233
acuuuaacau ggaagugcuu uc                                               22

<210> SEQ ID NO 234
<211> LENGTH: 23
<212> TYPE: RNA
<213> ORGANISM: Homo sapiens

<400> SEQUENCE: 234
uaagugcuuc cauguuucag ugg                                              23

<210> SEQ ID NO 235
<211> LENGTH: 22
<212> TYPE: RNA
<213> ORGANISM: Homo sapiens

<400> SEQUENCE: 235
uuuaacaugg ggguaccugc ug                                               22

<210> SEQ ID NO 236
<211> LENGTH: 23
<212> TYPE: RNA
<213> ORGANISM: Homo sapiens

<400> SEQUENCE: 236
uaagugcuuc cauguuugag ugu                                              23

<210> SEQ ID NO 237
<211> LENGTH: 22
<212> TYPE: RNA
<213> ORGANISM: Homo sapiens

<400> SEQUENCE: 237
acuuuaacau ggaggcacuu gc                                               22

<210> SEQ ID NO 238
<211> LENGTH: 17
<212> TYPE: RNA
<213> ORGANISM: Homo sapiens

<400> SEQUENCE: 238
uaagugcuuc caugcuu                                                     17

<210> SEQ ID NO 239
<211> LENGTH: 17
```

```
<212> TYPE: RNA
<213> ORGANISM: Homo sapiens

<400> SEQUENCE: 239
uaauugcuuc cauguuu                                                    17

<210> SEQ ID NO 240
<211> LENGTH: 22
<212> TYPE: RNA
<213> ORGANISM: Homo sapiens

<400> SEQUENCE: 240
aaaagcuggg uugagagggc ga                                              22

<210> SEQ ID NO 241
<211> LENGTH: 22
<212> TYPE: RNA
<213> ORGANISM: Homo sapiens

<400> SEQUENCE: 241
aaaagcuggg uugagagggc aa                                              22

<210> SEQ ID NO 242
<211> LENGTH: 22
<212> TYPE: RNA
<213> ORGANISM: Homo sapiens

<400> SEQUENCE: 242
aaaagcuggg uugagagggc aa                                              22

<210> SEQ ID NO 243
<211> LENGTH: 20
<212> TYPE: RNA
<213> ORGANISM: Homo sapiens

<400> SEQUENCE: 243
aaaagcuggg uugagagggu                                                 20

<210> SEQ ID NO 244
<211> LENGTH: 20
<212> TYPE: RNA
<213> ORGANISM: Homo sapiens

<400> SEQUENCE: 244
aaaagcuggg uugagagggu                                                 20

<210> SEQ ID NO 245
<211> LENGTH: 19
<212> TYPE: RNA
<213> ORGANISM: Homo sapiens

<400> SEQUENCE: 245
aaaagcuggg uugagagga                                                  19

<210> SEQ ID NO 246
<211> LENGTH: 19
<212> TYPE: RNA
<213> ORGANISM: Homo sapiens

<400> SEQUENCE: 246
aaaagcuggg uugagagga                                                  19

<210> SEQ ID NO 247
```

```
<211> LENGTH: 20
<212> TYPE: RNA
<213> ORGANISM: Homo sapiens

<400> SEQUENCE: 247
acugccccag gugcugcugg                                               20

<210> SEQ ID NO 248
<211> LENGTH: 23
<212> TYPE: RNA
<213> ORGANISM: Homo sapiens

<400> SEQUENCE: 248 cgcaucccu agggcauugg ugu                                            23

<210> SEQ ID NO 249
<211> LENGTH: 20
<212> TYPE: RNA
<213> ORGANISM: Homo sapiens

<400> SEQUENCE: 249
ccucugggcc cuuccuccag                                               20

<210> SEQ ID NO 250
<211> LENGTH: 22
<212> TYPE: RNA
<213> ORGANISM: Homo sapiens

<400> SEQUENCE: 250
cuggcccucu cugcccuucc gu                                            22

<210> SEQ ID NO 251
<211> LENGTH: 23
<212> TYPE: RNA
<213> ORGANISM: Homo sapiens

<400> SEQUENCE: 251
gcaaagcaca cggccugcag aga                                           23

<210> SEQ ID NO 252
<211> LENGTH: 22
<212> TYPE: RNA
<213> ORGANISM: Homo sapiens

<400> SEQUENCE: 252
ucucugggcc ugugucuuag gc                                            22

<210> SEQ ID NO 253
<211> LENGTH: 21
<212> TYPE: RNA
<213> ORGANISM: Homo sapiens

<400> SEQUENCE: 253
gccccugggc cuauccuaga a                                             21

<210> SEQ ID NO 254
<211> LENGTH: 22
<212> TYPE: RNA
<213> ORGANISM: Homo sapiens

<400> SEQUENCE: 254
cuagguaugg ucccagggau cc                                            22
```

```
<210> SEQ ID NO 255
<211> LENGTH: 23
<212> TYPE: RNA
<213> ORGANISM: Homo sapiens

<400> SEQUENCE: 255
ucaagagcaa uaacgaaaaa ugu                                          23

<210> SEQ ID NO 256
<211> LENGTH: 22
<212> TYPE: RNA
<213> ORGANISM: Homo sapiens

<400> SEQUENCE: 256
uuuuucauua uugcuccuga cc                                           22

<210> SEQ ID NO 257
<211> LENGTH: 23
<212> TYPE: RNA
<213> ORGANISM: Homo sapiens

<400> SEQUENCE: 257
ugagcgccuc gacgacagag ccg                                          23

<210> SEQ ID NO 258
<211> LENGTH: 23
<212> TYPE: RNA
<213> ORGANISM: Homo sapiens

<400> SEQUENCE: 258
ucccuguccu ccaggagcuc acg                                          23

<210> SEQ ID NO 259
<211> LENGTH: 22
<212> TYPE: RNA
<213> ORGANISM: Homo sapiens

<400> SEQUENCE: 259
uuauaaagca augagacuga uu                                           22

<210> SEQ ID NO 260
<211> LENGTH: 22
<212> TYPE: RNA
<213> ORGANISM: Homo sapiens

<400> SEQUENCE: 260
uccgucucag uuacuuuaua gc                                           22

<210> SEQ ID NO 261
<211> LENGTH: 23
<212> TYPE: RNA
<213> ORGANISM: Homo sapiens

<400> SEQUENCE: 261
ucucacacag aaaucgcacc cgu                                          23

<210> SEQ ID NO 262
<211> LENGTH: 21
<212> TYPE: RNA
<213> ORGANISM: Homo sapiens

<400> SEQUENCE: 262
aggggugcua ucugugauug a                                            21
```

```
<210> SEQ ID NO 263
<211> LENGTH: 22
<212> TYPE: RNA
<213> ORGANISM: Homo sapiens

<400> SEQUENCE: 263
gcugacuccu aguccagggc uc                                              22

<210> SEQ ID NO 264
<211> LENGTH: 23
<212> TYPE: RNA
<213> ORGANISM: Homo sapiens

<400> SEQUENCE: 264 uccccaggu gugauucuga uuu                                              23

<210> SEQ ID NO 265
<211> LENGTH: 22
<212> TYPE: RNA
<213> ORGANISM: Homo sapiens

<400> SEQUENCE: 265
uuaucagaau cuccaggggu ac                                              22

<210> SEQ ID NO 266
<211> LENGTH: 22
<212> TYPE: RNA
<213> ORGANISM: Homo sapiens

<400> SEQUENCE: 266
gccugcuggg guggaaccug gu                                              22

<210> SEQ ID NO 267
<211> LENGTH: 22
<212> TYPE: RNA
<213> ORGANISM: Homo sapiens

<400> SEQUENCE: 267
uuauaauaca accugauaag ug                                              22

<210> SEQ ID NO 268
<211> LENGTH: 22
<212> TYPE: RNA
<213> ORGANISM: Homo sapiens

<400> SEQUENCE: 268
auauaauaca accugcuaag ug                                              22

<210> SEQ ID NO 269
<211> LENGTH: 22
<212> TYPE: RNA
<213> ORGANISM: Homo sapiens

<400> SEQUENCE: 269
guagauucuc cuucuaugag ua                                              22

<210> SEQ ID NO 270
<211> LENGTH: 21
<212> TYPE: RNA
<213> ORGANISM: Homo sapiens

<400> SEQUENCE: 270
aucauagagg aaaauccacg u                                               21
```

```
<210> SEQ ID NO 271
<211> LENGTH: 21
<212> TYPE: RNA
<213> ORGANISM: Homo sapiens

<400> SEQUENCE: 271
aucauagagg aaaauccacg u                                              21

<210> SEQ ID NO 272
<211> LENGTH: 22
<212> TYPE: RNA
<213> ORGANISM: Homo sapiens

<400> SEQUENCE: 272
aucauagagg aaaauccaug uu                                             22

<210> SEQ ID NO 273
<211> LENGTH: 21
<212> TYPE: RNA
<213> ORGANISM: Homo sapiens

<400> SEQUENCE: 273
aacauagagg aaauuccacg u                                              21

<210> SEQ ID NO 274
<211> LENGTH: 21
<212> TYPE: RNA
<213> ORGANISM: Homo sapiens

<400> SEQUENCE: 274
acuggacuug gagucagaag g                                              21

<210> SEQ ID NO 275
<211> LENGTH: 22
<212> TYPE: RNA
<213> ORGANISM: Homo sapiens

<400> SEQUENCE: 275
cuccugacuc cagguccugu gu                                             22

<210> SEQ ID NO 276
<211> LENGTH: 22
<212> TYPE: RNA
<213> ORGANISM: Homo sapiens

<400> SEQUENCE: 276
gaaguuguuc gugguggauu cg                                             22

<210> SEQ ID NO 277
<211> LENGTH: 21
<212> TYPE: RNA
<213> ORGANISM: Homo sapiens

<400> SEQUENCE: 277
uaguagaccg uauagcguac g                                              21

<210> SEQ ID NO 278
<211> LENGTH: 22
<212> TYPE: RNA
<213> ORGANISM: Homo sapiens

<400> SEQUENCE: 278
```

-continued uauguaacac gguccacuaa cc                                        22

<210> SEQ ID NO 279
<211> LENGTH: 23
<212> TYPE: RNA
<213> ORGANISM: Homo sapiens

<400> SEQUENCE: 279
ugaggggcag agagcgagac uuu                                       23

<210> SEQ ID NO 280
<211> LENGTH: 23
<212> TYPE: RNA
<213> ORGANISM: Homo sapiens

<400> SEQUENCE: 280
agcucggucu gaggccccuc agu                                       23

<210> SEQ ID NO 281
<211> LENGTH: 22
<212> TYPE: RNA
<213> ORGANISM: Homo sapiens

<400> SEQUENCE: 281
aucgggaaug ucguguccgc cc                                        22

<210> SEQ ID NO 282
<211> LENGTH: 23
<212> TYPE: RNA
<213> ORGANISM: Homo sapiens

<400> SEQUENCE: 282
aaugacacga ucacucccgu uga                                       23

<210> SEQ ID NO 283
<211> LENGTH: 23
<212> TYPE: RNA
<213> ORGANISM: Homo sapiens

<400> SEQUENCE: 283
ucuuggagua ggucauuggg ugg                                       23

<210> SEQ ID NO 284
<211> LENGTH: 21
<212> TYPE: RNA
<213> ORGANISM: Homo sapiens

<400> SEQUENCE: 284
cuggauggcu ccuccauguc u                                         21

<210> SEQ ID NO 285
<211> LENGTH: 22
<212> TYPE: RNA
<213> ORGANISM: Homo sapiens

<400> SEQUENCE: 285
aucaugaugg gcuccucggu gu                                        22

<210> SEQ ID NO 286
<211> LENGTH: 22
<212> TYPE: RNA
<213> ORGANISM: Homo sapiens

<400> SEQUENCE: 286
ucaggcucag uccccucccg au                                                    22

<210> SEQ ID NO 287
<211> LENGTH: 22
<212> TYPE: RNA
<213> ORGANISM: Homo sapiens

<400> SEQUENCE: 287
gucauacacg gcucuccucu cu                                                    22

<210> SEQ ID NO 288
<211> LENGTH: 22
<212> TYPE: RNA
<213> ORGANISM: Homo sapiens

<400> SEQUENCE: 288
agaggcuggc cgugaugaau uc                                                    22

<210> SEQ ID NO 289
<211> LENGTH: 21
<212> TYPE: RNA
<213> ORGANISM: Homo sapiens

<400> SEQUENCE: 289
cggggcagcu caguacagga u                                                     21

<210> SEQ ID NO 290
<211> LENGTH: 22
<212> TYPE: RNA
<213> ORGANISM: Homo sapiens

<400> SEQUENCE: 290
uccuguacug agcugccccg ag                                                    22

<210> SEQ ID NO 291
<211> LENGTH: 22
<212> TYPE: RNA
<213> ORGANISM: Homo sapiens

<400> SEQUENCE: 291
aaucauacag ggacauccag uu                                                    22

<210> SEQ ID NO 292
<211> LENGTH: 22
<212> TYPE: RNA
<213> ORGANISM: Homo sapiens

<400> SEQUENCE: 292
aaucguacag ggucauccac uu                                                    22

<210> SEQ ID NO 293
<211> LENGTH: 22
<212> TYPE: RNA
<213> ORGANISM: Homo sapiens

<400> SEQUENCE: 293
caugccuuga guguaggacc gu                                                    22

<210> SEQ ID NO 294
<211> LENGTH: 22
<212> TYPE: RNA
<213> ORGANISM: Homo sapiens -continued

```
<400> SEQUENCE: 294
ccucccacac ccaaggcuug ca                                              22

<210> SEQ ID NO 295
<211> LENGTH: 22
<212> TYPE: RNA
<213> ORGANISM: Homo sapiens

<400> SEQUENCE: 295
ggagaaauua uccuuggugu gu                                              22

<210> SEQ ID NO 296
<211> LENGTH: 22
<212> TYPE: RNA
<213> ORGANISM: Homo sapiens

<400> SEQUENCE: 296
cacgcucaug cacacaccca ca                                              22

<210> SEQ ID NO 297
<211> LENGTH: 23
<212> TYPE: RNA
<213> ORGANISM: Homo sapiens

<400> SEQUENCE: 297
ugagugugug ugugugagug ugu                                             23

<210> SEQ ID NO 298
<211> LENGTH: 22
<212> TYPE: RNA
<213> ORGANISM: Homo sapiens

<400> SEQUENCE: 298
uuaugguuug ccugggacug ag                                              22

<210> SEQ ID NO 299
<211> LENGTH: 21
<212> TYPE: RNA
<213> ORGANISM: Homo sapiens

<400> SEQUENCE: 299
ucuaguaaga guggcagucg a                                               21

<210> SEQ ID NO 300
<211> LENGTH: 22
<212> TYPE: RNA
<213> ORGANISM: Homo sapiens

<400> SEQUENCE: 300
augcugacau auuuacuaga gg                                              22

<210> SEQ ID NO 301
<211> LENGTH: 22
<212> TYPE: RNA
<213> ORGANISM: Homo sapiens

<400> SEQUENCE: 301
acuuguaugc uagcucaggu ag                                              22
```

```
<210> SEQ ID NO 302
<211> LENGTH: 22
<212> TYPE: RNA
<213> ORGANISM: Homo sapiens

<400> SEQUENCE: 302
uacccauugc auaucggagu ug                                              22
```